United States Patent
Levin

(10) Patent No.: US 8,224,438 B2
(45) Date of Patent: Jul. 17, 2012

(54) METHOD FOR DIRECTED INTRANASAL ADMINISTRATION OF A COMPOSITION

(76) Inventor: Bruce H. Levin, Philadelphia, PA (US)

( * ) Notice: Subject to any disclaimer, the term of this patent is extended or adjusted under 35 U.S.C. 154(b) by 0 days.

(21) Appl. No.: 12/683,301

(22) Filed: Jan. 6, 2010

(65) Prior Publication Data

US 2010/0137940 A1    Jun. 3, 2010

Related U.S. Application Data

(63) Continuation of application No. 10/218,138, filed on Aug. 12, 2002, which is a continuation-in-part of application No. 09/737,302, filed on Dec. 15, 2000, now abandoned, and a continuation-in-part of application No. 09/492,946, filed on Jan. 27, 2000, now Pat. No. 6,491,940, and a continuation-in-part of application No. 09/118,615, filed on Jul. 17, 1998, now Pat. No. 6,432,986, said application No. 09/737,302 is a continuation-in-part of application No. 09/118,615, filed on Jul. 17, 1998, now Pat. No. 6,432,986.

(60) Provisional application No. 60/170,817, filed on Dec. 15, 1999, provisional application No. 60/117,398, filed on Jan. 27, 1999, provisional application No. 60/090,110, filed on Jul. 21, 1997, provisional application No. 60/072,845, filed on Jan. 28, 1998, provisional application No. 60/084,559, filed on May 6, 1998.

(51) Int. Cl.
*A61N 1/00* (2006.01)
(52) U.S. Cl. ............................................. 607/2
(58) Field of Classification Search ................. 607/2
See application file for complete search history.

(56) References Cited

U.S. PATENT DOCUMENTS

| | | | |
|---|---|---|---|
| 2,123,980 A | 7/1938 | Warwick |
| 2,182,071 A | 12/1939 | Crossley |
| 3,357,434 A | 12/1967 | Abell |
| 3,746,004 A | 7/1973 | Jankelson |
| 3,862,321 A | 1/1975 | Adams et al. |

(Continued)

FOREIGN PATENT DOCUMENTS

EP    69427 A2    1/1983

(Continued)

OTHER PUBLICATIONS

Karavis, Acupuncture in Medicine, May 1997;15(1):33-42.*

(Continued)

*Primary Examiner* — San-Ming Hui
(74) *Attorney, Agent, or Firm* — Shay Glenn LLP

(57) ABSTRACT

Methods, kits, apparatus, and compositions for inhibiting a cerebral neurovascular disorder, a muscular headache, or cerebral inflammation in a human patient are provided. The methods comprise intranasally administering to the patient a pharmaceutical composition comprising a local anesthetic, and preferably a long-acting local anesthetic ingredient. A composition useful for practicing the methods of the invention is described which comprises at least one local anesthetic in a pharmaceutically acceptable carrier, wherein the composition is formulated for intranasal delivery. Cerebral neurovascular disorders include migraine and cluster headache. Muscular headaches include tension headaches and muscle contraction headaches. A kit comprising the composition and an intranasal applicator and a method of systemically delivering a pharmaceutically active agent to an animal are also included in the invention. Apparatus for directed intranasal administration of the compositions of the invention and for performing the methods of the invention are also described.

9 Claims, 8 Drawing Sheets

U.S. PATENT DOCUMENTS

| | | | |
|---|---|---|---|
| 3,914,283 A | 10/1975 | Okamoto et al. | |
| 3,923,060 A | 12/1975 | Ellinwood, Jr. | |
| 3,925,469 A | 12/1975 | Adams et al. | |
| 4,073,917 A | 2/1978 | Sandberg et al. | |
| 4,102,344 A | 7/1978 | Conway et al. | |
| 4,117,160 A | 9/1978 | Molnar et al. | |
| 4,147,804 A | 4/1979 | Diamond et al. | |
| 4,217,349 A | 8/1980 | Katsube et al. | |
| 4,298,603 A | 11/1981 | Chang et al. | |
| 4,305,402 A | 12/1981 | Katims | |
| 4,352,820 A | 10/1982 | Scurlock et al. | |
| 4,379,161 A | 4/1983 | Thominet et al. | |
| 4,397,845 A | 8/1983 | Allen | |
| 4,441,210 A | 4/1984 | Hochmair et al. | |
| 4,495,174 A | 1/1985 | Allcock et al. | |
| 4,519,400 A | 5/1985 | Brenman et al. | |
| 4,529,601 A | 7/1985 | Broberg et al. | |
| 4,550,733 A | 11/1985 | Liss et al. | |
| 4,551,453 A | 11/1985 | Marsili | |
| 4,565,200 A | 1/1986 | Cosman | |
| 4,592,359 A | 6/1986 | Galbraith | |
| 4,622,219 A | 11/1986 | Haynes | |
| 4,627,438 A | 12/1986 | Liss et al. | |
| 4,632,940 A | 12/1986 | Chiarino et al. | |
| 4,646,744 A | 3/1987 | Capel | |
| 4,692,147 A | 9/1987 | Duggan | |
| 4,695,576 A | 9/1987 | af Ekenstam et al. | |
| 4,718,423 A | 1/1988 | Willis et al. | |
| 4,727,145 A | 2/1988 | Press | |
| 4,776,349 A | 10/1988 | Nashef et al. | |
| 4,784,142 A | 11/1988 | Liss et al. | |
| 4,830,008 A | 5/1989 | Meer | |
| 4,833,149 A | 5/1989 | Press | |
| 4,856,526 A | 8/1989 | Liss et al. | |
| 4,870,086 A | 9/1989 | Sandberg | |
| 4,871,475 A | 10/1989 | Lubowitz et al. | |
| 4,886,493 A * | 12/1989 | Yee | 604/516 |
| 4,920,979 A | 5/1990 | Bullara | |
| 4,937,078 A | 6/1990 | Mezei et al. | |
| 4,976,711 A | 12/1990 | Parins et al. | |
| 5,038,781 A | 8/1991 | Lynch | |
| 5,085,868 A | 2/1992 | Mattsson et al. | |
| 5,178,156 A | 1/1993 | Takishima et al. | |
| 5,193,539 A | 3/1993 | Schulman et al. | |
| 5,199,428 A | 4/1993 | Obel et al. | |
| 5,215,086 A | 6/1993 | Terry, Jr. et al. | |
| 5,227,165 A | 7/1993 | Domb et al. | |
| 5,234,957 A | 8/1993 | Mantelle | |
| 5,255,691 A | 10/1993 | Otten | |
| 5,259,387 A | 11/1993 | dePinto | |
| 5,314,458 A | 5/1994 | Najafi | |
| 5,318,592 A | 6/1994 | Schaldach | |
| 5,330,515 A | 7/1994 | Rutecki et al. | |
| 5,335,657 A | 8/1994 | Terry, Jr. et al. | |
| 5,344,438 A | 9/1994 | Testerman et al. | |
| 5,360,805 A | 11/1994 | Ask et al. | |
| 5,387,587 A | 2/1995 | Hausler et al. | |
| 5,411,546 A | 5/1995 | Bowald et al. | |
| 5,420,151 A | 5/1995 | Hammarberg et al. | |
| 5,428,006 A | 6/1995 | Bechgaard et al. | |
| 5,433,739 A | 7/1995 | Sluijter et al. | |
| 5,458,626 A | 10/1995 | Krause | |
| 5,458,631 A | 10/1995 | Xavier | |
| 5,490,520 A | 2/1996 | Schaefer et al. | |
| 5,514,131 A | 5/1996 | Edwards et al. | |
| 5,540,730 A | 7/1996 | Terry, Jr. et al. | |
| 5,540,734 A | 7/1996 | Zabara | |
| 5,545,219 A | 8/1996 | Kuzma | |
| 5,558,622 A | 9/1996 | Greenberg | |
| 5,569,166 A | 10/1996 | Stone | |
| 5,578,061 A | 11/1996 | Stroetmann et al. | |
| 5,591,216 A | 1/1997 | Testerman et al. | |
| 5,639,772 A | 6/1997 | Hammarberg et al. | |
| 5,645,570 A | 7/1997 | Corbucci | |
| 5,653,734 A | 8/1997 | Alt | |
| 5,656,657 A | 8/1997 | Hammarberg et al. | |
| 5,658,318 A | 8/1997 | Stroetmann et al. | |
| 5,660,837 A | 8/1997 | Lundquist | |
| 5,676,955 A | 10/1997 | Ansmann et al. | |
| 5,700,282 A | 12/1997 | Zabara | |
| 5,707,400 A | 1/1998 | Terry, Jr. et al. | |
| 5,711,316 A | 1/1998 | Elsberry et al. | |
| 5,713,922 A | 2/1998 | King | |
| 5,735,817 A | 4/1998 | Shantha | |
| 5,756,520 A | 5/1998 | Ask et al. | |
| 5,766,605 A | 6/1998 | Sanders et al. | |
| 5,824,027 A | 10/1998 | Hoffer et al. | |
| 5,843,021 A | 12/1998 | Edwards et al. | |
| 5,861,014 A | 1/1999 | Familoni | |
| 5,865,843 A | 2/1999 | Baudino | |
| 5,938,688 A | 8/1999 | Schiff | |
| 6,001,088 A | 12/1999 | Roberts et al. | |
| 6,006,134 A | 12/1999 | Hill et al. | |
| 6,016,449 A | 1/2000 | Fischell et al. | |
| 6,026,326 A | 2/2000 | Bardy | |
| 6,058,331 A | 5/2000 | King | |
| 6,073,048 A | 6/2000 | Kieval et al. | |
| 6,093,145 A | 7/2000 | Vom Berg et al. | |
| 6,094,598 A | 7/2000 | Elsberry et al. | |
| 6,104,957 A | 8/2000 | Alo et al. | |
| 6,128,538 A | 10/2000 | Fischell et al. | |
| 6,132,384 A | 10/2000 | Christopherson et al. | |
| 6,134,474 A | 10/2000 | Fischell et al. | |
| 6,141,590 A | 10/2000 | Renirie et al. | |
| 6,146,380 A | 11/2000 | Racz et al. | |
| 6,161,044 A | 12/2000 | Silverstone | |
| 6,161,048 A | 12/2000 | Sluijter et al. | |
| 6,178,349 B1 | 1/2001 | Kieval | |
| 6,205,359 B1 | 3/2001 | Boveja | |
| 6,246,912 B1 | 6/2001 | Sluijter et al. | |
| 6,251,126 B1 | 6/2001 | Ottenhoff et al. | |
| 6,259,952 B1 | 7/2001 | Sluijter et al. | |
| 6,262,377 B1 | 7/2001 | Nielsen et al. | |
| 6,269,270 B1 | 7/2001 | Boveja | |
| 6,292,695 B1 | 9/2001 | Webster, Jr. et al. | |
| 6,308,105 B1 | 10/2001 | Duysens et al. | |
| 6,353,762 B1 | 3/2002 | Murthy | |
| 6,356,786 B1 | 3/2002 | Rezai et al. | |
| 6,356,787 B1 | 3/2002 | Rezai et al. | |
| 6,356,788 B2 | 3/2002 | Boveja | |
| 6,366,814 B1 | 4/2002 | Boveja et al. | |
| 6,400,982 B2 | 6/2002 | Sweeney et al. | |
| 6,405,079 B1 | 6/2002 | Ansarinia | |
| 6,432,986 B2 | 8/2002 | Levin | |
| 6,438,423 B1 | 8/2002 | Rezai et al. | |
| 6,456,786 B1 | 9/2002 | Uchida et al. | |
| 6,458,157 B1 | 10/2002 | Suaning | |
| 6,491,940 B1 | 12/2002 | Levin | |
| 6,511,500 B1 | 1/2003 | Rahme | |
| 6,526,318 B1 | 2/2003 | Ansarinia | |
| 6,564,096 B2 | 5/2003 | Mest | |
| 6,564,102 B1 | 5/2003 | Boveja | |
| 6,610,713 B2 | 8/2003 | Tracey | |
| 6,615,081 B1 | 9/2003 | Boveja | |
| 6,633,779 B1 | 10/2003 | Schuler | |
| 6,647,296 B2 | 11/2003 | Fischell et al. | |
| 6,665,562 B2 | 12/2003 | Gluckman et al. | |
| 6,668,191 B1 | 12/2003 | Boveja | |
| 6,735,475 B1 | 5/2004 | Whitehurst et al. | |
| 6,760,626 B1 | 7/2004 | Boveja | |
| 6,788,975 B1 | 9/2004 | Whitehurst et al. | |
| RE38,654 E | 11/2004 | Hill et al. | |
| 6,819,956 B2 | 11/2004 | DiLorenzo | |
| 6,853,858 B2 | 2/2005 | Shalev | |
| 6,885,888 B2 | 4/2005 | Rezai | |
| 7,003,352 B1 | 2/2006 | Whitehurst | |
| 7,076,307 B2 | 7/2006 | Boveja et al. | |
| 7,113,033 B2 | 9/2006 | Barnett | |
| 7,117,033 B2 | 10/2006 | Shalev et al. | |
| 7,120,489 B2 | 10/2006 | Shalev et al. | |
| 7,167,751 B1 | 1/2007 | Whitehurst et al. | |
| 7,203,548 B2 | 4/2007 | Whitehurst et al. | |
| 7,209,787 B2 | 4/2007 | DiLorenzo | |
| 7,277,758 B2 | 10/2007 | DiLorenzo | |
| 7,285,118 B1 | 10/2007 | Lozano | |
| 7,292,890 B2 | 11/2007 | Whitehurst et al. | |
| 7,369,897 B2 | 5/2008 | Boveja et al. | |

| | | |
|---|---|---|
| 7,403,821 B2 | 7/2008 | Haugland et al. |
| 7,477,945 B2 | 1/2009 | Rezai et al. |
| 2002/0026222 A1 | 2/2002 | Schauerte et al. |
| 2002/0107553 A1 | 8/2002 | Hill et al. |
| 2002/0169365 A1 | 11/2002 | Nakada et al. |
| 2003/0004549 A1 | 1/2003 | Hill et al. |
| 2003/0018367 A1 | 1/2003 | DiLorenzo |
| 2003/0018368 A1 | 1/2003 | Ansarinia |
| 2003/0060857 A1 | 3/2003 | Perrson et al. |
| 2003/0100924 A1 | 5/2003 | Foreman et al. |
| 2003/0133877 A1 | 7/2003 | Levin |
| 2003/0144709 A1 | 7/2003 | Zabara et al. |
| 2003/0181951 A1 | 9/2003 | Cates |
| 2003/0181958 A1 | 9/2003 | Dobak, III |
| 2003/0181959 A1 | 9/2003 | Dobak, III |
| 2003/0212440 A1 | 11/2003 | Boveja |
| 2003/0216792 A1 | 11/2003 | Levin et al. |
| 2004/0015204 A1 | 1/2004 | Whitehurst et al. |
| 2004/0019364 A1 | 1/2004 | Kieval et al. |
| 2004/0049235 A1 | 3/2004 | Deno et al. |
| 2004/0210295 A1 | 10/2004 | Brushey |
| 2004/0230255 A1 | 11/2004 | Dobak, III |
| 2005/0065562 A1 | 3/2005 | Rezai |
| 2005/0065573 A1 | 3/2005 | Rezai |
| 2005/0143787 A1 | 6/2005 | Boveja et al. |
| 2005/0154419 A1 | 7/2005 | Whitehurst et al. |
| 2005/0154426 A1 | 7/2005 | Boveja et al. |
| 2005/0159790 A1 | 7/2005 | Shalev |
| 2005/0197675 A1 | 9/2005 | David et al. |
| 2005/0209654 A1 | 9/2005 | Boveja et al. |
| 2005/0216070 A1 | 9/2005 | Boveja et al. |
| 2005/0281751 A1 | 12/2005 | Levin |
| 2006/0004423 A1 | 1/2006 | Boveja et al. |
| 2006/0020299 A1 | 1/2006 | Shalev |
| 2006/0064140 A1 | 3/2006 | Whitehurst et al. |
| 2006/0085046 A1 | 4/2006 | Rezai |
| 2006/0100667 A1 | 5/2006 | Machado et al. |
| 2006/0111754 A1 | 5/2006 | Rezai |
| 2007/0067004 A1 | 3/2007 | Boveja et al. |
| 2007/0156177 A1 | 7/2007 | Harel et al. |
| 2007/0167984 A1 | 7/2007 | Kieval et al. |
| 2007/0203521 A1 | 8/2007 | Dobak et al. |
| 2009/0216287 A1 | 8/2009 | Ansarinia |
| 2009/0254147 A1 | 10/2009 | Ansarinia |
| 2009/0276005 A1 | 11/2009 | Pless |
| 2011/0029037 A1 | 2/2011 | Rezai et al. |

FOREIGN PATENT DOCUMENTS

| | | |
|---|---|---|
| EP | 0970813 A2 | 1/2000 |
| EP | 754060 B1 | 3/2003 |
| RU | 2108817 C1 | 4/1996 |
| WO | WO85/00599 A1 | 2/1985 |
| WO | WO92/07605 A1 | 5/1992 |
| WO | WO95/21821 A1 | 2/1994 |
| WO | WO97/02000 A1 | 1/1997 |
| WO | WO97/15548 A1 | 5/1997 |
| WO | WO97/23467 A1 | 7/1997 |
| WO | WO97/38675 A1 | 10/1997 |
| WO | WO01/85094 A2 | 11/2001 |
| WO | WO01/97905 A1 | 12/2001 |
| WO | WO03/082123 A2 | 10/2003 |

OTHER PUBLICATIONS

Guo et al., Journal of Traditional Chinese Medicine, Mar. 1995:15(1):31-33.*
Gromova et al.; Sinusoidal modulated currents in comprehensive treatment of children with bronchial asthma; Voprosy Kurortologii Fizioterapii, I Lechebnoi Fizicheskoi Kultury; May-Jun.; (3); pp. 45-47; 1981 (w/ English Abstract).
Karashurov et al.; Radio frequency electrostimulation of the gangliated cord of the sympathetic nerve in patients with bronchial asthma; Surgery (Khigurgiia); vol. 1; pp. 44-46; 2000 (w/ English Abstract).
Pless et al.; U.S. Appl. No. 12/649,119 entitled "Integrated Delivery and Visualization Tool for a Neuromodulation System," filed Dec. 29, 2009.
Fletcher et al.; U.S. Appl. No. 12/688,524 entitled "Approval Per Use Implanted Neurostimulator," filed Jan. 15, 2010.

Wingeier et al.; U.S. Appl. No. 12/692,444 entitled "Method and Devices for Adrenal Stimulation," filed Jan. 22, 2010.
Ardell et al.; "Differential sympathetic regulation of automatic, conductile, and contractile tissue in dog heart;" American Physiological Society; pp. H1050-H1059; Jun. 6, 1988.
Babe, "Treatment of sphenopalatine ganglion neuralgia", An Otorrinolaringol Ibero Am, vol. 16(5): 463-74 (1989) (abstract).
Barre, "Cocaine as an abortive agent in cluster headache", Headache, vol. 22: 69-73 (1982).
Benumof et al.; Pulmonary artery catheterization; In Clinical Procedures in Anesthesia and Intensive Care; JB Lippincott Company; pp. 405-441; 1992.
Berger et al., "Does topical anesthesia of the sphenopalatine ganglion with cocaine or lidocaine relieve low back pain?", Anesth Analg, vol. 35: 87-108 (1925).
Brooksby et al.; Dynamic changes in splanchnic blood flow and blood volume in dogs during activation of sympathetic nerves; Circulation Research; vol. 29; pp. 227-238; 1971.
Brooksby et al; Release of blood from the splanchnic circulation in dogs; Circulation Research; vol. 31; pp. 105-118; 1972.
Browne et al., "Concurrent cervical and craniofacial pain" Oral Surg Oral Med Oral Path 86(6): 633-640 (Dec. 1998).
Carneiro et al.; Blood reservoir function of dog spleen, liver and intestine; American Journal of Physiology; vol. 232; No. 1; pp. H67-H72; 1977.
Carroll et al., "Motor cortex stimulation for chronic neuropathic pain: a preliminary study of 10 cases" Pain 84:431-437 (2000).
Cepero et al., "Long-term results of sphenopalatine ganglioneurectomy for facial pain", Am J Otolaryngol, 8(3): 171-4 (1987).
Cook, "Cryosurgery of headache", Res Clin Stud Headache, vol. 5: 86-101 (1978) (abstract).
Cooper et al.; Neural effects on sinus rate and atrioventricular conduction produced by electrical stimulation from a transvenous electrode catheter in the canine right pulmonary artery; Circulation Research; vol. 46; pp. 48-57; 1980.
Cutrer et al., "Effects of PNU-109,291, a selective 5H-T1D receptor agonist, on electrically induced dural plasma extravasation and capsaicin-evoked c-fos immunoreactivity within trigeminal nucleus caudalis" Neuropharm 38:1043-1053 (1999).
Delepine et al., "Plasma protein extravasation induced in the rat dura mater by stimulation of the parasympathetic sphenopalatine ganglion", Exp Neurology, vol. 147: 389-400 (1997).
Devoghel, "Cluster headache and sphenopalatine block", Acta Anaesthesio Belg, vol. 32(1), pp. 101-107 (1981).
Feindel et al., "The tentorial nerves and localization of intracranial pain in man" Neurology 555-563 (1955).
Ferrante et al., "Sphenopalatine ganglion block for the treatment of myofascial pain of head, neck, and shoulders", Reg Anesth Pain, vol. 23(1): 30-6 (1998) (abstract).
Frisardi et al., "Electric versus magnetic transcranial stimulation of the trigeminal system in healthy subjects. Clinical applications in gnathology.", J Oral Rehabil, 24(12): 920-8 (1986) (abstract).
Goadsby et al., "Differential effects of low dose CP122,288 and eletriptan on Fos expression due to stimulation of the superior sagittal sinus in cat" Pain 82:15-22 (1999).
Goadsby et al., "Stimulation of an intracranial trigeminally-innervated structure selectively increases cerebral blood flow" Brain Research 751:247-252 (1997).
Goadsby et al., "Substance P blockade with the potent and centrally acting antagonist GR205171 does not effect central trigeminal activity with superior sagittal sinus stimuation" Neuroscience 86(1);337-343 (1998).
Goadsby et al., "The trigeminovascular system and migraine: studies characterizing cerebrovascular and neuropeptide changes seen in humans and cats" Ann Neurol 33:48-56 (1993).
Goadsby et al., Effect of stimulation of trigeminal ganglion on regional cerebral blood flow in cats; Am J. Physiol.; vol. 22; pp. R270-R274; 1987.
Goadsby, "Sphenopalatine ganglion stimulation increases regional blood flow independent of glucose utilization in the cat", Brain Research, vol. 506: 145-8 (1990).

Gregoire, "Cluster headaches", Can Nurse, vol. 87(9): 33-5 (1991) (abstract).
Hardebo, Jan-Erik; Activation of pain fibers to the internal carotid artery intracranially may cause the pain and local signs of reduced sympathetic and enhanced parasympathetic activity in cluster headache; Headache; 31; pp. 314-320; May 1991.
Hardebo, Jan-Erik; On pain mechanisms in cluster headache; Headache; 31; pp. 91-106; 1991.
Headache Classification Committee of the International Headache Society, "Classification and diagnostic criteria for headache disorders, cranial neuralgias and facial pain", Cephalalgia, Supp & 0:13, 19-24 and 35-38 (1988).
Heusch et al.; Adrenergic mechanisms in myocardial ischemia; Supp. to Basic Research in Cardiology; vol. 85; 1990.
Hillier; Monitored anesthesia care; Clinical Anesthesia; Ch. 47; pp. 1239-1254; 2001.
Hoskin et al., "Fos expression in the trigeminocervical complex of the cat after stimulation of superior sagittal sinus is reduced by L-NAME" Neuroscience Letters 266:173-176 (1999).
Hudson; Basic principles of clinical pharmacology; Clinical Anesthesia; Ch. 11; pp. 239-260; 2001.
Janes et al.; Anatomy of human extrinsic cardiac nerves and ganglia; American Journal of Cardiology; vol. 57; pp. 299-309; 1986.
Janzen et al., "Sphenopalatine blocks in the treatment of pain in fibromyalgia and myofascial pain syndrome", Laryngoscope, vol. 107(10): 1420-2 (1997).
Kittrelle et al., "Cluster headache. Local anesthetic abortive agents", Arch Neurol, vol. 42(5): 496-8 (May 1985).
Kudrow et al., "Rapid and sustained relief of migraine attacks with intranasal lidocaine: preliminary findings", Headache, vol. 25: 79-82 (1995).
Kudrow, "Natural history of cluster headaches—part 1 outcome of drop-out patients", Headache, vol. 22: 203-6 (1982).
Kushiku et al.; Upregulation of Immunoreactive Angiotensin II Release and Angiotensinogen mRNA Expression by High-Frequency Preganglionic Stimulation at the Canine Cardiac Sympathetic Ganglia; Circ Res.; 88; pp. 110-116; 2001.
Lambert et al.; Comparative effects of stimulation of the trigeminal ganglion and the superior sagittal sinus on cerebral blood flow and evoked potentials in the cat; Brain Research; vol. 453; pp. 143-149; 1988.
Lebovits et al., "Sphenopalatine ganglion block: clinical use in the pain management clinic", Clin J Pain, vol. 6(2): 131-6 (1990).
Levine et al.; Central venous and pulmonary artery catheter monitoring; Critical Care Monitoring from Pre-Hospital to the ICU; pp. 145-158.
Maizels et al., "Intranasal lidocaine for treatment of migraine", JAMA, vol. 276(4): 319-21 (1996).
Manahan et al., "Sphenopalatine ganglion block relieves symptoms of trigeminal neuralgia: a case report", Nebr Med J, vol. 81(9): 306-9 (1996) (abstract).
Matsumoto et al.; Effective sites by sympathetic beta-andrenergic and vagal nonadrenergic inhibitory stimulation in constricted airways; Am Rev Respir Dis; vol. 132; pp. 1113-1117; Nov. 1985.
Matthey et al.; Bedside catheterization of the pulmonary artery: risks compared with benefits; In Clinical Procedures in Anesthesia and Intensive Care; JB Lippincott Company; vol. 109; pp. 826-834; 1988.
Meyer et al., "Sphenopalatine ganglionectomy for cluster headache", Arch Otolaryngol, vol. 92(5): 475-84 (Nov. 1970).
Meyerson et al.; Alleviation of Atypical trigeminal pain by stimulation of the gasserian ganglion via an implanted electrode; Acta Neurochirurgica; supp. 30; pp. 303-309; 1980.
Moskowitz et al., "Basic mechanisms in vascular headache" Headache 8 (4):801-815 (Nov. 1990).
Moskowitz, Michael; Cluster headache: evidence for a pathophysiologic focus in the superior pericarotid cavernous sinus plexus; Headache; vol. 28; pp. 584-586; 1988.
Moskowitz; Neurogenic inflammation in the pathophysiology and treatment of migraine; Neurology; vol. 43; suppl. 3; pp. S16-S20; 1993.
Murphy et al.; Human cardiac nerve stimulation; The Annals of Thoracic Surgery; vol. 54; p. 502; 1992.

Nguyen et al., "Chronic motor cortex stimulation in the treatment of central and neuropathic pain. Correlations between clinical, electrophysiological and anatomical data" Pain 82:245-251 (1999).
Onofrio et al., "Surgical treatment of chronic cluster headache", Mayo Clin Proc, vol. 61(7), pp. 537-44 (1986).
Peterson et al., "Sphenopalatine ganglion block: a safe and easy method for the management of orofacial pain", Cranio, vol. 13(3): 177-81 (1995) (abstract).
Phebus et al., "The non-peptide NK-1 receptor antagonist LY303870 inhibits neurogenic dural inflammation in guinea pigs" Life Sciences 60(18):1553-1561 (1997).
Pollock et al., "Stereotactic radiosurgical treatment of sphenopalatine neuralgia", J Neurosurg, vol. 87(3): 450-3 (1997).
Reder et al., "Sphenopalatine ganglion block in treatment of acute and chronic pain", Diagnosis and treatment of chronic pain, John Wright, publisher, 97-108 (1982).
Reuter et al.; Experimental models of migraine; Funct Neurol; suppl. 15; pp. 9-18; 2000.
Ruskin, "Contributions to the study of the sphenopalatine ganglion", Laryngoscope, vol. 35(2): 87-108 (1925).
Ruskin; Sphenopalatine (nasal) gaglion: remote effects including "psychosomatic" symptons, rage reaction, pain, and spasm; Arch Phys Med Rehabil; vol. 60; pp. 353-359; Aug. 1979.
Ryan et al., "Sphenopalatine ganglion neuralgia and cluster headache: comparisons, contrasts, and treatment", Headache, vol. 17: 7-8 (1977).
Saade et al., "Patient-administered sphenopalatine ganglion block", Reg Anesth, vol. 21(1): 68-70 (1996) (abstract).
Sanders et al., "Efficacy of sphenopalatine ganglion blockade in 66 patients suffering from cluster headache: a 12- to 70- month follow-up evaluation", J Neurosurg., vol. 87(6), pp. 876-880 (Dec. 1997).
Scherlag et al.; Endovascular stimulation within the left pulmonary artery to induce slowing of heart rate and paroxysmal atrial fibrillation; Cardiovascular Research; vol. 54; pp. 470-475; 2002.
Schulz et al., "Localization of epileptic auras induced on stimulation by subdural electrodes" Epilepsia 38(12) 1321-1329 (1997).
Seylaz et al., "Effect of stimulation of the sphenopalatine ganglion on cortical blood flow in the rat", J Cerebr Blood Flow and Metab, vol. 8: 875-8 (1988).
Shuster et al., "Treatment of vasomotor rhinitis, trigeminal neuralgia and Sluder's syndrome by irradiation of the sphenopalatine ganglion with helium-neon lasers", Vestin Otorinolaringol, vol. 4: 35-40 (1988).
Sluder, "The syndrome of sphenopalatine ganglion neuralgia", Am J Medicament Sci, vol. 111: 868-878 (1910).
Sluder; The anatomical and clinical relations of the sphenopalatine (Meckel's) ganglion to the nose and its accessory sinuses; NY Med. J.; vol. 90; pp. 293-298; Aug. 1909.
Steude; Percutaneous electro stimulation of the trigeminal nerve in patients with atypical trigeminal neuralgia; Neurochirurgia; vol. 21; pp. 66-69; 1978.
Storer et al., "Microiontophoretic application of serotonin (5HT) 1B/1D agonists inhibits trigeminal cell firing in the cat" Brain 120:2171-2177 (1997).
Strassman et al., "Sensitization of meningeal sensory neurons and the origin of headaches" Nature 384:560-563 (Dec. 1996).
Suzuki et al., "Selective electrical stimulation of postganglionic cerebrovascular parasympathetic nerve fibers originating from the sphenopalatine ganglion enhances cortical blood flow in the rat", J Cerebr Blood Flow and Metab, vol. 10: 383-391 (1990).
Suzuki et al.; Trigeminal fibre collaterals storing substance P and calcitonin gene-related peptide ; Neuroscience; vol. 30; No. 3; pp. 595-604; 1989.
Taub et al., "Chronic electrical stimulation of the gasserian ganglion for the relief of pain in a series of 34 patients", J Neurosurg, vol. 86: 197-202 (1997).
Thalamic Stimulation and Trigeminal Neuralgia; Neuroscience Pathways (Publication of the Cleveland Clinic Foundation); Spring 1998 newsletter; pp. 1-2.
Walters et al.; Cerebrovascular projections from the sphenopalatine and otic ganglia to the middle cerebral artery of the cat; Stroke; vol. 17; pp. 488-494; 1986.

Young, "Electrical stimulation of the trigeminal nerve root for the treatment of chronic facial pain", J Neurosurg, vol. 83: 72-78 (1995).

Witte et al.; Experimental heart failure in rats: effects on cardiovascular circadian rhythms and on myocardial ?-adrenergic signaling; Cardiovasc Res; vol. 47; pp. 350-358; 2000.

Yee et al.; Circadian variation in the effects of aldosterone blockade on heart rate variability and QT dispersion in congestive heart failure; J. Am. Coll. Cardiol.; vol. 37; pp. 1800-1807; 2001.

Boling et al.; U.S. Appl. No. 12/765,712 entitled "Implantable Neurostimulator with Integral Hermetic Electronic Enclosure, Circuit Substrate, Monolithic Feed-Through, Lead Assembly and Anchoring Mechanism," filed Apr. 22, 2010.

Wingeier et al.; U.S. Appl. No. 12/791,690 entitled "Methods and Devices for Adrenal Stimulation," filed Jun. 1, 2010.

Rao et al., "Effectiveness of temporal pattern in the input to a ganglion: Inhibition in the cardiac ganglion of spiny lobsters", J of Neurobiology, vol. 1, No. 2, pp. 233-245 (1969) (abstract).

* cited by examiner

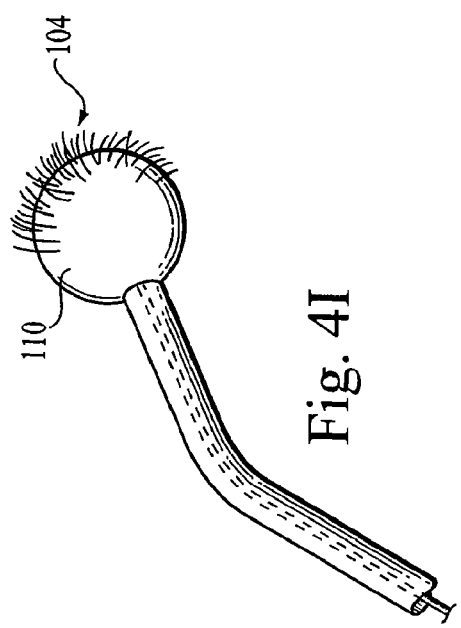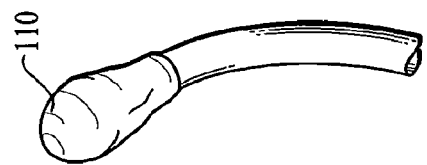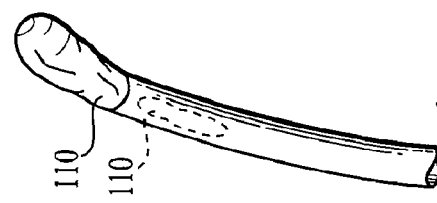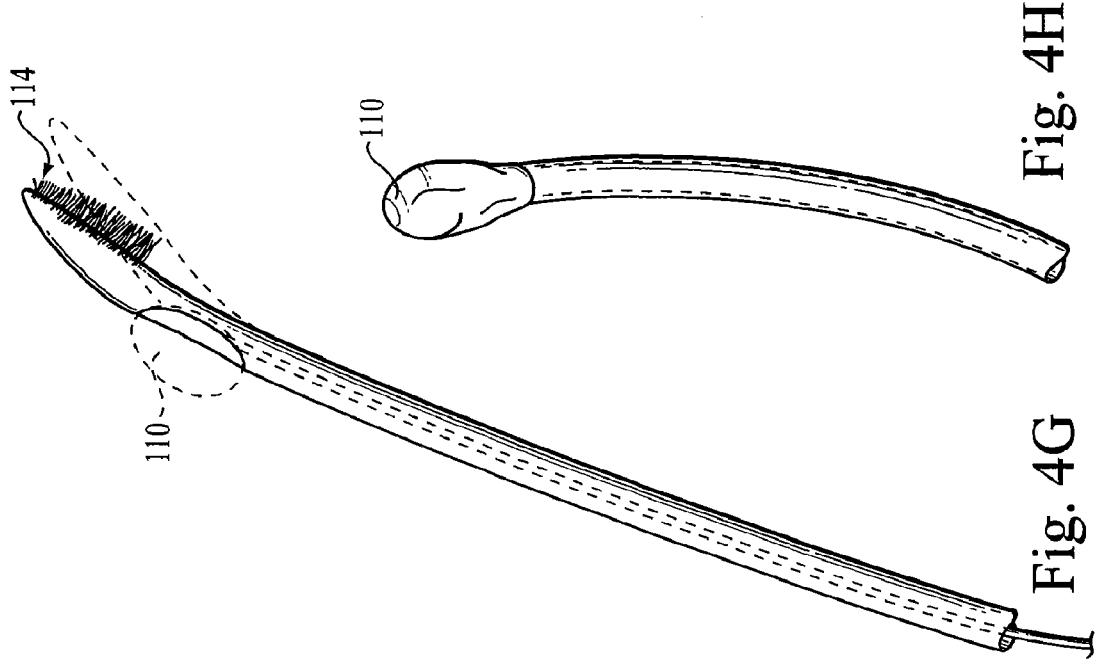

METHOD FOR DIRECTED INTRANASAL
ADMINISTRATION OF A COMPOSITION

CROSS-REFERENCE TO RELATED APPLICATIONS

This application is a continuation of pending U.S. application Ser. No. 10/218,138, filed Aug. 12, 2002. application Ser. No. 10/218,138 is a continuation-in-part of three prior applications, namely, U.S. application Ser. No. 09/737,302, filed Dec. 15, 2000, now abandoned; U.S. application Ser. No. 09/492,946, filed Jan. 27, 2000, now U.S. Pat. No. 6,491,940; and U.S. application Ser. No. 09/118,615, filed Jul. 17, 1998, now U.S. Pat. No. 6,432,986. application Ser. No. 09/737,302 is a continuation-in-part of application Ser. No. 09/118,615 and is also entitled to priority pursuant to 35 U.S.C. §119(e) to U.S. Provisional Application No. 60/170,817, filed Dec. 15, 1999. Application Ser. No. 09/492,946 is entitled to priority pursuant to 35 U.S.C. 119(e) to U.S. Provisional Application No. 60/117,398, filed Jan. 27, 1999. Application Ser. No. 09/118,615 is entitled pursuant to 35 U.S.C. §119(e) to U.S. Provisional Application No. 60/090,110, filed Jul. 21, 1997; U.S. Provisional Application No. 60/072,845, filed Jan. 28, 1998; and to U.S. Provisional Application No. 60/084,559, filed May 6, 1998.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention relates to compositions, kits, methods, and apparatus for inhibiting muscular headaches and cerebral neurovascular disorders including, but not limited to, neurovascular headaches, migraines, cluster headaches, tinnitus, cerebrovascular spasm, ischemic disorders, seizures, central neuraxial motor, sensory, and cognitive deficits, degenerative, traumatic, or infectious lesions of the central nervous system, and cephalic inflammation including, but not limited to, meningeal inflammation, intracranial inflammation, extracranial inflammation. The invention also relates to apparatus and methods for directing intranasal administration of a composition to a selected portion of the nasal cavity, such as the superior portion or the dorsonasal portion.

Headache is a common symptom of numerous diseases and disorders including, but not limited to, migraine, muscle tension, systemic or intracranial infection, intracranial tumor, head injuries, severe hypertension, cerebral hypoxia, certain diseases of the eyes, nose, throat, teeth, and ears, and head pain for which no cause can be determined.

Infrequent headaches can often be determined to result from causes attributable to a particular experience of a patient, such as fatigue, fever, alcohol ingestion, muscle contraction, tension, or the like. The cause of persistent or recurrent headaches is often difficult to determine. Persistent or recurrent headaches include, but are not limited to, muscular headaches, such as tension or muscle contraction headaches, and neurovascular headaches, such as migraines and cluster headaches.

Cerebral neurovascular disorders (CNvDs) are characterized by one or more disturbances in the normal functioning of at least one component of the cerebral vascular or nervous system in a human. CNvDs include, for example, migraine, cluster headaches, other headaches of neurovascular etiology, tinnitus, and cerebrovascular spasm. Human patients afflicted with a CNvD experience a single episode of the disorder, recurrent episodes, persistent episodes, or some combination of these patterns. An individual episode is designated an acute CNvD.

Many CNvDs, such as cerebral vascular accidents, reversible ischemic neurological defects, and transient ischemic attacks (TIA), are associated with functional cerebral ischemia. These are often nonhemorrhagic and of thrombotic, embolic, and vasospastic etiologies. Furthermore, intracranial vasospasm commonly afflicts patients who have experienced an acute cerebral ischemic event such as a stroke and is often problematic following thrombolytic therapy. Numerous symptoms occur during and after acute cerebral ischemic events. Indeed, neurovascular headaches have a vasomotor component to them, which may be responsible for certain or many of the symptoms experienced by patients who are afflicted with prolonged or recurrent neurovascular headaches such as migraines and cluster headaches.

It has been theorized that headaches of neurovascular etiology, such as migraines, for example, result from release of neurotransmitters by trigeminal nerves, which innervate cerebral blood vessels (Moskowitz et al., 1979, Lancet 2:883-885). When disturbed, the trigeminal ganglion is capable of antidromic release of excitatory and other neurotransmitters that initiate sterile inflammation (Demarin et al., 1994, Funct. Neurol. 9:235-245; Moskowitz, 1984, Ann. Neurol. 16:157-168; Moskowitz, 1993, Neurol. 43 (Suppl. 3):S16-S20). Studies of trigeminal stimulation, cerebral blood flow, and neuropeptides in animal models and in humans provide support for this theory (Goadsby et al., 1993, Ann. Neurol. 33:48-56; Goadsby et al., 1991, Headache, 31:365-370; Goadsby et al., 1990, Ann. Neurol. 28:183-187; Edvinsson et al., 1994, Cephalalgia 14:88-96). It has been postulated that changes in cerebral blood flow that are triggered by trigeminal stimulation are mediated by the sphenopalatine ganglion (hereinafter, the "SPG") Goadsby et al., 1987, Am J. Physiol. 22:R270-R274; Lambert et al. 1984, J. Neurosurg. 61:307-315; Walters et al., 986, Stroke 17:488-494; Suzuki et al., 1989 Neuroscience 30:595-604).

Another theory posits that nitric oxide is a causative molecule of headaches of neurovascular etiology (Olesen et al., 1995, Cephalalgia 15:94-100). Because the SPG and related postsynaptic and neurovascular structures contain many cells which express nitric oxide synthetase, the SPG mediates the changes in cerebral blood flow that are triggered by trigeminal stimulation, according to this model.

Regardless of whether a neurotransmitter, nitric oxide, both, or neither are the causative agent of headaches of neurovascular etiology, it is clear that the SPG and other dorsonasal nerve structures are key complex structures for targeting the treatment of headaches of neurovascular origin, such treatment including, but not being limited to the treatment of the pain associated with such headaches. Methods of treating headaches of neurovascular etiology which have been described in the prior art have not provided sustained and effective relief from acute neurovascular headache episodes.

Other researchers have observed meningeal inflammation in the vicinity of head pain associated with migraine (Pappagallo et al., April 1999 presentation, Meeting of the American Academy of Neurology, Toronto, Canada). Certain aspects of head pain associated with migraine (e.g., throbbing headache, nausea, and sensitivity to light and sound) are similar to head pain associated with meningitis. Single photon emission computerized tomography confirmed enhanced permeability of meningeal blood vessels in patients experiencing migraine, which is a common finding among meningitis patients. It is believed by the inventor that meningeal inflammation may be associated with stimulation of, or transmission by way of, the trigeminal nerve and related neuronal structures.

Migraine

Migraine is a disorder characterized by persistent headache, which may be severe, which may be associated with visual and gastrointestinal disturbances, and which may also be recurrent. In certain cases, visual changes (designated "aura" by some practitioners) or other symptoms precede the onset of a migraine. Such prodromal symptoms may be due to intracranial vasoconstriction. The precise etiology of migraine is unknown. Reported evidence suggests that a genetically transmitted functional disturbance of intra- and extracranial circulation may be involved. Regional alterations in cerebral blood flow attributable to intracranial arterial vasodilation are known to accompany headache associated with migraine. Some investigators have attributed head pain associated with a migraine to substances released as a result of or associated with dilation of scalp arteries during an acute migraine episode (e.g., Berkow et al., ed., 1992, The Merck Manual of Diagnosis and Therapy, Merck Research Laboratories, Rahway, N.J., pp. 1425-1426).

Prodromal symptoms of an acute migraine episode include, but are not limited to, depression, irritability, restlessness, anorexia, scintillating scotomas, visual changes such as perception of stars or zig-zag lines, paresthesias, and hemiparesis. These prodromal symptoms may disappear shortly before the migraine is manifested, or may persist until or after the onset of the migraine.

The head pain associated with migraine may be unilateral or generalized. Nausea, vomiting, and photophobia often accompany migraines. Symptoms generally follow a pattern in an individual patient, except that unilateral head pain may not always be on the same side. Patients afflicted with migraine may experience migraines with a frequency between daily and only once in several months. An untreated acute migraine episode may endure for a long period, such as hours or days. Approximately 17% of adult women and approximately 6% of adult men experience migraines each year (Stewart et al., 1994, Neurol. (Suppl. 4):S17-S23; Lipton et al., 1993 Neurology 43 (Suppl. 3):S6-S10; Osterhaus et al., 1992, PharmacoEconomics 2:67-76). Migraines may occur at any age, but usually begin between ages 10 and 30. Migraines often partially or completely remit after age 50. Frequently, a history of migraines may be ascertained in the genealogy of a patient afflicted with migraine.

Various nonspecific medical and surgical procedures have been recommended to decrease the frequency of recurrence of migraines. Such procedures include surgery, counseling, participation of the patient in biofeedback procedures, and administration of methysergide, propanolol, a calcium channel blocker such as verapamil, an ergotamine preparation such as dihydroergotamine, or a serotonin receptor agonist such as sumatriptan. Some procedures to decrease the frequency of recurrence of migraines may offer benefit to certain patients, but are not useful for alleviating the pain associated with an acute migraine episode once it has begun.

Treatments which have been recommended for the treatment of an acute migraine episode include administration of aspirin, codeine, a serotonin agonist such as sumatriptan, ergot, ergotamine, caffeine, a narcotic, butorphanol tartrate, meperidine, or a combination of these compounds. Administration of any combination of these compounds has not offered satisfactory or sustained relief from the pain or other symptoms associated with an acute migraine episode in many patients. Furthermore, numerous side effects have been reported to accompany administration of these compounds, including dizziness, nausea, somnolence, fatigue, chest pain, cardiac infarction, hypertension, hypertensive crisis, chest-, face-, and neck-hyperemia, gastrointestinal upset, sedation, drug dependence, and the like. In addition, certain of these compounds are contraindicated for numerous patients such as pregnant women, nursing women, patients using monoamine oxidase inhibitors, patients having a history of ischemic heart disease, ulcer, gastritis, kidney disease, liver disease, and other diseases.

Currently popular migraine treatments involve administration of a pharmaceutically active agent which interacts with a serotonin receptor on cerebral arterial surfaces (Goadsby, 1995, In: Migraine: Pharmacology and Genetics, Sandler et al., Eds., pp. 67-81; Cambridge et al., 1995, Brit. J. Pharmacol. 114:961-968; Ferrari et al., 1995, Euro. J. Neurol. 2:5-21). Serotonin receptor agonists include sumatriptan (IMITREX™, Glaxo Wellcome Inc., Research Triangle N.C.), zolmitriptan (ZOMIG™, Zeneca Pharmaceuticals, Wilmington, Del.), and rizatriptan (MAXALT™, Merck & Co., West Point, Pa.). Serotonin receptor agonists are believed to produce relief from an acute migraine episode by causing resumption of regulated cranial blood flow, thereby halting the acute migraine episode (Hamel et al., 1993 Mol. Pharmacol. 44:242-246). However, administration of serotonin receptor agonists is inefficient via intravenous, oral, and intrarectal gavage routes. These routes of administration result in systemic agonist distribution, which increases the availability of the agonist to hepatic tissue and to other sites where the agonists are metabolized. Furthermore, systemic distribution of one of an agonist results in distribution of the agonist to sites where the agonist produces undesirable side effects (Saper, 1997, Headache 37 (Suppl. 1):S1-S14). Therefore, it would be advantageous to administer an agent which does not require systemic delivery.

Intranasal administration of lidocaine for the relief of pain associated with migraines has been investigated in a non-controlled study by Kudrow et al. (1995, Headache, 35:79-82). In that study, many patients experienced no relief and were on migraine prophylactic medication. In a controlled study, Maizels and co-workers evaluated the effectiveness of intranasally-administered lidocaine, a shorter-acting local anesthetic, for treatment of acute migraine episodes (Maizels et al., 1996, J. Amer. Med. Assoc. 276:319-321). High concentrations of lidocaine administered intranasally decreased head pain within fifteen minutes in 55% of the patients so treated. However, significant pain and associated symptoms persisted in many of these patients following treatment. A significant number of patients required further treatment with other types of migraine medication to attain acceptable relief. Furthermore, the acute migraine episode frequently rebounded or relapsed early after treatment, usually within the first hour.

Cluster Headaches

A cluster headache comprises a headache which is characterized by recurrent episodes of unilateral excruciating pain, usually occurring on the same side of the head of a patient. These headaches are typically oculofrontal or oculotemporal, with occasional radiation to the upper jaw, and are described as being of a boring, non-throbbing nature. Associated with the head pain are one or more autonomic accompaniments, including conjunctival injection, nasal congestion, lacrimation, rhinorrhea, body temperature elevation, vasodilation on the same side as that on which the pain is experienced, and edema beneath the eye. A cluster headache is usually of short duration, persisting for between fifteen and ninety minutes, and tends to occur in clusters—typically a few times a day for a period of six to twelve weeks. Months or years may pass between the clusters of headaches. Because headaches which appear to be identical to spontaneous cluster headaches may be induced by subcutaneous injection of histamine diphosphate, cluster headaches are also known as histamine headaches. Headaches having sensory similarity to cluster headaches may also be induced by administration of nitroglycerin to a human patient, for example by sublingual administration of 0.4 milligrams of nitroglycerin.

Methods which have been investigated for treating cluster headaches include administration of methysergide, a vasoconstrictor, a corticosteroid, oxygen, indomethacin, and intranasal administration of cocaine, which is a toxic shorter-acting local anesthetic with pronounced central effects and a vasoconstrictor, or lidocaine, which is also a shorter-acting local anesthetic (Barre, 1982, Headache, 22:69-73; Kittrelle et al., 1985, Arch. Neurol. 42:496-498). These investigations highlight that shorter-acting local anesthetics were effective to abort pain associated with a single individual headache episode that is only one of several headache episodes comprising a cluster headache, sometimes referred to as a cluster period. Large amounts of drug and repeated dosings were required to achieve these results. However, no investigation was made by those investigators of the ability of these shorter-acting local anesthetics to provide relief from all, or even more than one, of the typically short-duration headaches associated with a single cluster headache period. Clinically, intranasal administration of lidocaine has proven to be disappointing and is not widely used, nor is it included in recognized cluster headache treatment protocols.

Tinnitus

More than 37 million Americans are afflicted with tinnitus. Tinnitus is a condition characterized by a ringing, buzzing, roaring, or clicking sound perceived by a patient, a person observing the patient, or both, which seems to originate from the ear of the patient. Objective tinnitus is characterized by noise originating from the ear of a patient which can be perceived by a person examining the patient, while noise associated with subjective tinnitus can be perceived only by the patient. There are currently no truly effective treatment options available for tinnitus, which has been associated with instances of suicide in patients afflicted therewith. Treatment methods which have been attempted include surgical decompression of the eighth nerve, use of specialized hearing aids which mask the tinnitus, and infusion of drugs directly into areas of the brain involved in auditory sensory processing. None of these treatment methods has proven routinely effective.

Intra- and Extracranial Vasospasm

Intra- and extracranial vasospasm, hereinafter referred to as "cerebrovascular spasm," results from contraction of smooth muscle tissue of a cerebral blood vessel. Cerebrovascular spasm interferes with cerebral blood supply and is associated with numerous symptoms, including muscle paralysis, visual changes, speech changes, and numerous ischemic symptoms of stroke. Vascular muscle tone is modulated by neural, humoral and local factors.

Disorders Manifested During or after and Associated with an Acute Ischemic Event Causes of acute ischemic events include occlusive (i.e., thrombotic or embolic) processes, as well as vasospastic and other physiological processes and disorders, following the onset of which the affected tissue is insufficiently supplied with oxygenated blood. Manifestations during or after such events include, for example, tissue damage or death, vasospasm, vasodilation, vasomotor instability, muscle weakness, dysphasia, dysphonia, cognitive impairment, autonomic imbalance, and the like. These disorders may be alleviated by increasing oxygenated blood supply to the ischemic tissue. Increased blood supply to ischemic cerebral tissue may be effected, for example, by inducing dilation of an occluded cerebral blood vessel. Further by way of example, such increased blood supply may be effected by dilation of cerebral blood vessels proximal to an occluded vessel by increasing the flow of oxygenated blood or by increasing the pressure gradient across the occlusion, thereby decreasing the amount of watershed ischemia, decreasing the amount of damaged cerebral tissue, and increasing the amount of cerebral tissue which may be salvaged. Furthermore, facilitating venous drainage, by venodilation, decreases venous back pressure and increases forward flow of oxygenated blood.

Prior art methods of treating such disorders exhibit serious limitations. Thrombolytic therapy, for instance, is known to be effective to decrease the severity of cerebral damage caused by certain occlusive strokes if the therapy is performed soon enough after the onset of the occlusion. However, cerebrovascular spasm frequently follows, and decreases the success of the procedure and adversely affects patient outcome. A method of reducing the severity of an acute cerebral ischemic event by increasing early blood flow to the ischemic area and decreasing vasospasm is needed.

Anatomy of the Nasal Cavity

The structures associated with the nasal cavity are described, for example, in Williams et al. (eds., 1980, Gray's Anatomy, 36th ed., W.B. Saunders Co., Philadelphia, 1062-1065), especially at FIGS. 3.78, 3.79, 3.80, 7.239, and 7.240 and the accompanying text. FIG. 1 herein is a diagram depicting the approximate location of the SPG in relation to the nasal cavity of a human.

The SPG is, in some texts, designated the "pterygopalatine ganglion." The position, origin, branches, and distribution of the SPG may be understood by examining FIGS. 7.177, 7.178, 7.179, and 7.181 and the accompanying text in Williams et al. (supra).

As the cited figures and text describe, the SPG is located below a region of epithelium in the posterior portion of the nasal cavity, inferior to and including the spheno-ethmoidal recess, and is therefore not readily accessible via the nostril.

Ropivacaine is a recently introduced amino amide local anesthetic that is commercially available as the S(levo)-enantiomer (Lee et al., 1989, Anesth. Analg. 69:736-738). Ropivacaine allows differential nerve block and exhibits intermediate distribution and clearance and a better systemic toxicity profile compared with other similar relatively long acting potent local anesthetics. In addition, ropivacaine also exhibits inherent vasoactive properties (deJong, 1995, Reg. Anesth. 20:474-481; Santos et al., 1990, Anesth. Analg. 70:262-266). Ropivacaine-HCl is commercially available as 0.25%, 0.5%, 0.75% and 1.0% (w/v) solution (NAROPIN™, Astra USA, Inc., Westborough, Mass.), and has been described, for example in international patent application publication number WO 85/00599.

Local anesthetics are known to block the generation and the conduction of nerve impulses, presumably by increasing the threshold for electrical excitation in the nerve, by slowing the propagation of nerve impulses, and by reducing the rate of rise of the action potential of the nerve. In general, the progression of anesthesia is related to the diameter, degree of myelination, and conduction frequency and velocity of affected nerve fibers. Generally, the order of loss of nerve function is as follows: (1) sympathetic and parasympathetic function, temperature and pain, and (2) touch, and, where applicable, (3) proprioception, and (4) skeletal muscle tone.

The rate of systemic absorption in a patient of a local anesthetic is dependent upon the total dose, the concentration, and the identity of the local anesthetic administered to the patient, the route of administration, the vascularity of the site of administration, and the presence or absence of vasoconstrictors such as epinephrine in the anesthetic composition. A dilute concentration of epinephrine (e.g., 1:200,000 or 5 micrograms per milliliter) usually reduces the rate of absorption and peak plasma concentration of the local anesthetic, sometimes prolonging the duration of the anesthetic effect.

The duration of the anesthetic effect at a given site of administration of a local anesthetic is dependent upon the total dose, the concentration, and the identity of the local anesthetic administered to the patient, the rate of systemic absorption, and often the presence or absence of a vasoconstricting or other agent in the anesthetic composition.

Systemic administration of a local anesthetic is not a practical method for delivery of the local anesthetic to provide lasting relief of headache pain in a human patient, due to known adverse reactions, occasionally including acute emergencies, associated therewith.

There remains a significant unmet need for effective methods of treating acute CNvDs such as persistent and recurrent headaches of neurovascular etiology, including migraines and cluster headaches. Particularly needed are compositions and methods which are effective for inhibiting an acute neurovascular headache episode.

Muscular Headaches

Muscular headaches are very common in the adult population. It is estimated that between about 3% and about 5% of patients who experience a muscular headache are afflicted with chronic muscular headaches, by which is meant that the muscular headache occurs more than fifteen days per month for a period of at least about six months. Analgesic addiction is a recognized problem in the treatment of patients afflicted with chronic muscular headaches.

Muscular headaches may be acute, as is the case for typical episodic tension headaches, which are related to contraction of muscles of the head and neck. Sustained contractions of skeletal muscles of the head, neck, face, and shoulders are associated with concurrent local chemical changes within skeletal muscle, and may give rise to pain. The pain may be localized or it may be referred, which means that the pain is perceived at a body location different than the location of muscle contraction. Muscle contraction headaches may also be chronic and associated with depression or with one or more other psychological problems. Muscle contraction headaches may also be associated with anatomic factors such as cervical arthritis, temporomandibular joint disorders, irritating lesions, pressure and mechanical stress, eye strain, or emotional stress or disorders.

Muscular headaches, including muscle contraction headaches and tension headaches, are recognized as the most common category of recurring head pain. In distinction from migraines, they are usually bilateral, often with occipital nuchal, temporal, or frontal predominance or with diffuse extension over the top of the cranium. The pain may be located in the back of the head and neck as well. Unlike migraine pain, the pain associated with a muscular headache is usually described as squeezing and vise-like in nature. Nausea, photophobia, and phonophobia are not generally associated with muscular headache episodes. The onset of a muscular headache episode is more gradual than the onset of a migraine or cluster headache episode, and muscular headache episodes are not generally associated with auras or prodromal symptoms. The onset of muscular headache episodes does not appear to be associated with physical activity by the patient. Once established, a muscular headache episode may persist, perhaps with minimal fluctuations in intensity, for weeks or months. Muscular headache is recognized as being present all day, day after day.

Although patients afflicted with migraine may be awaked from sleep, patients afflicted with a chronic muscular headache generally sleep undisturbed and perceive development or intensification of the headache soon after waking. About a third of patients afflicted with a muscular headache exhibit symptoms of depression. Migraine headaches may be complicated by tension headaches which persist and arouse fears of mass lesions, thereby leading to the performance of unnecessary diagnostic workups in many patients.

Muscular headaches are recognized as being a distinct class of headaches, distinguishable from headaches such as migraines or cluster headaches.

Muscular headaches are, in part, related to sustained contraction of the skeletal muscles of the scalp, face, neck, and shoulders. Sustained muscle contraction is related to local pathology, central influences, and multisystem modulation, and involves gamma efferent neuronal muscle spindle activation. Related monosynaptic conduction through the ventral horn augments both efferent neuronal discharge and muscle contraction. A cycle of pain, muscle spasm, local chemical changes, neural excitability, skeletal muscle blood vessel compression or spasm, and anxiety ensues. All types of persistent headaches lead to sustained cranial muscle contraction, but pain resulting from this type of sustained contraction is typified by an aching sensation, rather than by the characteristic squeezing pain associated with muscular headaches. Sometimes, surface electromyograph recordings of the craniocervical muscles show no evidence of persistent contraction. It is therefore widely suspected that muscular headaches are not caused solely by sustained cranial muscle contraction.

Generally, the pain associated with a muscular headache episode is mild to moderate in severity, although the pain becomes severe in many patients. Relaxation, massage, and common analgesic medications such as aspirin and acetaminophen are often effective to alleviate mild muscular headache pain. Codeine or other narcotic preparations, tranquilizers, and antidepressants are sometimes administered to patients experiencing more severe muscular headache pain. Unfortunately, many of these patients develop physical dependence on these agents and must be followed closely because of a significant incidence of addiction.

Nonetheless, the musculature of the head, neck, jaw, or upper back is tense and tender in many or most patients afflicted with a muscular headache, and one or more trigger points, or muscle knots, are often present. Cervical spine arthritis and temporomandibular joint disorders may contribute to the development of a muscular headache.

Treatments which have been recommended for the treatment of muscular headaches include reassurance and psychological support, massage of the head and neck, application of hot and cold packs, transcutaneous electrical neural stimulation, physical support (e.g., use of orthopedic pillows and the like), administration of aspirin compounds, acetaminophen compounds, non-steroidal anti-inflammatory drugs, tricyclic antidepressants, narcotic analgesics, oral muscle relaxants, with or without tranquilizers, muscle relaxants, and other analgesic compounds. These treatments are generally effective for alleviating mild- to moderate-intensity acute muscular headaches.

Some patients afflicted with either severe or chronic muscular headaches sometimes experience relief from their acute symptoms using these known treatments. However, many do not. Furthermore, over time, many patients who initially respond to one or more of these therapies become less responsive to these therapies, possibly because they develop a tolerance to known medications, or because the disease process progresses or increases. Additionally, symptoms may be influenced by psychological factors which may remain constant or worsen. The side effects which accompany administration of known medications are significant and may become more severe over time.

There remains a significant unmet need for effective compositions and methods of treating muscular headaches, including inhibiting muscle contraction headaches and tension headaches. The present invention provides compositions and methods which satisfy this need.

Systemic Delivery of a Pharmaceutically Active Agent

Numerous pharmaceutically active agents are useful when delivered systemically to a human patient. Systemic delivery of such agents can sometimes be effected by oral administration of a composition comprising the agent. However, many pharmaceutically active agents are degraded by, or otherwise react with acids, proteins, or other agents located in, the human gastrointestinal tract or the human liver or circulatory system, with the result that the agent loses its pharmaceutical usefulness. For this reason, many pharmaceutically active agents may not practically be administered by an oral route to achieve systemic delivery of the agent. In addition, gastrointestinal absorption of an orally administered medication may be impaired in a distressed patient, such as a patient experiencing a migraine or any severe headache.

Pharmaceutically active agents intended for systemic delivery to a human may be administered via an intravenous route using well known methods. However, such methods cause discomfort to the patient and often can be performed only in conjunction with frequent or continuous supervision by a medical professional.

Methods of topically administering compositions to a human tissue to achieve systemic delivery of a pharmaceutically active agent which is a component of the composition are known, including the use of transdermal or transmucosal pastes, cremes, liquids, solids and semisolids impregnated with the composition, and the like. Systemic delivery of a pharmaceutically active agent effected by topical administration methods are limited by the ability of the agent to diffuse through the tissue to which the composition is applied to reach blood vessels where the agent is absorbed and taken up for systemic delivery.

A significant, unmet need remains for compositions and methods which can be used to systemically deliver or to enhance systemic delivery of a pharmaceutically active agent to a human and which overcome the limitations of known systemic delivery compositions and methods.

The present invention provides compositions and methods which satisfy the needs described herein.

BRIEF DESCRIPTION OF THE SEVERAL VIEWS OF THE DRAWINGS

FIG. 4, comprising FIGS. 4A through 4N, is a series of drawings which depict dorsonasal delivery apparatus of the invention. FIG. 4A is a diagram of a sagittal section through the right nostril and the right portion of the nasal cavity of a human, illustrating the approximate placement of the body 100 of the dorsonasal delivery apparatus described herein. Abbreviations used in this Figure include apex A of the nasal cavity, nostril N, superior concha SC, middle concha MC, and inferior concha IC. FIGS. 4D through 4I illustrate various embodiments of the dorsonasal delivery device of the invention, as described herein. Alternative orientations of the device, before (solid) and after (dashed) inflation of the balloon 110 thereof are shown in FIG. 4G. FIGS. 4L, 4M, and 4N are other embodiments of the dorsonasal delivery device described herein. In FIG. 4M, the position of an absorbent portion 110 is shown alternatively in an engorged, extended position (solid) and a compressed position (dashed). In FIG. 4N, the absorbent portion 110 is tapered in order to facilitate withdrawal from the nasal cavity with minimal trauma.

FIG. 7, comprising

BRIEF SUMMARY OF THE INVENTION

Figure 1:
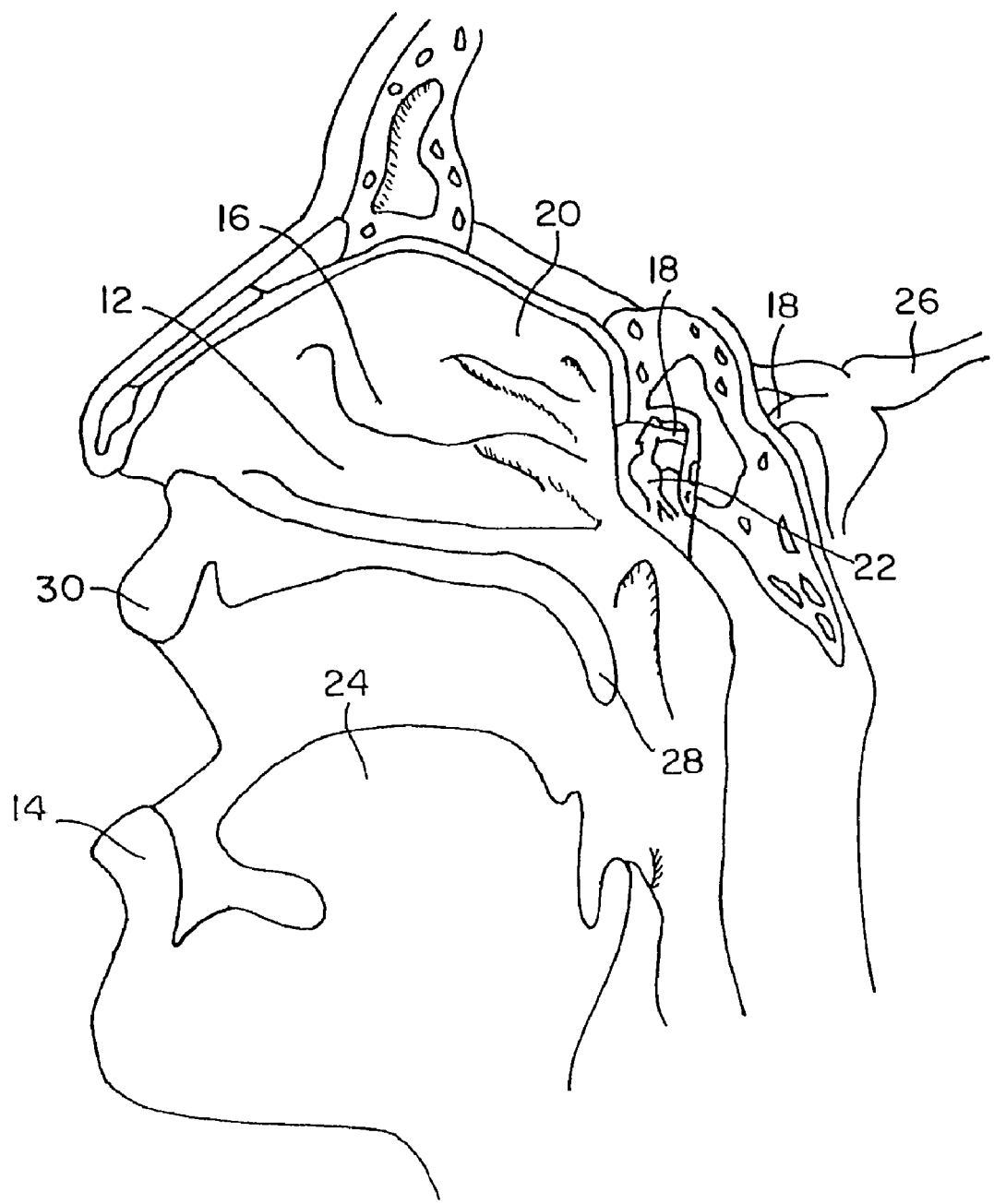
FIG. 1 is a diagram depicting a sagittal section of a portion of a human head, the section being just to the right of the nasal septum. A section is cut away at the posterior portion of the nasal cavity to reveal the approximate placement of the sphenopalatine ganglion. Indicia used in this Figure include 12 inferior concha, 14 lower lip, 16 middle concha, 18 maxillary nerve, 20 superior concha, 22 sphenopalatine ganglion, 24 tongue, 26 trigeminal nerve, 28 uvula, and 30 upper lip.
Figure 2:
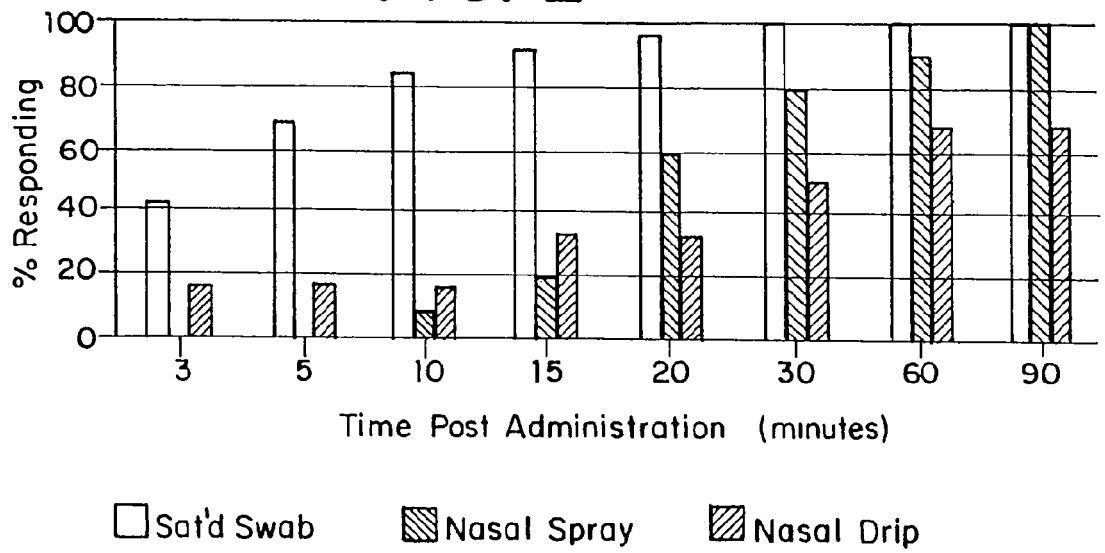
FIG. 2 is a bar graph which depicts the percentage of patients who exhibited at least 50% reduction in pain intensity following dorsonasal administration of ropivacaine using the intranasal spray method described herein ("Nasal spray"), using the intranasal drip method described herein ("Nasal drip"), or using the intranasal cotton swab method described herein ("Sat'd Swab").

One aspect of the invention relates to a method of inhibiting a cerebral neurovascular disorder (CNvD) in a human patient. This method comprises intranasally administering a long-acting local anesthetic pharmaceutical composition to the patient in an amount effective to inhibit the CNvD. The CNvD may, for example, be selected from the group consisting of tinnitus, cerebrovascular spasm, seizure, a disorder manifested during or after and associated with an acute ischemic event, and a neurovascular headache. Preferably, the CNvD is a migraine, such as an acute migraine episode.

According to this method, the long-acting local anesthetic pharmaceutical composition comprises a pharmaceutically acceptable carrier, at least one local anesthetic ingredient selected from the group consisting of a long-acting local anesthetic, a persistent local anesthetic, and a sustained release formulation of a local anesthetic, and may further comprise a compound selected from the group consisting of an anti-epileptic, phenyloin sodium, a serotonin receptor agonist, a serotonin subclass 5HT1F receptor agonist, LY334,370, a sesquiterpene lactone, parthanolide, Tanacetum parthenium, and an extract of Tanacetum parthenium.

The invention includes a method of inhibiting cephalic inflammation in a human patient. This method comprises anesthetizing a nerve structure associated with the disorder in the patient for a period effective to inhibit the inflammation (e.g., at least about one or two hours). The nerve structure can be anesthetized by any method known in the art or described herein. For example, the nerve structure can be anesthetized by performing acupuncture upon the nerve structure, applying an electrical potential to the nerve structure, applying electromagnetic radiation to the nerve structure, or administering a long-acting local anesthetic pharmaceutical composition to the nerve structure. In one embodiment, cephalic inflammation is inhibited in the patient by energizing a dorsonasally implanted electronic neural stimulator.

The invention also relates to an intranasal drug delivery device or applicator. This device comprises a body having a shape which conforms to the shape of the nasal cavity of a human. The body has a proximal end and a distal portion having a distal end. The distal portion of the body can be urged through a nostril of the human into the apex of the nasal cavity without injuring the human. The distal end of the body may be rounded. The body may, for example, be substantially rigid, be flexible, or comprise a flexible portion.

Optionally, a lumen extends longitudinally within the body of the intranasal drug delivery device or applicator of the invention. The lumen extends from the proximal end thereof to an outlet port at the exterior surface of the body, such as an outlet port on the distal portion of the body. The lumen may extend to a plurality of outlet ports, or a plurality of lumens may extend longitudinally within the body from the proximal end thereof to a separate outlet port. Preferably, at least one outlet port is situated on the distal portion of the body in an orientation such that when the distal portion of the body is in the apex of the nasal cavity, the outlet port faces a posterior or superior portion of the nasal cavity, such as the sphenoethmoidal recess or the superior epithelial surface of the nasal cavity, so that directed intranasal delivery of the drug can be achieved.

The body of the intranasal drug delivery device of the invention may, for example, have an elongated shape selected from the group consisting of an angled shape and a curved shape. The longitudinal axis of the body at the distal end thereof forms an angle of about 90 to about 170 degrees (preferably about 110 to about 160, and more preferably about 120 to about 150 degrees) with the longitudinal axis of the body at the proximal end thereof.

In one embodiment of the intranasal drug delivery device of the invention, the device further comprises an extendable instrument situated with a lumen thereof. The extendable instrument is extendable through the outlet port of the lumen. The extendible instrument may, for example, be selected from the group consisting of a swab, a rosette, an inflatable balloon, and a needle. The needle may be hollow, have a outlet in its distal end, extend through the lumen, or have a proximal end connectable to a reservoir, such as one selected from the group consisting of a compressible reservoir, a deformable bulb, and a syringe.

In another embodiment of the intranasal drug delivery device of the invention, the body of the device has an absorbent portion on the distal portion thereof. In a separate embodiment, the device has a lumen which communicates at the proximal end of the body with the interior of a reservoir containing a pharmaceutical composition, such as one which comprises a long-acting local anesthetic. The pharmaceutical composition may, for example, be delivered in a form selected from the group consisting of a liquid, a gel, a foam, a mousse, a powder, a dispersed powder, an atomized liquid, an aerosol, and a liposomal preparation.

The invention also relates to a method of intranasally (e.g., dorsonasally) administering a composition to a human patient. This method comprises inserting an intranasal drug delivery device of the invention into a nostril of the patient, urging the device through the nostril such that the distal end of the body is in the apex of the nasal cavity, and contacting a portion of the nasal epithelium (e.g., a portion overlying the SPG) with the composition on the portion of the exterior surface.

The invention further relates to another method of intranasally administering a composition to a human patient. This method comprises inserting an intranasal drug delivery device of the invention having a lumen extending therethrough into a nostril of the patient, urging the device through the nostril such that the distal portion of the body is in the apex of the nasal cavity, and providing the composition to a portion of the nasal epithelium by way of the lumen.

The invention relates to still another method of intranasally administering a composition to a human patient. This method comprises inserting an intranasal drug delivery device of the invention having a lumen extending therethrough into a nostril of the patient, urging the device through the nostril such that the distal portion of the body is in the apex of the nasal cavity, urging an elongate instrument comprising the composition through the lumen (e.g., into the apex of the nasal cavity). The elongate instrument may, for example, be selected from the group consisting of an extendable instrument comprising the composition, a swab impregnated with the composition, a rosette impregnated with the composition, a needle coated with the composition, an inflatable instrument comprising the composition, a balloon coated with the composition, a balloon impregnated with the composition, a hollow instrument having a lumen for providing the composition, and a hollow needle having a lumen for providing the composition, whereby the composition is provided to a portion of the nasal epithelium.

The invention also relates to an anatomically adapted intranasal (e.g., dorsonasal) delivery nozzle for intranasally administering a composition to a human patient. The nozzle comprises a body having a delivery lumen extending therethrough from a proximal end of the body to an outlet port at a distal portion of the body and an exterior portion. The exterior portion has (i) a flattened portion situated peripherally between the proximal end and the distal portion for seating the nozzle against the nasal septum of the patient, (ii) an anterior portion situated peripherally between the proximal end and the distal portion for seating the nozzle against a portion of the external nasal cartilage of the patient, and (iii) an indented portion situated peripherally between the proximal end and the distal portion for seating the nozzle against a nasal concha of the patient. When the nozzle is seated, the outlet port is situated within the nasal cavity of the patient such that the axis extending through the discharge port is offset from the apex of the nasal cavity by no more than about 30 degrees, and preferably by no more than about 15 degrees. In an alternate embodiment, the body comprises a distal seating portion for seating the nozzle against the superior surface of the nasal cavity.

The body of the nozzle of the invention may, for example, be deformable. For example, the body may be deformable at a certain condition, but less deformable at a different condition. The nozzle may thus be adapted to the nasal cavity of the patient at the certain condition and thereafter used at the different condition. By way of example, the body may be adapted to the nasal cavity of the patient at a temperature at which the body is deformable, and thereafter used at a temperature at which the body is less deformable.

The invention also relates to a method of intranasally (e.g., dorsonasally) administering a composition to a human patient. This method comprises seating within the nasal cavity of the patient an anatomically adapted intranasal delivery nozzle of the invention and thereafter providing the composition to the delivery lumen of the nozzle. The composition is thereby intranasally administered to the patient.

The invention further includes an improved manually pressure-actuated drug delivery device. The device comprises a body having an intranostril applicator for insertion into a nostril of a patient, a drug container, and a manually pressure-actuated actuator fixed to at least one of the applicator and the container and actuatably fluidly connecting the applicator and the container. Drug from the container is provided to the applicator upon application of pressure by the patient to the connector. The improvement comprises the actuator being positioned with respect to the intranostril applicator in such a way that actuating pressure must be applied to the actuator in a direction which is not co-linear with the axis of the nostril into which the applicator is inserted. Alternatively, the actuator may be positioned with respect to the intranostril applicator in such a way that actuating pressure must be applied to the actuator in a direction which is not parallel to the axis of the nostril. As another alternative embodiment, the actuator may be positioned in such a way that actuating pressure must be applied to the actuator in a direction which is offset by at least about 30 degrees (preferably by at least about 45 degrees, at least about 60 degrees, or about 90 degrees) from the axis of the nostril.

The invention further includes a systemic drug delivery device. This device comprises a body having a shape which conforms to the shape of the nasal cavity of a human. The body has a proximal end and a distal portion which can be urged through a nostril of the human into the apex of the nasal cavity without injuring the human. The body also has an applicator portion in the form of at least one of a portion on which the drug is present, a portion to which the drug may be supplied, and a lumen through which the drug may be delivered. The applicator portion is adapted for location in close anatomic proximity to a highly vascularized portion of the nasal epithelium when the distal portion of the body is in the apex of the nasal cavity.

The invention still further includes an anatomically adapted intranasal delivery nozzle for systemically administering a composition to a human patient. This nozzle comprises a body having a delivery lumen extending therethrough from a proximal end of the body to an outlet port, and an exterior portion. The exterior portion has (i) a flattened portion situated peripherally between the proximal end and the distal portion for seating the nozzle against the nasal septum of the patient, (ii) an anterior portion situated peripherally between the proximal end and the distal portion for seating the nozzle against a portion of the external nasal cartilage of the patient, and (iii) an indented portion situated peripherally between the proximal end and the distal portion for seating the nozzle against a nasal concha of the patient. When the nozzle is seated, the outlet port is situated within the nasal cavity of the patient such that the axis extending from the discharge port extends through a highly vascularized portion of the nasal epithelium.

The invention also includes a method of inhibiting a cerebral neurovascular disorder in a human patient. This method comprises energizing a dorsonasally implanted electronic neural stimulator.

The invention also includes local anesthetic compound having the chemical structure of formula (IV), wherein R is ethyl, phenyl, or $C_5$-$C_8$ straight- or branched-chain alkyl, and R' is 2,6-dimethylphenyl, thiophene, or 2,5-dimethylthiophene, and wherein R" and R'" are selected such that either (i) each of R" and R'" is a straight-chain alkyl wherein R" and R'" have a total of 4 to 6 carbon atoms, or (ii) R" and R'" together form a heteroalkyl ring having a total of 5 to 7 carbon atoms and a nitrogen atom

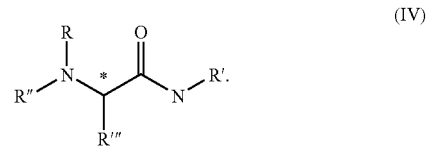

(IV)

For example, the local anesthetic compound may have the structure of formula (III)

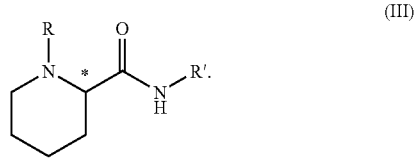

(III)

In the structures of formulas (III) and (IV), the carbon atom indicated by the asterisk is a chiral center.

The invention also relates to a kit comprising the long-acting local anesthetic pharmaceutical composition of the invention and an intranasal drug delivery device or applicator for administering the composition to the patient. For example, the device or applicator may be one of those described herein, and can be adapted for dorsonasal delivery. The kit may also comprise instructional material which describes intranasal or dorsonasal administration of the composition to a human or another animal.

DETAILED DESCRIPTION OF THE INVENTION

The first aspect of the present invention is based on the discovery that intranasal administration of a long-acting local anesthetic pharmaceutical composition to a human patient experiencing a cerebral neurovascular disorder (CNvD) inhibits the CNvD or a symptom of the CNvD. The invention also relates to the discovery that anesthesia of a dorsonasal nerve structure (DnNS) in a human patient experiencing a CNvD inhibits the CNvD or a symptom of the CNvD if the anesthesia persists for a period of at least about an hour, and preferably for a period of at least about two hours.

Local anesthetics are known to provide analgesia to a body surface to which they are applied. However, such analgesia persists only for a period of time which is characteristic of the particular local anesthetic used and the site anesthetized. Local anesthetics may be roughly divided into classes based on the duration of analgesia provided to a patient following topical administration.

It is known that intranasal administration of a relatively shorter-acting local anesthetics such as lidocaine or cocaine decreases head pain for a period approximately equal to the duration of analgesia which is characteristic of such shorter-acting local anesthetics. Lidocaine and cocaine each exhibit a duration of action shorter than about one hour when intranasally administered.

What was not known, and what represents a surprising discovery, is that intranasal, and preferably dorsonasal, administration of a local anesthetic preparation which either relieves a symptom of the CNvD for at least about one hour or exhibits a duration of anesthesia equal to at least about one hour is effective both to relieve head pain beyond the period of expected anesthesia and, more importantly, to inhibit the CNvD, such that symptoms of the CNvD, including head pain, do not rebound following the period of anesthesia, or even for many hours, days, or weeks thereafter. Rebound remains a major shortcoming of prior art treatments. It has furthermore been discovered that cephalic inflammation, a condition associated with CNvDs (as a symptom, as a cause, or both) can be inhibited by interrupting or interfering with neural transmission of neural impulses through one or more DnNSs, such as by intranasally (and preferably dorsonasally) administering a long-acting local anesthetic pharmaceutical composition to the patient, by applying an electrical potential to the DnNS, or by any other anesthetic method described herein.

Prior art intranasal delivery devices (e.g., intra-nostril squeeze-type mist dispensers) typically deliver compositions to only the distal portions of the nose, such as to portions of the nasal mucosa within a few centimeters of the nares. Devices disclosed herein can be used to direct compositions to other portions of the nasal cavity, including to portions of the nasal epithelium that contact or overlie important physiological structures, such as nerves, other nervous tissues, and blood and lymphatic vessels in the superior and dorsal portions of the nasal cavity. The devices can also be used to target particular structures.

DEFINITIONS

As used herein, the term "cerebral neurovascular disorder" (CNvD) means a disorder which is characterized by one or more disturbances in the normal functioning of at least one component of the cerebral vascular or cerebral nervous system in a human. CNvDs which have been characterized include migraine, cluster headaches, other headaches of neurovascular etiology, tinnitus, and cerebrovascular spasm. An "acute" CNvD means an individual episode of a CNvD. Thus, an acute CNvD includes, but is not limited to, an acute neurovascular headache episode, a single episode of tinnitus, a single episode of cerebrovascular spasm, and a set of symptoms or a disorder manifested during or after and associated with an acute ischemic event such as a single cerebrovascular occlusion or a stroke.

As used herein, cephalic inflammation includes, but is not limited to, cerebral inflammation, meningeal inflammation, and other varieties of extracranial and intracranial inflammation.

As used herein, a CNvD or an acute CNvD or a muscular headache is "inhibited" if at least one symptom of an episode of the CNvD or the muscular headache is alleviated, terminated, or prevented. As used herein, a CNvD or muscular headache is also "inhibited" if the frequency of recurrence, the severity, or both, of acute CNvD or muscular headache is reduced.

As used herein, the term "muscular headache" means head, neck, face, periocular, scalp, or upper back pain associated with contraction of muscles of the head, neck, jaw, or upper back of a patient. The head pain may be experienced in or around a muscle, or it may be referred to a part of the head or upper back distinct from the site of the affected muscle. It is understood that the term "muscular headache" includes both acute and chronic episodes of head pain. By way of example, muscular headaches include muscle contraction headaches and tension headaches.

As used herein, a CNvD or a muscular headache is "terminated" if at least one symptom of the CNvD or muscular headache ceases in a patient and the patient does not experience the symptom for at least several hours or, preferably, for at least about one day.

As used herein, a "recurring" CNvD is a CNvD which is experienced by a patient more than once in a six-month period As used herein, the term "acute ischemic event" refers to a single episode experienced by a human patient wherein a tissue of the patient is insufficiently supplied with oxygen. Acute ischemic events include, for example, ischemia associated with a stroke, ischemia associated with vasospasm, and ischemia associated with an acute neurovascular headache episode.

As used herein, the term "neurovascular headache" means a headache of neurovascular etiology associated with a disease, disorder, or imbalance of the nervous or vascular systems in a human. Headaches of neurovascular etiology include, but are not limited to, migraines and cluster headaches.

As used herein, the term "acute neurovascular headache episode" means a single neurovascular muscular headache which either has a duration greater than about one hour or recurs more than once in a one-day period in a human patient. Examples of acute neurovascular headache episodes include, but are not limited to, a single persistent neurovascular headache, an acute migraine episode, each of the individual headache episodes associated with a recurrent neurovascular headache, and each of the individual headache episodes associated with a cluster headache.

As used herein, the term "acute muscular headache episode" means a single muscular headache. Examples of acute neurovascular headache episodes include, but are not limited to, a single muscle contraction headache and a single tension headache.

As used herein, the term "chronic muscular headache" means a muscular headache muscular which is experienced by a human patient more than fifteen days per month for a period of at least about six months.

As used herein, the term "persistent neurovascular headache" means a headache of neurovascular etiology which persists for a period longer than about one hour.

As used herein, the term "recurrent neurovascular headache" means a headache of neurovascular etiology which is experienced by a human patient more than once in a one-day period.

As used herein, the term "rebound" of a CNvD means experience by a patient of one or more symptoms of the CNvD following a period during which the patient did not experience the one or more symptoms, the symptom-free period having been preceded by an earlier period during which the patient experienced one or more symptoms of the CNvD. It is understood that it is not always possible to discern whether a patient who did not experience the one or more symptoms for a period is afflicted with the same episode or with a separate episode of the same CNvD. Thus, the term is inclusive of both situations.

As used herein, the term "migraine" means a human disorder characterized by at least one persistent neurovascular headache episode.

As used herein, the term "an acute migraine episode" means an individual headache experienced by a human patient afflicted with migraine.

As used herein, the term "cluster headache" means a human disorder characterized by recurrent neurovascular headaches of short duration.

As used herein, the term "individual headache episode associated with a cluster headache" means a single neurovascular headache experienced by a human patient afflicted with cluster headache.

As used herein, the term "prodromal headache symptom" means a symptom which is experienced by a patient and which is associated with the onset or indicates the imminent onset of an acute neurovascular headache episode.

As used herein, a "nerve structure" means a nerve, a plurality of nerves located in close anatomic proximity to one another, or a ganglion.

As used herein, a nerve structure is "associated with" a CNvD if, when the nerve structure is anesthetized in a human patient afflicted with the disorder, the patient experiences relief from at least one symptom of the CNvD.

As used herein, a "dorsonasal nerve structure" (DnNS) means the sphenopalatine ganglion (SPG) or a nerve structure located in close anatomic proximity to the SPG.

As used herein, a first nerve structure is located in "close anatomic proximity" to a second nerve structure if the second nerve structure is anesthetized following anesthesia of the first nerve structure effected by administration of a local anesthetic to a tissue which comprises or overlies the first nerve structure. It is believed that dorsonasal administration of a local anesthetic anesthetizes at least one, and perhaps all, of the SPG, the cavernous sinus ganglion, the carotid sinus ganglion, numerous branches of the maxillary nerve, the ethmoidal nerve, the ethmoidal ganglion, and the vidian nerve. Thus, by way of example, each of the cavernous sinus ganglion, the carotid sinus ganglion, numerous branches of the maxillary nerve, the ethmoidal nerve, the ethmoidal ganglion, and the vidian nerve is located in close anatomic proximity to the SPG, and thus each is a DnNS.

As used herein, an "intranasal nerve structure" ("InNS") is a nerve structure that contacts the nasal epithelium or lies in sufficiently close proximity to the nasal epithelium that a compound applied to the epithelium is able to diffuse to or otherwise gain access to the nerve structure.

As used herein, an "intranasal blood vessel" ("InBV") is a blood or lymphatic vessel that contacts the nasal epithelium or lies in sufficiently close proximity to the nasal epithelium that a compound applied to the epithelium is able to diffuse to or otherwise gain access to the blood vessel.

As used herein, a nerve structure is "anesthetized" when the capacity of the ganglion to generate or conduct nerve impulses is significantly impaired, relative to the capacity of the nerve structure to generate or conduct nerve impulses in the absence of intervention, such as by administration of a local anesthetic. Anesthesia of the SPG effected by administration of a local anesthetic, for example, interrupts the functioning normally associated with the SPG and with other DnNSs. It is understood that anesthesia of a nerve structure may be achieved not only using a local anesthetic, but also by any anesthetic method as set forth herein.

As used herein, the capacity of a DnNS to generate or conduct nerve impulses is "significantly impaired" when that capacity is reduced by an amount sufficient to relieve the pain associated with a headache of neurovascular origin in a patient afflicted with such a headache.

As used herein, the term "shorter-acting local anesthetic" means a local anesthetic which, when intranasally administered to a human patient experiencing a CNvD or a muscular headache, relieves at least one symptom of the CNvD or muscular headache for a period of less than about one hour. By way of example, lidocaine and cocaine are shorter-acting local anesthetics.

As used herein, the term "long-acting local anesthetic" means a local anesthetic which, when intranasally administered to a human patient experiencing a CNvD or a muscular headache, reliably or consistently relieves at least one symptom of the CNvD or muscular headache for a period of at least about one hour. By way of non-limiting examples, bupivacaine and ropivacaine are long-acting local anesthetics.

As used herein, the term "persistent local anesthetic" means a local anesthetic which, when intranasally administered to a human patient experiencing a CNvD or a muscular headache, relieves at least one symptom of the CNvD or muscular headache for a period of at least about two hours.

As used herein, the terms "vasoconstrictor" and "vasoconstricting agent" are used interchangeably to mean an agent which induces diminution of the lumenal caliber of a blood vessel. The agent may be a chemical compound or a stimulus applied to a motor neuron which causes vasoconstriction. Hence, administration of a vasoconstrictor may comprise administration of a chemical compound, application of such a stimulus, or both. Vasoconstrictors include, but are not limited to, epinephrine, norepinephrine, and phenylephrine.

As used herein, the terms "vasodilator" and "vasodilating agent" are used interchangeably to mean an agent which induces an increase in the lumenal caliber of a blood vessel.

As used herein, the term "intranasal administration" of a composition and grammatical forms thereof mean delivery of the composition to any portion of the nasal epithelium.

As used herein, the term "dorsonasal administration" of a composition and grammatical forms thereof mean delivery of the composition to a tissue, fluid, or surface of a human, whereby a component of the composition is provided to a DnNS or to a tissue overlying a DnNS. Dorsonasal administration may be accomplished, for example, by topical administration of the composition to the region of the nasal epithelium overlying the SPG or to the surface of the nasal epithelium near the region of the nasal epithelium overlying the SPG, whereby a component of the composition is capable of diffusing through any tissue or fluid which may be interposed between the surface and the SPG. Such administration may also be accomplished, for example, by injecting the composition directly into the SPG or by injecting the composition into or otherwise administering the composition to a tissue or fluid near the SPG, whereby a component of the composition is capable of diffusing through any tissue or fluid which may be interposed between the site of injection or administration and the SPG.

As used herein, the term "the region of the nasal epithelium overlying the SPG" means the area of the nasal epithelium having a geometrical relationship with the SPG whereby an imaginary line approximately perpendicular to the surface of the epithelium and extending from the surface of the epithelium in the direction of the basement membrane of the epithelium passes through a DnNS.

As used herein, the term "the surface of the nasal epithelium near the region of the nasal epithelium overlying the SPG" means a portion of the surface of the nasal epithelium which is continuous with and sufficiently geometrically close to the region of the nasal epithelium overlying the SPG such that a compound applied anywhere on this surface is able to diffuse to the SPG. It is understood that the boundaries of the surface are dependent upon the diffusivity of the compound in the epithelium and in any tissue or fluid situated between the epithelium and the SPG. Thus, the area of this surface will be greater for a compound having high diffusivity than the area corresponding to a compound having a lower diffusivity. It is further understood that, where the compound has a half-life in vivo, the boundaries of "the surface of the nasal epithelium near the region of the epithelium overlying the SPG" are dependent upon the half-life of the compound. Thus, the area of this surface will be greater for a compound having a longer half-life than the area corresponding to a compound having a shorter half-life.

In the case of a compound having a diffusivity and a half-life comparable to that of ropivacaine, "the surface of the nasal epithelium near the region of the epithelium overlying the SPG" includes, but is not limited to, the surface of the region of the nasal epithelium overlying the SPG and the surface of the nasal epithelium continuous with and located within about three centimeters of that region. Preferably, such a compound is delivered to the surface of the nasal epithelium within about two centimeters of that region, and even more preferably to the surface of the nasal epithelium within about one centimeter of that region. Most preferably, the compound is delivered to the surface of the nasal epithelium overlying the SPG. It is understood that, in the case of a local anesthetic such as ropivacaine, the surface includes the epithelial surface covering the dorsal surface of the nasal cavity extending caudally from approximately the superior extent of the sphenoethmoidal recess to approximately the inferior boundary of the nasopharynx and extending laterally between the region of the surface covering the perpendicular plate of the right palatine bone and the region of the surface covering the perpendicular plate of the ethmoid bone and between the region of the surface covering the perpendicular plate of the left palatine bone and the region of the surface covering the perpendicular plate of the ethmoid bone.

As used herein, the "superior portion" of the nasal epithelium means one or more areas of the nasal epithelium situated on or above the superior face of the superior conchae.

As used herein, the term "non-intravenous administration" of a composition means administration of the composition by any means other than injection or infusion of the composition directly into the bloodstream of a human patient.

As used herein, the term "long-acting local anesthetic pharmaceutical composition" means a chemical composition comprising a pharmaceutically acceptable carrier and at least one local anesthetic ingredient selected from the group consisting of a long-acting local anesthetic, a persistent local anesthetic, and a sustained release formulation of a local anesthetic, wherein administration of the composition to a patient experiencing a CNvD or muscular headache inhibits the CNvD or muscular headache.

As used herein, the term "pharmaceutically acceptable carrier" means a chemical composition with which a local anesthetic may be combined and which, following the combination, can be used to administer the local anesthetic to a human patient without significantly adversely affecting the patient.

As used herein, "a sustained release formulation of a local anesthetic" is a pharmaceutical composition comprising a local anesthetic, wherein upon administration of the composition to a tissue of a human patient, the local anesthetic is delivered to the tissue on a continuous or semi-continuous basis for a period of hours, days, or weeks. Methods of making and using sustained release formulations of local anesthetics are well within the skill of one of ordinary skill in the art of pharmacology. In addition, inclusion of a vasoconstrictor in the composition may prolong the duration of the anesthetic effect.

As used herein, a composition is "formulated for intranasal delivery" if the composition is susceptible of intranasal administration to a human and if the composition is not significantly injurious to the tissues lining the nasal cavity of a human.

As used herein, the term "pharmaceutically active agent" means a composition which, when administered to a human patient, has a biochemical or physiological effect on the patient.

As used herein, "instructional material" includes a publication, a sound, video, or other recording, a diagram, or any other medium of expression which can be used to communicate the usefulness of the composition of the invention for inhibiting a CNvD or a muscular headache. The instructional material of the kit of the invention may, for example, be separate from, included with, or affixed to a container which contains the composition of the invention or be shipped together with a container which contains the composition. The instructional material may, for example, describe an appropriate dose of the composition of the invention or directions for using an applicator included in the kit to intranasally or dorsonasally administer a local anesthetic.

As used herein, a "eutectic mixture" is a mixture comprising at least one local anesthetic and at least one eutectic ingredient.

As used herein, a "eutectic ingredient" is a chemical compound which, when mixed with a local anesthetic, yields a mixture having a melting point lower than the melting point of the local anesthetic.

As used herein, a body has a shape which "conforms to" the nasal cavity of a human if the shape of the elongate body is, or becomes upon insertion into the nasal cavity, similar to the shape of the nasal cavity.

DESCRIPTION OF THE INVENTION

Inhibition of a Cerebral Neurovascular Disorder

One aspect of the invention is based on the discovery that intranasal, and preferably dorsonasal administration of a long-acting local anesthetic pharmaceutical composition to a human patient experiencing a cerebral neurovascular disorder (CNvD) inhibits the CNvD. The long-acting local anesthetic pharmaceutical composition comprises a local anesthetic ingredient selected from the group consisting of a long-acting local anesthetic, a persistent local anesthetic, and a sustained release formulation of a local anesthetic. The duration of relief from a symptom of a CNvD effected by intranasal administration of the long-acting local anesthetic pharmaceutical composition according to this method is at least about one hour, and is preferably at least about two hours. However, the duration may be at least about seventy-five, ninety, one hundred and five, or any other number of minutes such that the effective duration of relief is greater than that effected by intranasal administration of either lidocaine or cocaine. Inhibition of a CNvD may include inhibition of one or more symptoms or aspects of the CNvD. By way of example, inhibition of a CNvD includes inhibition of cephalic inflammation associated with the CNvD.

Intranasal, and preferably dorsonasal, administration of at least one long-acting or persistent local anesthetic, such as bupivacaine or ropivacaine, to a human patient experiencing a CNvD is sufficient to inhibit the CNvD or a symptom of the CNvD. Furthermore, intranasal or dorsonasal administration of a composition comprising a sustained release formulation of a shorter-acting local anesthetic inhibits the CNvD or a symptom thereof. By way of example, the CNvD may be a neurovascular headache, tinnitus which does not accompany a neurovascular headache, a cerebrovascular spasm which does not accompany a neurovascular headache, or an acute CNvD.

Symptoms of an acute neurovascular headache episode which can be inhibited by intranasal or dorsonasal administration of a long-acting local anesthetic pharmaceutical composition include, but are not limited to, head pain, cephalic inflammation (e.g., cerebral inflammation, meningeal inflammation, and inflammation of the hypothalamus or other portions of the brain), tinnitus, visual changes, phonophobia, photophobia, nausea, seizure, cerebrovascular spasm, symptoms of acute ischemic events, such as muscle weakness, dysphasia, dysphonia, cognitive impairment, autonomic imbalances, and the like.

Prior art methods of treating an acute CNvD often transiently and/or incompletely relieve head pain, the primary symptom of many CNvDs. In contrast, the compositions, kits, and methods of the present invention provide lasting and effective relief of the symptoms of a CNvD. Without wishing to be bound by any particular theory, it is believed that intranasal administration of a long-acting local anesthetic pharmaceutical composition to a patient experiencing a CNvD provides relief by inhibiting the physiological processes underlying the CNvD, whereby both the CNvD and symptoms of the acute CNvD are inhibited.

Prevention of an Acute Cerebral Neurovascular Disorder

The method described herein for inhibiting an acute CNvD includes a method of preventing a CNvD, including a method of preventing one or more symptoms (e.g., cephalic inflammation) associated therewith. Certain CNvDs, particularly migraines, are associated with prodromal symptoms which are experienced by a patient prior to the onset of the disorder. By treating a patient using the method described herein for inhibiting a CNvD at a time when the CNvD is expected or at a time when a prodromal symptom of the CNvD is experienced by the patient, the CNvD may be prevented.

Decreasing the Frequency and/or Severity of Recurring CNvDs

Numerous cerebral CNvDs including, but not limited to, migraines and TIAs, are characterized by periodic or irregular recurrence. Over time, severity of CNvDs often seems to increase and many CNvD-afflicted patients seem to experience CNvD episodes more frequently. It was observed that the frequency of recurrence and severity of CNvD episodes decreased with time in patients using the compositions and methods described in the present disclosure, even after treatment was no longer administered. These phenomena have not been previously observed with any other CNvD treatment method, including any migraine treatment method. The compositions, kits, apparatus, and methods of the invention are useful for decreasing the frequency of recurrence, the severity, or both, of CNvD episodes experienced by a patient afflicted with recurring CNvDs such as migraines and TIAs.

The invention thus includes a method of decreasing the frequency or severity with which CNvD episodes are experienced by a patient afflicted with a recurring CNvD. The method comprises intranasally, and preferably dorsonasally, administering to a patient experiencing a CNvD episode a long-acting local anesthetic pharmaceutical composition. The composition comprises a local anesthetic which is preferably a long-acting local anesthetic, a persistent local anesthetic, or a sustained release formulation of a shorter-acting or a long acting or a persistent local anesthetic, and is preferably administered to the patient early in the course of the CNvD episode. Preferably, the local anesthetic is administered to the patient within two hours following the onset of the episode, more preferably within one hour, and even more preferably within thirty minutes of the onset. Early administration provides more prompt relief, but administration of the local anesthetic according to this invention may be at any time with good results.

Other Acute Cerebral Neurovascular Disorders

Intranasal, and preferably dorsonasal, administration of a local anesthetic can also be used to treat any CNvD, in addition to migraines or other neurovascular headaches. Examples of acute CNvDs other than acute neurovascular headache episodes include, but are not limited to, tinnitus, seizures or seizure-like activities, cerebrovascular spasm, cephalic (e.g., meningeal) inflammation, and disorders manifested after and associated with an acute ischemic event such as a stroke, reversible ischemic neurological deficit, or transient ischemic attack. The local anesthetic compounds, formulations, dosages, and methods of administration which are useful for inhibiting these CNvDs are substantially the same as those described herein with respect to inhibiting a neurovascular headache. Where the acute CNvD is associated with cerebral ischemia, the amount of brain tissue which experiences ischemic damage may be reduced by this method.

Stimulation of DnNSs such as the trigeminal nerve can induce release from the DnNS of peptides and other neurotransmitters and humoral factors such as nitric oxide. Some of these neurotransmitters and humoral factors resemble (or are identical to) compounds released from injured, hyperstimulated, or growing nerves. These compounds can induce meningeal inflammation, and can, over time, induce anatomic and physiologic changes which facilitate pathways that allow more efficient transmission of nociceptive impulses and that lower triggering thresholds. Thus, if release or endurance of these compounds in the vicinity of the DnNS is not minimized, the DnNS can become hypersensitized, with the result that the CNvD recurs more frequently or readily. Release of compounds which induce meningeal inflammation can be minimized, as described herein, by anesthetizing the DnNS for an effective period of at least about one hour, and preferably two hours. Release of such compounds may also be minimized by providing a serotonin (5HT) agonist or another pharmaceutical agent to the DnNS, preferably in conjunction with the long-acting local anesthetic pharmaceutical composition. These two agents may, for example, be administered in the form of a single pharmaceutical composition comprising both a long-acting local anesthetic composition and a 5HT agonist (e.g., sumatriptan, zolmitriptan, rizatriptan, or naratriptan), or in the form of two separate pharmaceutical compositions (e.g., an intra- or dorsonasally administered long-acting local anesthetic pharmaceutical composition and an oral 5HT agonist) having overlapping periods of biological effect. When the 5HT agonist is administered locally (e.g., dorsonasally) to the DnNS, onset time of the pharmacological effect of the agonist may be reduced and duration of the pharmacological effect of the agonist may be extended by administering the agonist in conjunction with a vasoconstrictor. Furthermore, uptake of the 5HT agonist may be further improved by including the R-enantiomer of the local anesthetic (e.g., R-bupivacaine or a mixture of the R- and L-enantiomers of bupivacaine, such as a mixture wherein about 5-30% of bupivacaine is R-bupivacaine) in the composition. An optimum concentration may be used, wherein a more effective, powerful, and prolonged nerve block can be obtained, while also allowing increased uptake of any co-administered pharmaceutical agent.

The local anesthetic compounds, formulations, dosages, and methods of administration which are useful for inhibiting these CNvDs are substantially the same as those described herein with respect to inhibiting a neurovascular headache. Where the acute CNvD is associated with cerebral ischemia, the amount of brain tissue which experiences ischemic damage may be reduced by this method.

Tinnitus, cephalic inflammation, and these other CNvDs may also be inhibited by anesthetizing a DnNS using alternate anesthetic methods including, but not limited to, transcutaneous electrical neural stimulation, electromagnetic techniques, application of radio frequency radiation, and surgical intervention to sever or disrupt the DnNS.

Duration of Anesthetic Effect

It has been discovered that intranasal administration of a long-acting local anesthetic pharmaceutical composition is necessary in order to inhibit a CNvD in a human patient. That is, intranasal administration of relatively shorter-acting local anesthetic compositions, such as a lidocaine-containing composition which is not a sustained release formulation, provides only transient relief (i.e., less than about one hour) from CNvD symptoms, without inhibiting the CNvD.

It is preferable that the long-acting local anesthetic pharmaceutical composition of the invention, when administered intranasally, and preferably dorsonasally to a patient experiencing a CNvD, inhibits at least one symptom of the CNvD for a period of at least about one hour. Thus, as described herein, compositions comprising bupivacaine or ropivacaine are effective for inhibiting a CNvD when administered intranasally to a patient, while compositions comprising lidocaine in a non-sustained release formulation are not effective for inhibiting a CNvD. Thus, the long-acting local anesthetic pharmaceutical composition preferably comprises a local anesthetic ingredient which relieves at least one symptom of a CNvD for a period greater than the period of relief provided by intranasal administration of lidocaine, and more preferably relieves the symptom for at least about as long as ropivacaine.

It is believed that anesthesia of a DnNS for a period of at least about one hour, or preferably at least about two hours, results in inhibition of both the symptoms and the physiological processes of a CNvD, including sterile inflammation and vascular lability, associated with neurovascular headache episodes such as migraines and cluster headaches. Thus, for example, a migraine and its accompanying symptoms may be inhibited by intranasally, and preferably dorsonasally, administering a long-acting local anesthetic, a persistent local anesthetic, or a sustained release formulation of a local anesthetic to a patient experiencing the migraine and its symptoms. Preferably, the period is one which is effective to terminate these processes, whereby both the processes and the symptoms associated with the CNvD are terminated.

At least one investigator (Barre, 1982, Headache 22:69-73) has investigated the use of cocaine, a toxic, addictive, shorter-acting local anesthetic with well-known potent central nervous system properties, to relieve the pain associated with an individual headache episode associated with a cluster headache.

The addictive, toxic, and central nervous system excitatory qualities of cocaine render it an inappropriate treatment in virtually all current clinical settings. Hence, it is preferable that the local anesthetic used in the method of the invention be a local anesthetic other than cocaine. Thus, it is preferred to use a long-acting local anesthetic, a persistent local anesthetic, or a sustained release form of a shorter-acting local anesthetic other than cocaine in the methods of the invention.

Prior art investigations have examined the effectiveness of lidocaine, a shorter-acting local anesthetic, for providing relief from headaches of neurovascular origin (Kittrelle et al., 1985, Arch. Neurol. 42:496-498; Kudrow et al., 1995, Headache, 35:79-82; Maizels et al., 1996, J. Amer. Med. Assoc. 276:319-321). These investigations involved intranasal administration of 4% (w/v) lidocaine, wherein the doses were sometimes repeated. Although many patients in these studies experienced a short term decrease in head pain, a significant number of these patients required supplemental medication with other known headache therapeutic agents and the rate of rebound was high.

Not recognized by these investigators was the fact that their investigations were hampered by the incapacity of lidocaine to provide consistent, long-lasting relief from the CNvD for a period of at least about one hour. Hence, although intranasal administration of high concentrations of lidocaine provided short term pain reduction, the acute neurovascular headaches experienced by the patients worsened or rebounded when the anesthetic effects of lidocaine subsided, within about an hour. Any effect which long-acting local anesthetics might have had upon inhibiting acute neurovascular headache episodes in the patients involved in those investigations was not recognized. The fact that no further development of lidocaine or its derivatives as the primary pharmaceutically active agent for persistent or recurring neurovascular headache relief was pursued, despite the critical need for such agents, is further evidence that the importance of the period of inhibition of at least one symptom of the CNvD, such as a period on the order of at least about one hour, and preferably at least about two hours, was not recognized as being useful to abort the physiologic pathology of sterile inflammation and vasomotor instability which, when not aborted, triggers another headache episode upon subsidence of the anesthetic effect of the shorter-acting local anesthetic.

The results of studies by Kudrow et al. (1995, Headache, 35:79-82), Maizels et al. (1996, J. Amer. Med. Assoc. 276: 319-321), and Bane (1982, Headache 22:69-73) can be explained by the model of CNvDs presented herein, wherein a DnNS such as the SPG is involved in the pathogenesis of headaches of neurovascular etiology. None of these prior art studies recognized that the severely limited effectiveness of intranasal administration of either lidocaine or cocaine for the alleviation of pain associated with a headache of neurovascular etiology was due to the fact that lidocaine and cocaine are merely shorter-acting local anesthetics when used in this manner. Indeed, repeat doses of cocaine and lidocaine were needed to treat individual and subsequent short duration headache episodes associated with a cluster headache.

Inhibition of a CNvD such as an neurovascular headache requires intranasal, and preferably dorsonasal, administration of a long-acting local anesthetic pharmaceutical composition which provides relief from a symptom of the CNvD for a period longer than that effected by the treatments in the investigations of Kudrow et al., Maizels et al., and Barre, namely for a period of at least about one hour, and preferably at least about two hours.

Shorter-acting local anesthetics are not consistently or reliably effective for inhibiting a CNvD when administered in a single dose or in multiple doses administered over a short period of time such as a few minutes. Nonetheless, using the teachings of the present invention, it is possible to use shorter-acting local anesthetics in a manner more effective to inhibit a CNvD without causing the side effects associated with repetitive dosing of these agents at high concentration. In order to inhibit a CNvD, it is necessary that a shorter-acting local anesthetic be intranasally, and preferably dorsonasally, administered as a sustained release formulation, or that an additional compound which extends the duration of anesthesia effected by the shorter-acting local anesthetic, such as epinephrine or another vasoconstrictor, be co-administered to the patient. Preferably the additional compound is administered to the patient in a composition comprising the local anesthetic and the additional compound. Compounds, formulations, and dosages of the vasoconstrictors described in this method are known in the art. For example, vasoconstrictive compositions may be used at art-recognized effective doses, such as, about 0.001 milligram per milliliter to about 0.01 milligram per milliliter of epinephrine. Similarly, the other additional compounds described in this paragraph may be used at art-recognized effective doses.

Theory Proposed to Explain the Efficacy of the Compositions and Methods of the Invention for Inhibiting a Neurovascular Headache It should be appreciated that the superiority of the compositions and methods of the invention relative to the compositions and methods of the prior art does not depend upon the accuracy of the theory offered to explain the superior results.

While not wishing to be bound by any particular theory of operation, it is believed that intranasal administration of the composition of the present invention inhibits a neurovascular headache by anesthetizing a dorsonasal nerve structure (DnNS) in the patient for a period effective to inhibit the physiological processes that result in the neurovascular headache, such as a period on the order of at least about an hour, and preferably at least about two hours.

Still without wishing to be bound by any particular theory, it is believed that the following model explains the physiological processes underlying an acute neurovascular headache. An acute neurovascular headache generation center (ANvHGC) is located in the pons of the human brain, near the locus coeruleus. The ANvHGC initiates an excitatory signal which affects the reticular formation, the trigeminal nerve, and sympathetic, parasympathetic, and other outflows from the midbrain and pons. Trigeminal nerve fibers innervate cerebral blood vessels and modulate vasomotor function and intra- and extracranial blood vessel tone and communicate with multiple neural structures. Stimulation of the trigeminal nerve by the ANvHGC results in changes in efferent and afferent neural activity and changes in regional intracranial blood flow. Many factors, including stimulation of the trigeminal nerve by the ANvHGC, facilitate neurogenic inflammation and associated vasomotor and other changes, including, but not limited to, monocytic and lymphocytic infiltrates, perivascular edema, and release of neurohumoral and other chemical factors. This results in intra- and extracranial neural and vascular hyperexcitability. This hyperexcitability decreases the threshold for neuronal and humoral signaling and other triggers which induce further vasospasm or further neuronal hyperexcitability and altered efferent and afferent activity. Prolonged vasospasm leads to tissue ischemia, which induces further release of neurohumoral factors, increases perivascular edema, and exacerbates neurogenic inflammation. These local neurovascular changes induce greater neuronal and vascular hyperexcitability. All of these factors contribute to the pathophysiologic cycle of neurovascular headache.

Altered cerebral blood flow, neurogenic inflammation, and associated vasomotor and other changes are experienced by the patient as head pain, tinnitus, symptoms of cerebrovascular spasm such as visual changes, blindness, or disorientation, or some combination of these, and contribute to the prodromal and other symptoms of an acute neurovascular headache. Data obtained recently by Pappagallo et al. (supra) confirm that inflammation (presumably neurogenic) of the meninges is associated with head pain in patients experiencing migraine.

Even in the absence of head pain, intracranial and extracranial blood vessel hyperexcitability and neuronal hyperexcitability can lead to recurrence or rebound of an acute neurovascular headache, such as a migraine, or to prolongation of the physiology of the neurovascular headache cycle. Thus, an alternate neurovascular headache cycle may include a period during which symptoms of the neurovascular headache are not perceived by the patient, but during which period intracranial and extracranial blood vessels and nerves remain hyperexcitable, as in the case of a series of individual headache episodes associated with a cluster headache or a recurrent migraine.

Further, without wishing to be bound by any particular theory, it is believed that intranasal administration of a shorter-acting local anesthetic such as lidocaine or cocaine merely provides analgesia alone by inhibiting transmission of nerve impulses for a relatively short period—less than about an hour. Administration of a shorter-acting local anesthetic does not interrupt the physiological processes which cause the pain associated with an acute CNvD such as an acute neurovascular headache episode. The duration of the anesthetic effect of a shorter-acting local anesthetic such as lidocaine is too short to permit intracranial and extracranial blood vessels and nerves to recover from the hyperexcitable state. The duration of the anesthetic effect of a shorter-acting local anesthetic is also too short to allow clearance of vascular and perivascular humoral and cellular factors from cerebrovascular tissue. The result of the short duration of the anesthetic effect of a shorter-acting local anesthetic is that the neurogenic inflammation continues, the neurovascular headache cycle persists, and, once the anesthetic effect of the shorter-acting local anesthetic subsides, the neurovascular headache rebounds.

In contrast, in accordance with the present invention, anesthesia of a DnNS such as the SPG for an effective period that permits intracranial and extracranial nerves and intracranial and extracranial blood vessels to recover from the hyperexcitable state, arrests neurogenic inflammation, and permits clearance of vascular and perivascular humoral and cellular factors from cerebrovascular tissue, inhibits the physiological processes which cause the occurrence or persistence of an acute neurovascular headache. The effective period of such anesthesia must be sufficient to affect these physiological processes in a beneficial manner, such as a period on the order of at least about an hour, and preferably at least about two hours. It is understood that the effective period may vary among individuals.

Compromised cerebral vascular flow volume and neurogenic inflammation are believed to be related to neural and humoral factors including increased local concentrations of nitric oxide, vasoactive intestinal peptide (VIP), substance P, and other factors present in ischemic or inflamed tissue. It is believed that the mechanism by which neurogenic inflammation is arrested and recovery of nerves and blood vessels from their hyperexcitable state is permitted following anesthesia of a DnNS, such as the SPG, for an effective period of time involves neuronal stabilization and clearance from intra- and extracranial neuronal and vascular tissues of nitric oxide, VIP, substance P, one or more neurotransmitters, one or more peptides, cellular infiltrates, or a combination of these factors. Concomitantly, blood vessel permeability is normalized and perivascular edema decreases. Anesthesia of the DnNS for the effective period furthermore limits release of humoral agents in cerebrovascular tissue and decreases vasoconstriction and, by inhibition of neural mediated increases in blood vessel smooth muscle tone, may effect vasodilation, thereby permitting dissipation of local humoral and cellular factors associated with head pain and other symptoms. The result is that when the anesthetic effect of the local anesthetic subsides, the cranial nerves and vascular structures are no longer hyperexcitable, neurogenic inflammation has been arrested or reversed, local humoral and cellular factors have dissipated, and thus the neurovascular headache cycle does not continue or rebound. This model represents a possible explanation of the superiority of the compositions and methods of the invention for inhibiting an acute neurovascular headache, relative to the compositions and methods of the prior art, which were ineffective or of very limited effectiveness for inhibiting such disorders.

The ability to block nerve fibers which mediate the processes involved in the headache cycle varies with the particular local anesthetic used. Shorter-acting local anesthetics do not exhibit the same degree of differential blockade (i.e., sensory blockade compared with autonomic blockade) exhibited by long-acting and persistent local anesthetics. Without wishing to be bound by any particular theory, it is believed that the anti-neurovascular headache efficacy exhibited by long-acting and persistent local anesthetics, relative to the non-efficacy of shorter-acting local anesthetics, may be attributable in whole or in part to the degree of differential blockade capabilities exhibited by these types of local anesthetics.

One aspect of the present invention may be explained, at least in part, by the hypothesis that intranasal, and preferably dorsonasal, administration of a long-acting local anesthetic pharmaceutical composition inhibits an acute CNvD such as an acute neurovascular headache episode. This treatment is hypothesized to result in anesthesia of a DnNS such as the SPG for a period of at least about one hour, and preferably for a period of about two hours.

Anesthesia of a DnNS such as the SPG may be achieved in any of a number of ways. For example, at least one long-acting or persistent local anesthetic may be intranasally or dorsonasally administered to a patient to effect anesthesia of the DnNS. Further by way of example, a sustained release formulation of a shorter-acting, long-acting, or persistent local anesthetic may be dorsonasally administered to a patient to effect anesthesia of the DnNS. Any method known in the art of anesthetizing nerves may be used to anesthetize the DnNS. Further by way of example, acupuncture techniques, application of electrical potential to a DnNS, or application of electromagnetic radiation, such as light or radio frequency radiation, to a DnNS may be used to anesthetize the DnNS. Intranasal, and preferably dorsonasal, administration of a long-acting local anesthetic pharmaceutical composition is a preferred method of inhibiting a CNvD.

Inhibition of a migraine by dorsonasal administration of at least one local anesthetic is an effective means of arresting the cascade of migraine development with consequent sterile inflammation and protracted multisystem aggravation of symptoms, particularly where such anesthesia persists for a period of at least about an hour, and preferably at least about two hours. Any of the pharmaceutical compositions described herein may be used for dorsonasal administration of the local anesthetic, using the dosages and formulations herein. As will be understood by one skilled in the art, the optimal dosage and formulation for use with an individual patient depends upon the age, size, condition, state of health, and preferences of the patient, as well as upon the identity of the local anesthetic. Selection of optimal doses and formulations are, in view of the present disclosure, well within the skill of the ordinary artisan.

Inhibition of a CNvD, a symptom of the CNvD, or both, occur very rapidly following intranasal or dorsonasal administration of a long-acting or persistent local anesthetic such as ropivacaine. Half maximal inhibition occurs within about three minutes, and the rate of rebound is negligible. Photophobia and nausea are inhibited at the same time as pain following dorsonasal administration of ropivacaine. The coincidental effect may be due to the wide ranging effects of intranasal administration of the composition of the invention on multiple subpial and cerebrovascular systems. By contrast, the migraine therapeutic effects of a serotonin receptor agonist depends on the ability of vascular flow to effect an effective concentration of the agonist at the site of the compromised cerebral blood vessels. The serotonin receptor agonists show intersubject variance in efficacy due to the biphasic nature of the relationship between the concentration of the agonist and the physiological effect in vascular structures. Serotonin receptor agonists also exhibit variable efficacy due to variable effect of individual serotonin receptor agonists upon blood vessels within the major cerebrovascular and subpial structures of a patient.

Combining a long-acting local anesthetic pharmaceutical composition with a serotonin receptor agonist will have an additive, if not synergistic effect on therapeutic efficacy because the disease process is inhibited by different mechanisms. In particular, serotonin receptor subclass 5HT1F agonists (e.g., LY334,370) are noteworthy in their decreased side effect profile and decreased efficacy, relative to serotonin receptor subclass 5HT1D agonists, and may be used in combination with an anesthetic in a long-acting local anesthetic pharmaceutical composition, such as that described herein. Such a composition will exhibit increased efficacy, relative to the serotonin receptor subclass 5HT1F agonist alone, regardless of the dose of the agonist.

Recurring CNvDs lead to cumulative damage and neurological defects among patients afflicted with these CNvDs. For example, certain patients who are afflicted with recurring migraines sustain permanent neurological damage. Without wishing to be bound by any particular theory, it is postulated that anatomic and physiologic pathologies may be secondary to the cumulative effects of repetitive pain stimuli, pain impulses, ischemia, sterile inflammation, related processes, or some combination of these. Effective management of the neurovascular ischemic component of a recurring CNvD may decrease cumulative neurological damage attributable to the CNvD episodes. For example, ending the ischemic component of a migraine promptly after the onset of the acute migraine episode may decrease the damage and deficit exhibited in certain ophthalmic, basilar, or other migraine patients. Compromised nerve structures have a lower threshold of neuronal signaling to restart subsequent CNvD episodes. Thus, decreasing the cumulative neurological damage attributable to recurring CNvD episodes decreases the frequency with which CNvD episodes are experienced by the patient.

Further without wishing to be bound by any particular theory, the pain and other neuronal signals transmitted by cerebral nerve structures during a CNvD episode may predispose the same or other nerve structures to onset of a subsequent CNvD episode by processes analogous to "neuronal learning" or to central sensitization and amplification. Neuronal learning is a theory which has been described by others to explain the apparent self-facilitating nature of pain generation and sensation. The theory of neuronal learning postulates that the transmission of pain impulses by a particular neural pathway predisposes that particular neural pathway to future transmission of pain impulses in response to triggers or impulse-generating stimuli of lower magnitude than would normally be required for pain sensation. Noxious stimuli can also cause lasting central sensitization whereby altered sensory processes in the central nervous system amplify, even in the distant future, subsequent pain. By way of example, it has been demonstrated in surgical patients that pre-surgical central neurologic blockade (e.g., using epidural analgesia) reduces the sensation of postoperative pain in the patients, even up to more than nine weeks following surgery, relative to patients who receive identical central neurologic blockade postoperatively (Gottschalk et al., 1998, J. Amer. Med. Assoc. 279:1076-1082; Woolf et al., 1993, Anesth. Analg. 77:362-379; Shis et al., 1994, Anesthesiology 80:49-56). It is believed that failure to block transmission of pain impulses from surgically-affected sensory neurons in the postoperatively blocked patients lowers the threshold sensation needed to trigger pain impulse transmission from these neurons or facilitates central amplification of pain. In contrast, it is believed that blockade of transmission of pain impulses from the same surgically-affected sensory neurons in presurgically blockaded patients prevents this threshold-lowering effect.

While still not wishing to be bound by any particular theory, it is believed that dorsonasal administration of a long-acting or persistent local anesthetic at an early stage of a CNvD episode blocks the transmission of pain impulses from, through, or both, relevant cerebral or other neurological structures, such that these neurological structures therefore do not experience the threshold-lowering affect attributable to neuronal learning. The amount of stimulation that will induce a subsequent episode of a CNvD is thereby not lowered. Additionally, there is no central amplification of perceived pain. Because the threshold stimulation required for inducement of CNvD episodes is not lowered, and further because there is no central amplification of pain, patients treated using the compositions, kits, and methods of the invention are less predisposed to subsequent CNvD episodes, and the frequency and severity of any subsequent CNvD episodes is reduced.

Intranasal, and preferably dorsonasal, administration of a long-acting local anesthetic pharmaceutical composition can also be used to reduce the severity of an acute cerebral ischemic event, thereby decreasing neurologic deficits resulting therefrom. Without wishing to be bound by any particular theory of operation, it is believed that the following proposed mechanism explains the efficacy of this method. Tissue damage caused by an acute ischemic event is mediated by a shortage of oxygen in such tissue. This tissue damage may be alleviated in at least two ways. Damage may be alleviated by counteracting the cause of the tissue hypoxia or by inducing supplementary oxygen delivery to the tissue. Intranasal administration of a local anesthetic is believed to reduce the severity of an acute cerebral ischemic event in both of these ways. It is believed that intranasal administration of a local anesthetic interrupts the neural component which contributes to the vasospasm associated with an acute cerebral ischemic event. Relief of this neural component of the event can reduce or eliminate ischemia associated with the event. Furthermore, it is believed that vasodilatory effects of intranasally administered local anesthetics cause dilation of blood vessels supplying the ischemic tissue, decreasing the degree of vessel occlusion, thereby increasing blood supply to the ischemic tissue. These vasodilatory effects may also increase blood flow through the blood vessel occlusion, for example by dilating proximal blood vessels, thereby increasing the pressure gradient across the occlusion, resulting in less watershed ischemia.

Inhibition of Muscular Headaches

Another aspect of the present invention is based on the discovery that intranasal, and preferably dorsonasal, administration of a local anesthetic to a human patient experiencing a muscular headache is sufficient to inhibit the muscular headache or a symptom associated therewith. Preferably, the local anesthetic is a long-acting or persistent local anesthetic, but shorter-acting local anesthetics are recognized as being effective to inhibit a muscular headache as well, using this method.

Prior art methods of treating a muscular headache have focused on using acetylsalicylic acid and its derivatives, non-steroidal anti-inflammatory drugs, sedatives, narcotics, and other drugs to decrease head pain, the primary symptom of muscular headaches.

What was not known, and what represents a surprising discovery, is that intranasal, and preferably dorsonasal, administration of a local anesthetic, preferably one which exhibits a duration of anesthesia equal to at least about a few minutes, is effective both to relieve head pain during the period of anesthesia and, more importantly, to inhibit a muscular headache.

Although all types of head pain, even head pain associated with diverse classes of headaches, may have similar aspects of presentation, character, or pathophysiology, muscular headaches are recognized as a separate class of headache, with distinct characteristics (Headache Classification Committee of the International Headache Society, 1988, Cephalalgia 8 (Suppl. 7):19-28).

It has not previously been recognized that local anesthetics, when administered intranasally or dorsonasally, were capable of relieving muscular headache pain or muscle spasm associated with muscular headaches.

The present invention also includes a method of inhibiting a muscular headache episode in a human patient, the method comprising intranasally, and preferably dorsonasally, administering to the patient a composition comprising a local anesthetic and an analgesic or other pharmaceutically active agent. Preferably, the local anesthetic is not cocaine, and administration of the composition results in relief of a symptom of the muscular headache and further results in improved delivery of the analgesic or other agent to a cerebral neurovascular tissue of the patient. By way of example, the agent may be aspirin, acetaminophen, a non-steroidal anti-inflammatory drug, a tricyclic antidepressant, an anxiolytic, a serotonin agonist such as a triptan or a chroman compound, a narcotic, or a drug that increases cerebral levels of gamma-aminobutyric acid. Compounds, formulations, and dosages of analgesics and other pharmaceutically active agents described in this method are known in the art. Owing, in part, to the vasodilatory activity of local anesthetics, these compounds may be used according to this method at doses of about half their art-recognized doses to their full art-recognized doses.

The method described herein for treating a muscular headache episode can also be used to prevent such an episode. Certain muscular headaches can be reliably predicted to occur following particular patient activities prior to the onset of the episode. By treating a patient using the method described herein for treating a muscular headache episode at a time when the episode is expected, at a time when the patient is under emotional distress, or at a time when the patient is exposed to another headache-triggering condition, the muscular headache episode may be prevented.

It is believed that the compositions and methods of the invention provide more rapid and complete relief of muscular headache symptoms than do known compositions and methods. Furthermore, intranasal and dorsonasal administration of local anesthetics are not associated with the side effects known to be associated with prior art headache treatments, and do not induce tolerance, as do prior art headache treatments. Thus, besides being a useful headache treatment in itself, the method of the invention is a useful alternative or adjunctive therapeutic modality with regard to prior art muscular headache treatments.

Theory Proposed to Explain the Efficacy of the Compositions and Methods of the Invention for Inhibiting a Muscular Headache It should be appreciated that the superiority of the compositions and methods of the invention relative to the compositions and methods of the prior art does not depend upon the accuracy of the theory offered to explain the superior results. Regardless of the mechanism by which muscular headaches are generated, intranasal, and preferably dorsonasal, administration of a local anesthetic, preferably a long-acting or persistent local anesthetic, inhibits a muscular headache.

Without wishing to be bound by any particular theory, it is believed that the following model explains the physiological processes underlying a muscular headache. It is believed that non-desirable sustained muscle contraction is related to local pathology, central influences and multisynaptic modulation, and involves gamma efferent neuronal muscle spindle activation. Related monosynaptic conduction through the ventral horn augments both efferent neuronal discharge and muscle contraction. A muscular headache cycle of pain, muscle spasm, local chemical changes, neuronal excitability or hyperexcitability, skeletal muscle blood vessel compression or spasm, and anxiety ensues.

Anesthesia of a DnNS such as the SPG effected by dorsonasal delivery of a topical anesthetic is an effective means of inhibiting a chronic muscular headache, particularly where such anesthesia persists for a period of at least about an hour, and preferably at least about two hours. Anesthesia of the DnNS and consequent relief of associated symptoms occurs very rapidly following intranasal or dorsonasal administration of a long-acting or persistent local anesthetic such as ropivacaine. Half maximal arrest occurs within about three minutes. The effect may be due to the wide ranging effects of DnNS anesthesia on multiple subpial and cerebrovascular systems. For example, the trigeminal nerve is in communication with upper cervical nerves, particularly cervical nerve 2. Interruption of efferent or afferent limbs of cervical nerve 2 would inhibit facial and scalp skeletal muscle spasm, thereby breaking a major component of the muscular headache cycle.

Anesthesia of a DnNS such as the SPG for a period of at least about a few minutes, preferably at least about one hour, and more preferably at least about two hours, may be achieved in any of a number of ways. For example, a shorter-acting local anesthetic may be intranasally or dorsonasally administered to a patient to effect anesthesia of the DnNS for a period of less than about one hour, it being understood that such treatment may be effective only to alleviate a muscular headache episode, possibly without inhibiting the episode. Also by way of example, a long-acting or persistent local anesthetic may be intranasally or dorsonasally administered to a patient to effect anesthesia of the DnNS. Further by way of example, a sustained release formulation of a shorter-acting, long-acting, or persistent local anesthetic may be dorsonasally administered to a patient to effect anesthesia of the DnNS. Any method known in the art of anesthetizing nerves may be used to anesthetize the DnNS. Further by way of example, acupuncture techniques, application of electrical potential to a DnNS, or application of electromagnetic radiation, such as light or radio frequency radiation, to a DnNS may be used to anesthetize the DnNS.

Local Anesthetics

The chemical identity of the local anesthetic or anesthetics used in the compositions and methods of the invention is not critical. As described herein, long-acting or persistent local anesthetics may be administered in pharmaceutically acceptable carriers, and shorter-acting local anesthetics may be administered in sustained release formulations or in conjunction with an additional compound which extends their anesthetic effect.

Compounds having local anesthetic activity which may be used to practice the invention include, but are not limited to, articaine, ambucaine, amolanone, amylocaine, benoxinate, betoxycaine, biphenamine, bupivacaine, levo-bupivacaine, butacaine, butamben, butanilicicaine, butethamine, butoxycaine, carticaine, 2-chloroprocaine, cocaethylene, cocaine, cyclomethycaine, dibucaine, dimethisoquin, dimethocaine, diperodon, dyclonine, ecgonidine, ecgonine, ethyl aminobenzoate, ethyl chloride, etidocaine, levo-etidocaine, dextro-etidocaine, beta-eucaine, euprocin, fenalcomine, fomocaine, hexylcaine, hydroxyprocaine, hydroxytetracaine, isobutyl p-aminobenzoate, leucinocaine mesylate, levoxadrol, lidocaine, lidocaine salicylate monohydrate, meperidine, mepivacaine, levo-mepivacaine, meprylcaine, metabutoxycaine, methyl chloride, myrtecaine, naepaine, octacaine, orthocaine, oxethazaine, parethoxycaine, phenacaine, phenol, pipecoloxylidides, piperocaine, piridocaine, polidocanol, pramoxine, prilocalne, procaine, propanocaine, proparacaine, propipocaine, propoxycaine, pseudococaine, pyrrocaine, quinine urea, risocaine, ropivacaine, levo-ropivacaine, salicyl alcohol, sameridine, tetracaine, tolycaine, trimecaine, veratridine, and zolamine, as well as 2-alkyl-2-alkylamino-2',6'-acetoxylidide compounds, such as those described in U.S. Pat. No. 3,862,321; glycerol 1,2-bis-aminoalkyl ether compounds, such as those described in U.S. Pat. No. 4,117,160; benzisoxazole compounds, such as those described in U.S. Pat. No. 4,217,349; O-aminoalkylsalicylate compounds, such as those described in U.S. Pat. No. 4,298,603; heterocyclic phenoxyamine compounds, such as those described in U.S. Pat. No. 4,379,161; 2- and 3-aryl substituted imidazo(1,2-A) pyridine compounds, such as those described in U.S. Pat. No. 4,871,745, in U.S. Pat. No. 4,833,149, and in U.S. Pat. No. 4,727,145; polyorganophosphazene compounds, such as those described in U.S. Pat. No. 4,495,174 and in U.S. Pat. No. 4,636,387; tertiary-alkylamino-lower acyl-xylidide compounds, such as those described in U.S. Pat. No. 3,925,469; amidinourea compounds, such as those described in U.S. Pat. No. 4,147,804; 3-(5'-adenylates) of lincomycin-type or clindamycin-type compounds, such as those described in U.S. Pat. No. 4,397,845; N-substituted derivatives of 1-(4'-alkylsulfonylphenyl)-2-amino-1,3-propanediol compounds, such as those described in U.S. Pat. No. 4,632,940; tertiary aminoalkoxyphenyl ether compounds, such as those described in U.S. Pat. No. 4,073,917; adenosine compounds, such as adenosine and adenosine mono-, di-, and triphosphate; lauryl polyglycol ether compounds, such as those described in U.S. Pat. No. 5,676,955 and mixtures of such ether compounds; 2-(omega-alkylaminoalkyl)-3-(4-substituted-benzylidene) phthalimidine compounds or 2-(omega-dialkylaminoalkyl)-3-(4-substituted-benzylidene) phthalimidine compounds, such as those described in U.S. Pat. No. 4,551,453; N,N,N-triethyl-N-alkyl ammonium salts, such as those described in U.S. Pat. No. 4,352,820; L-N-n-propylpipecolic acid-2,6-xylidide compounds, such as those described in U.S. Pat. No. 4,695,576; N-substituted 4-piperidinecarboxamide compounds, such as those described in U.S. Pat. No. 5,756,520; N-substituted 4-phenyl-4-piperidinecarboxamide compounds, such as those described in U.S. Pat. No. 5,360,805; polymers comprising repeating units of one or more local anesthetic moieties, such as polymers described in U.S. Pat. No. 3,914,283; compounds of formula (I):

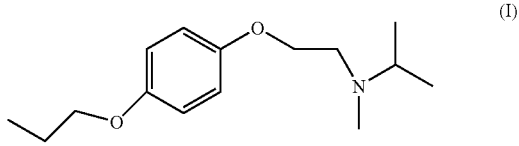

and its derivatives, such as those described in International Patent Application Publication No. WO 97/38675; compounds of formula (II):

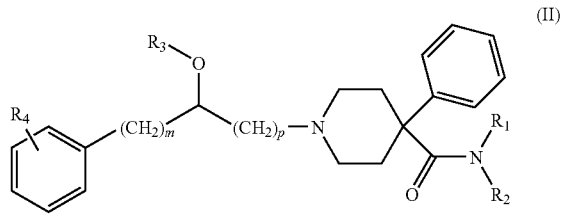

wherein $R_{1-4}$, m, and P are defined as in International Patent Application Publication No. WO 95/21821; compounds having a structure described in International Patent Application Publication No. WO 97/15548; compounds having a structure described in International Patent Application Publication No. WO 97/23467; compounds having a structure described in U.S. Pat. No. 4,870,086; compounds having a structure described in U.S. Pat. No. 4,529,601; long-acting topical anesthetic agents; long-acting topical anesthetic products of Astra {Astra Zeneca} of the "LTA" series of compounds; ester forms of any of these compounds, salts of any of these compounds, compounds otherwise chemically related to one of these compounds which would be effective in the present invention; and sustained release preparations of any of these agents, as described herein. Also included are derivatives of the foregoing, where the derivative is any chemically related compound effective for the present invention.

Synonyms, including chemical names, chemical formula, and trade names, for many of the local anesthetics described herein may be found in Physician's Desk Reference® (Medical Economics Co., Inc., Montvale, N.J., 51st ed., 1997) or in PDR® GENERICS™ (Medical Economics Co., Inc., Montvale, N.J., 2nd ed., 1996).

The local anesthetic is preferably selected from the group consisting of bupivacaine, levo-bupivacaine, ropivacaine, levo-ropivacaine, tetracaine, etidocaine, levo-etidocaine, dextro-etidocaine, and levo-mepivacaine.

Local anesthetics including, but not limited to, bupivacaine and ropivacaine, which are related to aminoacyl local anesthetics exhibit intrinsic vasoactive effects on cerebral blood vessel tone and reduce pain sensitivity locally. When administered dorsonasally, these compounds are believed to effect anesthesia of the SPG and other DnNSs, which results in increased volumetric flow of blood in cerebral blood vessels and reduces inflammation initiated by functional ischemia. It is understood that the S(levo)-enantiomer of ropivacaine and the S(levo)-enantiomer of bupivacaine exhibit lower physiological toxicity and better sensory blocking properties than the corresponding R(dextro)-enantiomers. The S(levo)-enantiomer of ropivacaine is preferred for use in the compositions and methods of the invention, as are the S(levo)-enantiomers of bupivacaine, etidocaine, and mepivacaine.

Ropivacaine exhibits lower cardiovascular and central nervous system toxicity than bupivacaine. Compared with bupivacaine, ropivacaine blocks nerve fibers, such as A(delta) and C sensory fibers, more preferentially than other neurons such as motor neurons (Rosenberg et al., 1986, Br. J. Anaesth. 55:163-167). Thus, ropivacaine is preferred over bupivacaine in the compositions, kits, and methods of the invention.

For local anesthetics which have a chiral center (e.g., bupivacaine and ropivacaine), the local anesthetic may be a single optical isomer of the local anesthetic, a racemic mixture of the optical isomers, or some other mixture of optical isomers. By way of example, a 90:10, a 80:20, a 75:25, a 70:30, or a 50:50 ratio, by weight or by molecule number, of one optical isomer to the other may be used. There is clinical evidence that mixtures of local anesthetics such as bupivacaine and ropivacaine, wherein about 10-25% of the anesthetic is present in the dextro-form can provide anesthesia of longer duration, more pronounced anesthetic effect, or both.

When the local anesthetic is an alkyl- or aryl-2-piperidinecarboxamide derivative such as mepivacaine, bupivacaine, ropivacaine, or etidocaine, the carbon atom at position 2 of the piperidine ring is a chiral center, as indicated with an asterisk in formula (III), wherein R is ethyl, phenyl, or $C_5$-$C_8$ straight- or branched-chain alkyl, and R' is 2,6-dimethylphenyl, thiophene, or 2,5-dimethylthiophene.

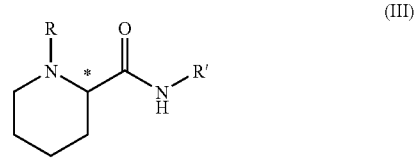

For these local anesthetics, it is preferred by the inventor to use the levo-enantiomer at this chiral center in the compositions, kits, apparatus, and methods of the invention.

Similarly, when the local anesthetic comprises a chiral center (indicated with an asterisk) having the structure of formula (IV), it is also preferred that the levo-enantiomer at the chiral center be used in the compositions, kits, and methods of the invention, wherein R and R' are as defined above and wherein either (i) each of R" and R''' is a straight-chain alkyl and R" and R''' have a total of 4 to 6 carbon atoms, or (ii)

R" and R'" together form a heteroalkyl ring having a total of 5 to 7 carbon atoms and a nitrogen atom.

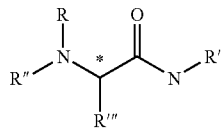

(IV)

By way of example, etidocaine and prilocalne each comprise a chiral center within the definition of the structure of formula (IV), but having different R-groups.

It is understood by the inventor that the potency of anesthesia effected by local administration of an aryl-2-piperidinecarboxamide derivative such as bupivacaine, ropivacaine, or lidocaine may be increased by increasing the lipid solubility of the derivative. This may be achieved, for example, by increasing the lipophilic character of substituent of the piperidyl nitrogen atom. The partition coefficient of ropivacaine (in an n-heptane/buffer biphasic system) is about 2.9 times greater than the partition coefficient of lidocaine (Rosenberg et al., 1986, Br. J. Anaesth. 58:310-314). The partition coefficient of bupivacaine is about 10 times greater than the partition coefficient of lidocaine (Id.). As described herein, ropivacaine and bupivacaine are long-acting local anesthetics, while lidocaine is not a long-acting local anesthetic. Thus, a way in which a skilled artisan may determine whether a particular local anesthetic is a long-acting local anesthetic is to determine whether the partition coefficient of the local anesthetic in an n-heptane/aqueous biphasic system is greater than the partition coefficient of lidocaine in such a system. If the partition coefficient of the particular local anesthetic is greater than the partition coefficient of lidocaine, then the particular local anesthetic is likely a long-acting local anesthetic. Preferably, the partition coefficient of the particular local anesthetic is at least 2.9 times greater than the partition coefficient of lidocaine. The potency of anesthesia of a local anesthetic may be increased by modifying the chemical structure of the local anesthetic in such a manner as to increase the partition coefficient of the local anesthetic, for example by adding hydrophobic substituents to the local anesthetic molecule or lengthening hydrophobic substituents of the local anesthetic. Preferably, the local anesthetic used in the compositions, kits, and methods of the present invention has a partition coefficient in an n-heptane/aqueous biphasic system greater than the partition coefficient of lidocaine in such a system.

It is understood by the inventor that the duration of anesthesia effected by local administration of an anesthetic such as an aryl-2-piperadinecarboxamide derivative is related to the proportion of the anesthetic which is bound to protein in vivo. Approximately 95% of each of bupivacaine and ropivacaine is bound to protein in vivo, while only about 65% of lidocaine is bound to protein in vivo. Thus, another way in which a skilled artisan may determine whether a particular local anesthetic is a long-acting local anesthetic is to determine whether the proportion of the particular local anesthetic which is bound to protein in vivo is greater than the proportion of lidocaine which is bound to protein in vivo. If the proportion of the particular local anesthetic which is bound to protein in vivo is greater than the proportion of lidocaine which is bound to protein in vivo, then the particular local anesthetic is likely a long-acting local anesthetic. The proportion of the local anesthetic used in the compositions, kits, and methods of the present invention which is bound to protein in vivo should be greater than about 65%. Preferably, the proportion of the particular local anesthetic which is bound to protein in vivo is at least about 95%.

The duration of anesthesia of a local anesthetic may be increased by modifying the chemical structure of the local anesthetic in such a manner as to increase the proportion of the particular local anesthetic which is bound to protein in vivo, for example by adding chemical substituents to the particular local anesthetic molecule which are capable of binding, covalently or non-covalently, to protein moieties.

The therapeutic effects of local anesthetics in the present invention are not directly proportional to their prior art use elsewhere in the body as local anesthetics. Thus, the duration and pain-relieving effects of the long-acting and persistent local anesthetics in the present invention are enhanced, compared to their use as local anesthetics elsewhere in the body. The enhanced duration and pain-relieving effects of the long-acting and persistent local anesthetics of the present invention are surprising, compared with the effects achieved using other methods of using local anesthetics.

For example, administration of ropivacaine may anesthetize a nerve structure for a period about 1.5 to about 4 times that achieved by administration of lidocaine, depending on the location and type of the nerve structure, and further depending on the concentration and total dose of the local anesthetic and on the presence of vasoconstrictors or other drugs which affect either uptake of the local anesthetic by the nerve structure or clearance of the local anesthetic from the anatomical site of the nerve structure. The difference between the period of anesthesia effected by administration of ropivacaine and the period of anesthesia effected by administration of lidocaine is less pronounced when the site of administration is a skin or mucosal surface. Thus, one would expect that if lidocaine and ropivacaine affected CNvDs and their symptoms by the same mechanism, administration of ropivacaine to a patient afflicted with a CNvD would provide relief lasting no more than about 4 times as long as the relief provided by administration of lidocaine, and probably closer to no more than about 1.5 times as long. In fact, as described herein, the relief provided by administration of ropivacaine to CNvD patients, such as migraine patients, persisted far longer than the duration of relief provided by administration of lidocaine to such patients. This surprising result further highlights the difference between prior art methods of relieving a symptom of a CNvD and the methods of the invention for inhibiting a CNvD.

The use of microdroplets comprising a general anesthetic to effect local anesthesia are known and have been described, for example in U.S. Pat. No. 4,622,219. Liposomal preparations of local anesthetics are also known and have been described, for example in U.S. Pat. No. 4,937,078. However, neither the use of a general anesthetic in microdroplet form nor the use of a sustained release preparation of one or more local anesthetics has been described prior to the present disclosure for the purpose of inhibiting, or otherwise treating an acute CNvD or for the purpose of reducing the severity of an acute cerebral ischemic event in a human patient. The preparations and uses of general anesthetics in microdroplet form and the preparations and uses of liposomal preparations of one or more local anesthetics are included within the compositions, kits, apparatus, and methods of the invention. General anesthetics which can be used in microdroplet form include, but are not limited to, desflurane, diazepam, enflurane, etomidate, halothane, isoflurane, methohexital sodium, methoxyflurane, midazolam hydrochloride, propofol, sevoflurane, and thiopental sodium.

Dosing Information

The following dosing information is believed to be useful for the CNvD-inhibiting methods and the muscular headache-inhibiting methods of the invention. Dosing information relevant to the systemic drug delivery method of the invention is described separately in the portion of the present disclosure which describes that method.

Various dosage forms may be made which comprise a local anesthetic at a concentration of about 0.01% to about 53% by weight, preferably a concentration of about 0.25% to about 10% by weight, more preferably about 0.5% to about 5% by weight, and even more preferably at about 2.5% by weight. The pharmaceutical composition should be formulated to deliver about 10 micrograms to about 2.5 grams of the local anesthetic to each nostril of a patient, and preferably to deliver about 10 micrograms to about 1 gram. Unit dosage forms containing an amount of the pharmaceutical composition in these ranges may be used. When the pharmaceutical composition is in the form of a liquid for topical application (e.g., a spray), a dose of the pharmaceutical composition may be contained, for example in a volume of about 0.5 milliliters to about 5 milliliters, and preferably in a volume of about 1 milliliter to about 3 milliliters, for delivery to each nostril. Such liquid pharmaceutical compositions preferably contain the local anesthetic at a concentration of about 0.01% to about 20% (w/v), more preferably about 0.25% to about 5% (w/v). When the pharmaceutical composition is in the form of a solid, semi-solid, gel, foam, mousse, creme, emulsion, or the like, the pharmaceutical composition may be formulated to contain about 10 micrograms to about 2.5 grams of the local anesthetic to the patient per nostril in a volume of about 0.5 milliliters to about the capacity of the nasal cavity. In one embodiment, the local anesthetic is dorsonasally administered in a total amount from about 1 milligram to about 70 milligrams (although this amount may alternatively be administered to each nostril), and preferably in an amount from about 10 micrograms to about 50 milligrams. The concentration of the local anesthetic in the solid, semi-solid, gel, foam, mousse, creme, or emulsion form is preferably about 0.1% to about 53% (w/w), more preferably about 0.2% to about 20% (w/w).

A bulk form of a long-acting local anesthetic pharmaceutical composition may be made and administered to a patient in one or more doses which comprise the dosage amounts described in the preceding paragraph.

Pharmaceutical Compositions

The long-acting local anesthetic pharmaceutical composition that is useful in the methods of the invention may be intranasally or dorsonasally administered in a variety of formulations that can be made readily by one of skill in the art of pharmacology in view of the present disclosure. Formulations which are useful for intranasal administration of the pharmaceutical composition of the invention include, but are not limited to, jelly, creme, gel, foam, mousse, semi-solid, emulsion, sol-gel, foam, a eutectic mixture, liquid, droplet, aerosol, powder, microsomes, liposome, sustained release, degradable polymer, polymer microspheres, impregnated film, fiber, or patch, coated film, fiber, or patch, and other similar dosage forms. The pharmaceutical composition of the invention may contain one or more than one local anesthetic agent. When the pharmaceutical composition contains more than one local anesthetic agent, the agents may be mixed in substantially any ratio such as, for example, a eutectic ratio as described in U.S. Pat. No. 4,562,060. Eutectic mixtures of local anesthetics can be rapidly and more easily taken up by submucosal structures such as nerves, and thus are useful for submucosal nerve block. In addition, levo local anesthetics are vasoconstrictors. Eutectic mixtures of a local anesthetic with a vasoconstricting agent (e.g., a levo local anesthetic) can exhibit prolonged local anesthetic activity and reduced systemic uptake relative to non-eutectic mixtures of the same local anesthetic.

In addition to the local anesthetic, such pharmaceutical compositions may contain pharmaceutically acceptable carriers and other ingredients known to enhance and facilitate drug administration with the additional pharmaceutical agents disclosed herein. Compounds, formulations, and dosages of the additional pharmaceutically active agents described in this method are known in the art. Owing, in part, to the vasodilatory activity of local anesthetics, these compounds may be used according to this method at doses of about half their art-recognized doses to their full art-recognized doses.

Such pharmaceutical compositions may also contain ingredients to enhance sensory acceptability of the composition to a human patient, such as aromatic, aromatherapeutic, or pleasant-tasting substances. The pharmaceutical compositions may also, for example, be made in the form of a flexible solid or semisolid carrier comprising the local anesthetic, such as one of the carriers described in U.S. Pat. No. 5,332,576 or in U.S. Pat. No. 5,234,957; or in the form of suspended microspheres, such as those described in U.S. Pat. No. 5,227,165. Solid and semi-solid formulations of a shorter-acting, a long-acting, or a persistent local anesthetic are preferred in the compositions, methods, and kits of the inventions, because such preparations improve local anesthetic localization. In these forms, there is less dilution of the local anesthetic by body fluids and less transport of the local anesthetic to an unintended body location. Furthermore, it is believed that these formulations will reduce or minimize unintended side effects such as disagreeable taste, oropharyngeal numbness, dysphasia, and compromise of protective reflexes. In these formulations, a lower amount of local anesthetic may be used, relative to other formulations.

Numerous pharmaceutically acceptable carriers are known in the art, as are methods of combining such carriers with local anesthetics. Examples of such carriers and methods are described, for example, in Genaro, ed., 1985, Remington's Pharmaceutical Sciences, Mack Publishing Co., Easton, Pa.

It is understood that the pharmaceutical composition of the invention may comprise a combination of any of the forms described herein. By way of example, microparticles, microsomes, or liposomes comprising a local anesthetic may be suspended in a solution or other formulation of the same or a different local anesthetic, whereby the solution or other formulation provides a rapid onset of anesthesia and the local anesthetic in the form of microparticles, microsomes, or liposomes provides a sustained duration of anesthesia. Sustained release preparations may comprise a slowly-released formulation of a local anesthetic. Inclusion of another local anesthetic in such formulations, in a free or salt (i.e., not slowly-released) form confers to the formulation the ability to act both with a rapid onset of anesthesia and a sustained duration of anesthesia. All such combinations of formulations described herein are included in the invention.

The long-acting local anesthetic pharmaceutical composition useful for practicing the invention must be administered in a dose sufficient to inhibit the CNvD for at least about one hour, and preferably for at least about two hours. Doses of the long-acting local anesthetic pharmaceutical composition may be administered in a single dose, in multiple doses, in sustained release doses, or continuously.

The local anesthetic(s) may be present in the pharmaceutical composition at any concentration from a very dilute concentration through the solubility limit of the local anesthetic in the medium in which it is delivered. The local anesthetic(s) may also be present at a concentration greater than the solubility limit of the local anesthetic in the medium in which it is delivered by using a crystalline, microcrystalline, or amorphous solid form of the local anesthetic, preferably suspended in a gel, foam, mousse, creme, liquid, liposome, microsome, solid polymeric matrix, or the like. In various embodiments, the local anesthetic may be administered in the form of a eutectic mixture of local anesthetics, such as described in U.S. Pat. No. 4,562,060, in the form of encapsulated or embedded local anesthetic, such as described in U.S. Pat. No. 5,085,868, in the form of an oil-in-water emulsion, such as described in U.S. Pat. No. 5,660,837, or in the form of an emulsion, a creme, a eutectic mixture, or a microemulsion, such as described in International Patent Application Publication No. WO 97/38675, particularly one having thermoreversible gelling properties. Because the nasal cavity is normally cooler than gum pockets, the environment disclosed in International Patent Application Publication No. WO 97/38675, a composition having thermoreversible gelling properties, wherein the composition is a fluid at about 20° C. and a gel or semi-solid at the temperature in the human nasal cavity (i.e., about 30-37° C.), is preferred. Any of these compositions may be conveniently delivered dorsonasally and, once so delivered, will be available where placed within the nasal cavity for a sustained period after administration and will spread or drip into other tissues to a lesser degree than would a liquid composition. By using one of these formulations, less of the active compound yields greater therapeutic results and has significantly decreased side effects, such as local and systemic toxicity, tongue and oropharyngeal numbness, discomfort, bad taste, dysphasia, and possible compromise of protective airway reflexes.

Other possible formulations may be made by of one of skill in the art of pharmacology in view of this disclosure without departing from the spirit of the invention. See, for example, (Genaro, ed., 1985, Remington's Pharmaceutical Sciences, Mack Publishing Co., Easton, Pa.) for a number of forms of typical pharmaceutical compositions that may be adapted readily to the present invention in view of this disclosure.

Co-Administration of a Local Anesthetic with Another Migraine or Muscular Headache Therapeutic Agent Numerous pharmaceutically active agents are thought to exhibit their limited therapeutic activity by virtue of the ability of the agent to interact with one or more receptors present on the surface of cerebral blood vessels or other structures. By way of example, migraine therapeutic agents known as serotonin receptor agonists include such agents as sumatriptan and zolmitriptan, and are believed to interact with serotonin receptors. In order to exhibit their pharmacological effects, such agents must gain access by systemic vascular delivery to cerebral blood vessels which have altered vascular flow during an acute migraine episode (Scott, 1994, Clin. Pharmacokinet. 27:337-344) and must achieve a critical concentration at the cerebrovascular location of the corresponding receptor(s) in the compromised area. Thus, these pharmaceutically active agents must be administered at the onset of an acute migraine episode in order to avoid the cascade of inflammation that follows initiation of the episode (Limmroth et al., 1996, Curr. Opin. Neurol. 9:206-210). Following delivery of one of these agents to the compromised area of a cerebral blood vessel, the concentration of the drug gradually decreases at those sites, and rebound can occur.

Topical local anesthetics are vasodilators and therefore inhibit vasoconstriction, with the exceptions of cocaine, which is a vasoconstrictor. It is believed that the vasodilatory effects of topical local anesthetic administration results from both a direct effect of the anesthetic upon the affected blood vessel and from an indirect effect of the anesthetic upon nerve structures associated with the blood vessel.

In normal states, most blood vessels, particularly those of smaller diameter, do not transport blood because they are not open, due to constriction of blood vessels located proximal thereto with respect to the heart or due to increased muscle tone in the blood vessel wall itself. Should these vessels open at once, profound hypotension would develop immediately, resulting in shock. Many and complex mechanisms are involved in the regulation of blood vessel tone and blood circulation. Hence, in any given tissue or organ, many blood vessels are closed. Blood vessel recruitment refers to a process whereby closed or partially constricted blood vessels are opened or dilated. This increases the number and surface area of blood vessels available for uptake and allows greater blood flow through these vessels. The latter mechanism increases drug transport away, and this decreases local blood drug concentration, favoring drug diffusion into the blood. All of these mechanisms increase drug uptake and transport. Surface vasodilation effected by an intranasally or dorsonasally administered local anesthetic other than cocaine promotes greater blood vessel recruitment and therefore, greater systemic uptake of the pharmaceutically active agent administered in conjunction with the local anesthetic. Hence, co-administration of a local anesthetic and a pharmaceutically active agent results in a more rapid and greater systemic uptake of the pharmaceutically active agent. This produces a more rapid and greater concentration of the pharmaceutically active agent at the affected site.

Furthermore, vasodilation of arterial structures which pass through the intranasal mucosa to feed other relevant neural structures will result in increased delivery of intranasally administered pharmaceutically active agents directly to target sites, especially if arterial blood flows through an area to which the agent and anesthetic are administered. For example, the sphenopalatine artery provides blood supply to much of the middle turbinate of the human nose, to the region of the nasal epithelium overlying the SPG, and to the SPG. Without wishing to be bound by any particular theory, it is believed that the anesthetizing effect of local anesthetics such as bupivacaine induces vasodilation of arterial structures coursing through local tissue on the way to the brain and other relevant neural structures, and increases agent delivery. Additionally, the decreased extracranial and intracranial vasospasm and vasodilation which result from anesthesia of the SPG increases blood flow to relevant structures and therefore increases drug delivery to relevant tissues even further. Hence, intranasal administration of local anesthetic(s) induces both local and intracranial vasodilation and decreases or prevents vasoconstriction caused by normal autoregulatory processes, by neurally mediated processes, or by release of neurotransmitters, neuropeptides, or other factors which are associated with an acute CNvD or muscular headache. Thus, administration of a local anesthetic to the region of the nasal epithelium overlying the SPG and to other regions of the epithelium located nearby facilitates transport of a pharmaceutically active agent from the surface of the nasal epithelium directly into relevant venous, capillary, and arterial vessels and into the general systemic circulation where intracranial vasodilation or decreased vasospasm results in increased active agent delivery to sites at which it exhibits its pharmaceutical activity.

Therefore, it is anticipated that dorsonasal delivery of a composition which comprises a long-acting or persistent local anesthetic and a pharmaceutically active agent will result in greater local delivery of the agent to a cerebral neurovascular tissue than could be achieved by dorsonasal delivery of the agent alone.

Furthermore, if agents, such as sumatriptan and ropivacaine, for example, are believed to have different mechanisms of action, it is believed that the therapeutic effects of the two compounds will be pharmacodynamically synergistic, or at least additive. This is yet another manner that co-administration of a local anesthetic and another pharmaceutical agent is advantageous.

Without wishing to be bound by any particular theory of operation, it is believed that the co-administered compositions inhibit the headache and diminish the likelihood that the headache will rebound or recur. This is believed to be especially true for patients who are afflicted with a plurality of distinct headaches or patients who experience separate headache triggers in series.

The present invention includes a method of inhibiting a neurovascular or muscular headache in a human patient, the method comprising intranasally, and preferably dorsonasally, administering to the patient a composition comprising at least one local anesthetic and a pharmaceutically active agent effective for treatment of the headache. Preferably, the local anesthetic is a long-acting local anesthetic, a persistent local anesthetic, or a sustained release formulation of a local anesthetic other than cocaine, whereby intranasal, and preferably dorsonasal, administration of the composition results in improved uptake of the pharmaceutically active agent by a cerebral neurovascular tissue of the patient and to enhancement of the pharmaceutical activity of the agent.

By way of example, when the headache is a migraine, compositions for inhibiting the migraine and co-administering a migraine therapeutic agent include a sustained release formulation of a composition comprising sumatriptan (e.g., IMITREX™, Glaxo-Wellcome Inc., Research Triangle, N.C.) and lidocaine, a composition comprising zolmitriptan (e.g., ZOMIG™, Zeneca Pharmaceuticals, Wilmington, Del.) and bupivacaine, a composition comprising rizatriptan (e.g., MAXALT™, Merck & Co., West Point, Pa.) and ropivacaine, a composition comprising naratriptan (e.g., NARAMIG™, Glaxo-Wellcome Inc., Research Triangle, N.C.) and tetracaine, and a composition comprising a beta blocker and etidocaine.

Further by way of example, when the headache is a muscular headache, compositions for inhibiting the muscular headache and co-administering a muscular headache therapeutic agent include compositions comprising a local anesthetic ingredient selected from the group consisting of a persistent local anesthetic, a long-acting local anesthetic, and a sustained release formulation of a local anesthetic and an additional pharmaceutically active agent selected from the group consisting of a vasoconstrictor, epinephrine, norepinephrine, phenylephrine, methysergide, propanolol, a calcium channel blocker, verapamil, ergot, an ergotamine preparation, dihydroergotamine, a serotonin agonist, sumatriptan, zolmitriptan, rizatriptan, naratriptan, a chroman compound, aspirin, acetaminophen, a non-steroidal anti-inflammatory drug, caffeine, a narcotic, butorphanol tartrate, meperidine, a mast cell degranulation inhibitor, cromolyn sodium, eucalyptol, tetrodotoxin, desoxytetrodotoxin, saxitoxin, an organic acid, a sulfite salt, an acid salt, a glucocorticoid compound, a steroid ester, magnesium or lithium ions, a centrally-acting analgesic, a beta blocker, an agent that increases cerebral levels of gamma-aminobutyric acid, butalbital, a benzodiazepine, valproat, gabapentin, divalproex sodium, a tri-cyclic antidepressant, a narcotic analgesic, an oral muscle relaxant, a tranquilizer, a muscle relaxant, and another compound.

The local anesthetic compounds, formulations, dosages, and methods of administration which are useful for this method of the invention are substantially the same as those described herein with respect to inhibiting a neurovascular headache, a muscular headache, or a CNvD. Compounds, formulations, and dosages of the other pharmaceutically active agents described in this method are known in the art. Owing, in part, to the vasodilatory activity of local anesthetics, these compounds may be used according to this method at doses of about half their art-recognized doses to their full art-recognized doses.

The composition may comprise a local anesthetic and a pharmaceutically active agent which is effective for treating a CNvD or a muscular headache. By way of example, such a composition may comprise ropivacaine and an additional ingredient. The additional ingredient may, for example, be a serotonin receptor agonist, including, but not limited to, a triptan, e.g., sumatriptan or a chroman compound such as one of the compounds described in U.S. Pat. Nos. 5,387,587; 5,420,151; 5,639,772; and 5,656,657, a non-steroidal anti-inflammatory drug, an anti-emetic, or a mast cell degranulation inhibitor such as cromolyn sodium.

In addition, the composition may comprise an agent which increases or prolongs either or both of the anesthetic effect and the tissue uptake of the local anesthetic. Such agents include, for example, an n-glycofurol compound, such as one of the compounds described in U.S. Pat. No. 5,428,006, eucalyptol, a toxin such as tetrodotoxin, desoxytetrodotoxin, or saxitoxin, an organic acid, a sulfite salt, an acid salt, magnesium or lithium ions, and a centrally-acting analgesic.

In addition, the composition may be a combination of a beta blocker and a local anesthetic, as described, for example, in European Patent No. 754060. The agent may also be a drug that increases cerebral levels of gamma-aminobutyric acid (GABA), either by increasing GABA synthesis or decreasing GABA breakdown. Such GABA-affecting agents include, for example, butalbital, benzodiazepines, valproat, gabapentin, and divalproex sodium. The agent may also be an agent effective for treatment or prevention of neurodegenerative disorders such as, for example, (S)-alpha-phenyl-2-pyridineethanamine (S)-malate, as described in European Patent No. 970813. Furthermore, the agent may be a compound which decreases inflammation, including, for example, a glucocorticoid compound such as a steroid ester. Compounds, formulations, and dosages of vasoconstrictors and other pharmaceutically active agents described in this method are known in the art. Owing, in part, to the vasodilatory activity of local anesthetics, each of these compounds may be used according to this method at doses of about half their art-recognized doses to their full art-recognized doses.

In a patient refractory to monotherapy or treatment using a local anesthetic composition comprising only one additional compound, the composition may be combined with one, two, or more additional compounds, and this combined composition may prove to have therapeutic effects which are synergistic, or at least additive, with respect to each of the individual ingredients. By way of example, such a combined composition may comprise a long-acting or persistent local anesthetic, a beta-blocker, and a serotonin receptor agonist. Other examples include a combined composition comprising a long-acting or persistent local anesthetic and an anti-epileptic compounds such as phenyloin sodium (e.g., Dilantin®, Parke-Davis, Morris Plains, N.J.), a combined composition comprising a long-acting or persistent local anesthetic and a serotonin receptor agonist, a serotonin subclass 5HT1F receptor agonist, LY334,370, and a combined composition comprising a long-acting or persistent local anesthetic and a sesquiterpene lactone (e.g., a compound such as parthanolide, obtained from an herb such as feverfew {Tanacetum parthenium}).

Methods of Effecting Intranasal or Dorsonasal Administration

Intranasal administration of a composition may be effected by any method by which the composition is provided to any portion of the nasal epithelium. Intranasal administration of a composition comprising a local anesthetic according to certain methods of the invention is preferably effected by dorsonasal administration of the local anesthetic.

Dorsonasal administration of a pharmaceutical composition may be effected by any method or route which results in delivery of the composition to a tissue, fluid, or surface of a human, whereby a component of the composition is provided to a DnNS either directly or by diffusion through tissue or fluid interposed between the DnNS and the site of administration. For example, dorsonasal administration of a composition comprising a local anesthetic may be effected by injecting a composition directly into a DnNS or by topically applying the composition to a tissue located in close anatomic proximity to the SPG, whereby the local anesthetic is capable of diffusing from the tissue to a DnNS such as the SPG. Topical dorsonasal administration may be accomplished by an intranasal route or by an oropharyngeal route, for example. As described herein, nasal drip methods, nasal spray application methods, and mechanical application methods may be used to effect topical dorsonasal administration of a composition comprising a local anesthetic.

Intranasal administration of the composition of the invention may be improved if the nasal cavity is rinsed, treated with a decongestant, or otherwise cleared of material which might impede intranasal delivery prior to administration of the composition.

As described herein in Example 1, dorsonasal administration of ropivacaine to patients afflicted with migraine using an intranasal spray method, an intranasal drip method, or an intranasal cotton swab method yielded different response rates and different values for the efficacy of ropivacaine for relief of migraine. Although drip and spray methods resulted in wider ropivacaine distribution within the nasal cavity, direct application of ropivacaine to the region of the nasal epithelium overlying the SPG using a cotton swab yielded the most rapid and most effective inhibition of migraine.

The pharmaceutical composition that is useful in the methods of the invention may be administered topically in the types of formulations noted herein. Intranasal, and preferably dorsonasal, administration of the composition may be achieved by providing a mist or aerosol spray comprising the composition to the nasal cavity via the nostril, by providing drops or a stream of liquid comprising the composition to the nasal cavity via the nostril or by injection of the liquid using a hypodermic needle which penetrates the facial skin of the patient, by directly applying the composition dorsonasally using a flexible or anatomically-shaped applicator inserted through the nose or mouth of the patient, including an applicator or implant which is left in place over a period of time, by introducing into the nasal cavity a liquid, gel, semi-solid, powder, or foam comprising the composition, or by any other means known to one of skill in the art of pharmaceutical delivery in view of this disclosure.

Intranasal, and preferably dorsonasal, administration of a pharmaceutical composition to a human has distinct advantages relative to other routes of administration. By administering a composition intranasally or dorsonasally, a high local concentration of the composition in a relevant neural structure, and possibly in the cerebral neurovasculature, may be achieved relative to the systemic concentration of the composition. Local delivery is advantageous in situations in which systemic exposure to the composition is undesirable, either because the composition is metabolized systemically or because systemic exposure results in harmful symptoms. By way of example, systemic administration of a local anesthetic such as bupivacaine is undesirable because bupivacaine is metabolized in the liver and because systemic administration of a relatively large amount of bupivacaine is known to cause serious adverse effects.

Another advantage of intranasal or dorsonasal administration of a compound, at least where local cerebral neurovascular delivery is desired, is that a lesser amount of drug may be administered than would be necessary to administer via a different route. Absorption of intranasally or dorsonasally delivered drug into cerebral neurovascular tissue enables the patient to avoid digestive or at least some hepatic drug metabolism which could occur, for instance, if the drug were administered orally. Furthermore, intranasal or dorsonasal delivery of a drug requires less intensive intervention by a medical professional than some other delivery methods, such as intravenous delivery. Self-medication by an intranasal or dorsonasal route is practical, as evidenced by the many nasal and pulmonary delivery devices and drug formulations which are commercially available.

DnNSs may not be directly accessible via the nasal cavity. However, because of the anatomic proximity of DnNSs to the nasal epithelium, anesthesia of a DnNS can be effected by topical administration of a local anesthetic to the region of the nasal epithelium overlying the SPG or to the region of the nasal epithelium near that region. For example, within the nasal cavity, the SPG lies dorsal to the posterior tip of the middle concha, and is covered by the nasal epithelium at a variable depth of one to nine millimeters (Sluder, 1908, N.Y. State J. Med. 27:8-13; Sluder, 1909, N.Y. State J. Med. 28:293-298). Thus, a compound applied to the surface of the nasal epithelium at or near the region of the nasal epithelium overlying the SPG, such as the surface of the nasal epithelium dorsal to the posterior tip of the middle concha can diffuse through the epithelium and any intervening tissue or fluid to reach the SPG.

The SPG, which is sometimes designated the pterygopalatine ganglion, is located in the pterygopalatine fossa of the human skull, close to the sphenopalatine foramen and close to the pterygoid canal. The SPG is situated below the maxillary nerve where the maxillary nerve crosses the pterygopalatine fossa. Although it is also connected functionally with the facial nerve, the SPG is intimately related with the maxillary division of the trigeminal nerve and its branches. The parasympathetic root of the SPG is formed by the nerve of the pterygoid canal, which enters the SPG posteriorly. The fibers of the parasympathetic root of the SPG are believed to arise from a special lacrimatory nucleus in the lower part of the pons and run in the sensory root of the facial nerve and its greater petrosal branch before the latter unites with the deep petrosal branch to form the nerve of the pterygoid canal. The sympathetic root of the SPG is also incorporated in the nerve of the pterygoid canal. The fibers of the sympathetic root of the SPG are postganglionic, arise in the superior cervical ganglion, and travel in the internal carotid plexus and the deep petrosal nerve. The vidian nerve is located in close proximity to the SPG, and the efficacy of local anesthetics for inhibiting an acute CNvD may arise, in whole or in part, from anesthesia of the vidian nerve or another DnNS located in close anatomic proximity to the SPG. It is also known that the trigeminal nerve has anatomical and functional relationship(s) to cervical nerve 2. Other DnNSs which are located in close anatomic proximity to the SPG include, but are not limited to, the cavernous sinus ganglion, the carotid sinus ganglion, numerous branches of the maxillary nerve, the ethmoidal nerve, and the ethmoidal ganglion.

The ability of a compound to diffuse from the surface of the nasal epithelium to a DnNS such as the SPG depends, of course, on the ability of the compound to diffuse through bodily tissues and fluids. Thus, compounds to be delivered to a DnNS by topical application to the nasal epithelium are preferably diffusible through both aqueous solutions and lipids.

Local anesthetics which are related to the class of local anesthetics designated aminoacyl local anesthetics exhibit both suitable aqueous solubility and suitable lipid solubility for use in the methods of the invention. It is believed that such local anesthetics are able to diffuse into nerves in their neutral, uncharged state, and that such local anesthetics assume their pharmacologically active, charged state within nerve cells.

In the case of delivery of a local anesthetic to a DnNS such as the SPG via topical application of the anesthetic to the nasal epithelium, it is preferable that the anesthetic be sufficiently diffusible through bodily tissues and fluids and have a sufficiently long half-life in vivo that the anesthetic is able to diffuse from the epithelium to the DnNS in an amount and for a duration sufficient to anesthetize the DnNS or otherwise inhibit the physiological processes that result in one or more symptoms of the CNvD, such as a period on the order of at least about one hour, and preferably at least about two hours. On the other hand, the diffusivity through bodily tissues and fluids and the in vivo half-life of the anesthetic must not be so high and long, respectively, that the anesthetic is delivered systemically in an amount sufficient to cause the adverse effects known to be associated with systemic administration of local anesthetics (see, e.g., Physician's Desk Reference®, Medical Economics Co., Inc., Montvale, N.J., 51st ed., 1997, pp. 424-427).

Apparatus for Intranasal or Dorsonasal Administration of a Composition

Particularly contemplated apparatus for intranasal or dorsonasal delivery of a composition to a human patient according to the methods of the invention include, but are not limited to, an anatomically-shaped applicator, a metered dose dispenser, a non-metered dose dispenser, a squeezable dispenser, a pump dispenser, a spray dispenser, a foam dispenser, a powder dispenser, an aerosol dispenser, a dispenser containing a propellant, an inhalation dispenser, a patch comprising the composition, an implant comprising the composition, a soft pipette with an elastomeric bulb in fluid communication with a reservoir containing the composition, a dropper for directing the composition past the conchae of the patient to an intranasal nerve structure (InNS, including a DnNS, but not limited to DnNSs), or intranasal blood vessel (InBV), a swab having an absorbent portion impregnated with the composition, a swab having an anatomically-shaped portion comprising an absorbent portion impregnated with the composition, and a swab having a compressed absorbent portion in fluid communication with a reservoir containing the composition. An anatomically-shaped applicator is one which has a shape which permits insertion of the applicator into the nose or mouth of a human and which enables contact of the composition delivered by the applicator with the surface of the region of the nasal epithelium overlying the InNS or with a surface of the nasal epithelium near the region of the nasal epithelium overlying the InNS (e.g., a DnNS such as the SPG). It is preferred that the shape and/or materials of the apparatus be selected for comfortable insertion or application via an intranasal route. The apparatus preferably is adapted to contact either a superior portion of the nasal epithelium or a portion of the nasal epithelium that overlies a DnNS.

Another embodiment of an apparatus for intranasal or dorsonasal delivery of a pharmaceutical composition of the invention comprises a body having a plurality of passages through which a composition may be delivered. The device may be designed so that the pharmaceutical composition of the invention is delivered through each passage, the passages being individually or collectively connected to, for example, a plurality of orifices in an anatomically-shaped applicator whereby the orifices direct delivery of the composition to a plurality of locations within the nasal cavity when the applicator is inserted into the nose of a patient and operated. The device may alternately be designed so that the pharmaceutical composition of the invention is delivered through one or more passages and an additional pharmaceutically active agent is delivered through the same passages or through one or more different passages. Alternately, the device may comprise components of the pharmaceutical composition of the invention which are separately delivered through one or more passages of the device and mixed either in a passage of the device or in the nasal cavity of the patient.

Devices which contain, deliver, or produce a semi-solid long-acting local anesthetic composition are contemplated. To use one of these devices, an outlet of the device is situated in fluid communication with one of or both of the nostrils of a patient. A solid, foam, semi-solid, foam-forming fluid, or another fluid which exhibits an increase in viscosity upon administration, such as one of the type known in the art, is provided to the outlet, whereby it passes into the nostril of the patient, filling or partially filling the nasal cavity. A local anesthetic in the composition contacts the walls of the nasal cavity, preferably in a dorsonasal location, and the local anesthetic is thereby administered to the patient. The devices described herein can be used to deliver substantially any composition or material to the portion(s) of the nasal epithelium for which they are adapted.

Directed Intranasal Drug Delivery Devices

There are several known devices for effecting intranasal delivery of a drug or other non-gaseous pharmaceutically acceptable preparation. Such devices include, for example, liquid-containing squeeze bottles, liquid-containing pressurized containers, liquid-containing pump-type containers, droppers, microfine powder dispersers, and nebulizers. Although each of these prior art devices may be used to intranasally administer a pharmaceutical composition (e.g., according to any of the methods described herein), each of these devices has certain drawbacks and shortcomings which make their use for directed intranasal administration of compositions (e.g., for dorsonasal administration) sub-optimal.

Liquid-containing squeeze bottles dispense atomized liquid upon pressurization of the bottle effected by squeezing. However, the amount of liquid expelled upon squeezing, the direction in which the liquid is expelled, and the velocity at which it is expelled can vary quite considerably based on how the user manipulates the device. Furthermore, the degree of atomization (i.e., the size of the droplets) may depend on the force applied to the container.

Liquid-containing manual pump-type containers dispense atomized liquid upon actuation by the user of a pump mechanism, in which displacement of a portion of the container along a vertical axis of the container causes atomized liquid to be expelled from a second portion of the container, generally in a direction parallel to the longitudinal axis of the container. By inserting the second portion into a nostril and actuating the pump, a stream or mist of atomized liquid is expelled into the nostril. These devices, like the other prior art devices, exhibit significant variability in the direction in which the liquid is expelled, owing to variation in the positioning of the device by the user. Furthermore, because these devices are operated by applying pressure to the device in a direction toward the interior of the nostril, these devices are uncomfortable and present the possibility of injury due to accidental excessive applied force or misplacement by the distressed user.

Liquid-containing pressurized containers dispense atomized liquid upon manipulation by the patient of a triggering mechanism. For example, many such devices comprise a valve through which atomized or liquid medication is expelled upon depressing a trigger or other actuator to open the valve. Although these containers may exhibit improved control over the amount and velocity of expelled fluid, relative to squeeze bottles, the intranasal direction in which the liquid is delivered depends heavily on actions of the user.

Droppers, pipettes, and other bulk liquid instillation devices share the drawback that either the patient must remain in an awkward position (e.g., lying on the back, with the head propped up and to one side) in order to retain the liquid in the nasal cavity for an appreciable period or, alternatively, that administration must be repeated numerous times, owing to rapid drainage of the liquid from the nasal cavity. In addition, instillation of bulk liquid into the nasal cavity presents the risk that the liquid will be inhaled by the patient into the lungs or passed through the nasopharynx into the esophagus and digestive system. This increases uncomfortable numbness and potentially compromises protective airway and swallowing reflexes. Furthermore, increased wastage leads to increased systemic levels of drug and decreased desired local effects.

Microfine powder dispersers and nebulizers may be used to deliver powders and atomized liquids, respectively, to the nasal epithelium, but share a number of drawbacks. First of all, the pattern of delivery will largely parallel the pattern of inhalative air flow through the nasal cavity, and therefore may not distribute the agent evenly to the nasal epithelium, particularly to more remote regions, such as the dorsonasal region or a superior portion of the nasal epithelium. Second of all, a significant portion of inhaled powder and mist bypasses the nasal epithelium altogether, and instead is carried, along with bulk inhaled air, into the bronchi and lungs. When systemic delivery of a compound is desired, such bypass may be desirable. However, when local directed intranasal (e.g., dorsonasal) administration is desired, this bypass may frustrate effective delivery.

All of these prior art drug delivery devices share a common shortcoming. Each disperses the drug non-specifically to the nasal epithelium and does not target local areas such as those overlying a nerve structure (e.g., a portion of the nasal epithelium including or overlying a branch of an InNS such as the olfactory nerve or another DnNS such as the SPG, a ciliary blood vessel, or ciliary nerve), those overlying an intranasal blood vessel, or the nasal cavity orifices of the sinuses.

The shortcomings of the prior art drug delivery devices may be understood in view of the fact that directed administration of compositions to selected remote areas of the nasal epithelium (e.g., the dorsonasal region or a superior portion of the nasal epithelium) has not previously been demonstrated. Prior art intranasal drug delivery methods have generally taught administration to the largest possible portion of the intranasal epithelium, in order to provide the drug to much of the intranasal epithelium. In contrast, as described herein, several of the methods of the invention teach that dorsonasal, or other intranasally-targeted, administration of a pharmaceutical composition (e.g., a composition comprising a long-acting local anesthetic) may be preferable for a number of reasons. For example, in one embodiment, the method of inhibiting a cerebral neurovascular disorder described herein involves dorsonasally administering a long-acting local anesthetic pharmaceutical composition to a human. Intranasal administration of compositions to portions of the nasal epithelium overlying an InNS or an InBV can deliver a pharmaceutically-active (i.e., pharmacologically-active or biologically-active) agent to the InNS or InBV, or to another tissue that communicates therewith. For example, intranasal administration of a composition to a portion of the nasal epithelium overlying an InBV can be used to effect systemic administration (or local vascular delivery) of the agent, and intranasal administration of a composition to a portion of the nasal epithelium overlying an InNS can be used to effect delivery of the agent to another nerve structure (e.g., a cephalic ganglion, the spinal cord, or a portion of the brain) with which the InNS connects.

First, it is believed that the site at which long-acting local anesthetics have their biological effect may be physically located at or in close proximity to the portion of the nasal epithelium to which an intranasally administered composition is applied (i.e., as described elsewhere herein, for example, to the region of the nasal epithelium overlying the SPG for a dorsonasally administered local anesthetic); thus, dorsonasal administration may be preferable to general intranasal administration because it directs the pharmaceutically active agent to or near its site of action for treatment of migraine and headache.

Second, site-directed (e.g., dorsonasal) administration may be used to intentionally limit intranasal delivery of the biologically active agent to non-desired intranasal sites, thereby minimizing uptake of the biologically active agent into the bloodstream. This may be particularly important with biologically active agents (e.g., dextro-bupivacaine) which, at high bloodstream concentrations of the agent, have undesirable side-effects are used.

Third, because directed intranasal administration limits uptake of the administered agent into the bloodstream, the agent may be delivered (e.g., to a dorsonasal nerve structure) more frequently and at a higher concentration or greater amount than it could if it were administered in a more anatomically diffuse way. Therefore, high concentrations of the agent may be achieved in a tissue (e.g., the SPG, cerebrospinal fluid, or a brain or other CNS structure) located at or in close proximity to the dorsonasal epithelium. When the agent has a biological activity which decreases over time (e.g., a local anesthetic), administration of a high local concentration of the agent may prolong the duration of the intended biological effect.

Fourth, with intranasal administration of a compound having an uncomfortable, but non-harmful, side-effect (e.g., numbness), it may be preferable to limit the exposure to the compound to the type or the amount of tissue which exhibits the side effect by administering the compound only, or preferentially, to a selected portion of the nasal epithelium (e.g., dorsonasally), thereby limiting the side-effect upon non-targeted tissues.

Other advantages of directed intranasal administration, in contrast to general intranasal administration will also be understood by the skilled artisan in view of the present disclosure.

Figure 4A:
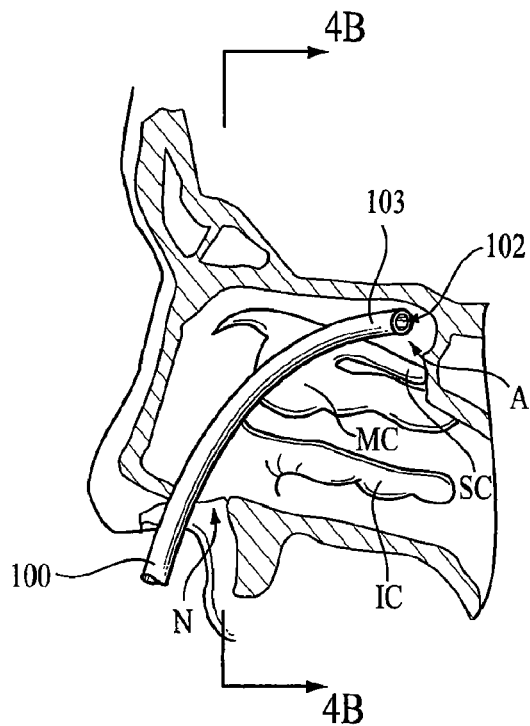
Figure 4B:
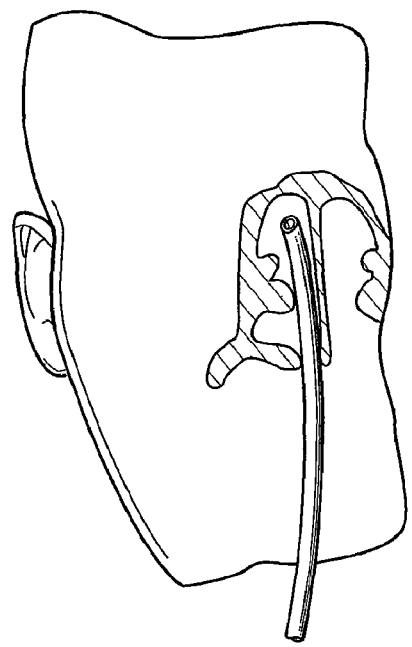
FIG. 4B is a diagram of a coronal section through the nose of a human taken along lines 4B-4B of FIG. 4A, illustrating the approximate placement of a dorsonasal delivery device of the invention in the nasal cavity.
Figure 4C:
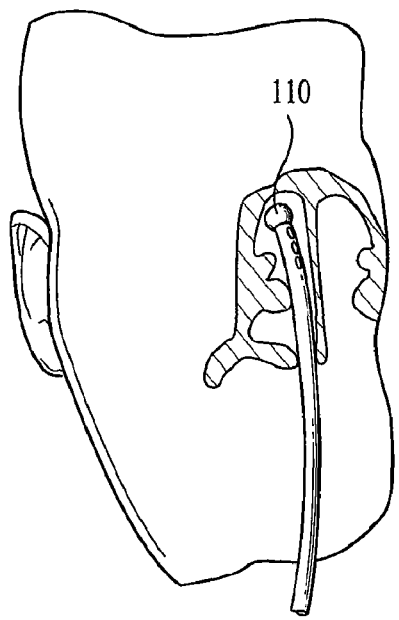
FIG. 4C is a diagram similar to FIG. 4B, but depicting an alternate embodiment of a dorsonasal delivery device of the present invention.
Figure 4F:
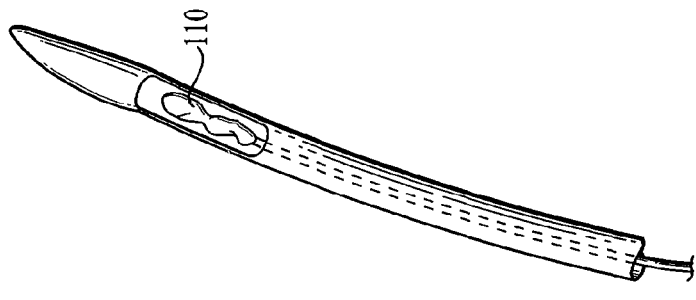
Figure 4E:
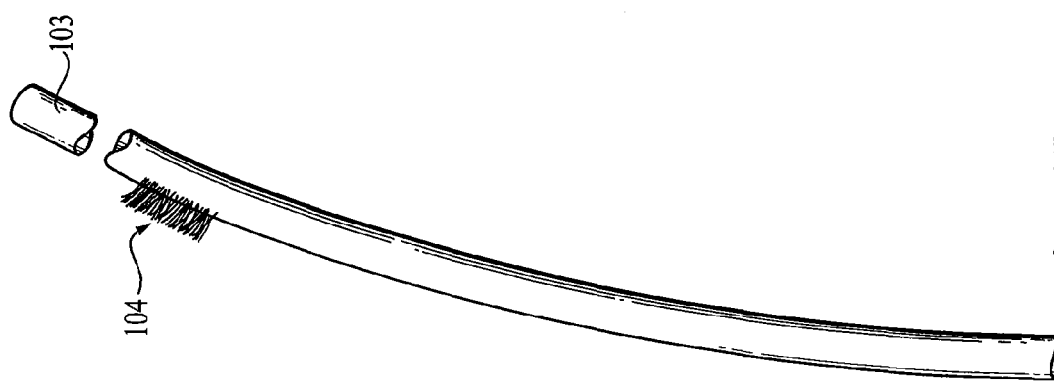
Figure 4D:
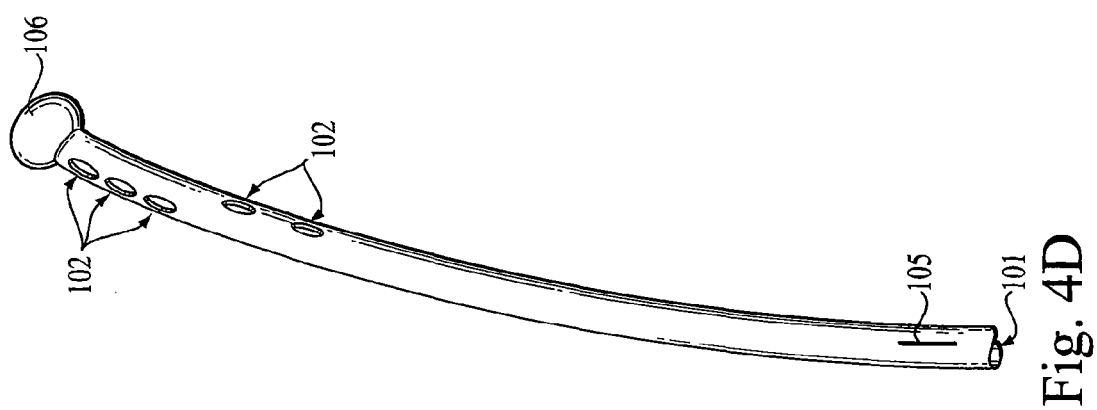

With reference to FIGS. 4A, 4B, and 4C, the invention includes an intranasal drug delivery device or applicator which comprises a body 100, preferably a generally elongate body such as a swab or a tube, which has a shape which conforms to the shape of the nasal cavity and has distal portion having a distal end 103. The distal portion of the elongate body may be inserted into the apex A of the nasal cavity, as illustrated in FIG. 4, without injuring the patient. The apex of the nasal cavity is the superior and posterior portion of the nasal cavity which lies posterior to the nasal septum and anterior to the sphenoethmoidal recess. The apex of the nasal cavity communicates with each of the nostrils, and the inferior IC, middle MC, and superior nasal conchae SC are situated in the passage from each nostril N to the apex. The elongate body may be substantially rigid or flexible, and is preferably flexible, in order to facilitate placement of the distal portion thereof in the apex of the nasal cavity.

When not inserted into the nasal cavity, the elongate body may have a generally curved or angled shape, wherein the longitudinal axis of the elongate body is angled at the distal end, with respect to the longitudinal axis at the proximal end. Preferably the angle defined by the intersection of the longitudinal axis at the distal end and the longitudinal axis at the proximal end is about 90 and about 170 degrees, more preferably about 110 and about 160 degrees or about 120 and about 150 degrees. The elongate body may be flexible along its entire length, or it may comprise one or more flexible or hinged sections, whereby the longitudinal axis of the distal end of the body may be deflected from the longitudinal axis at the proximal end.

In an alternative embodiment, the body is elongated, has an oval cross-section, is substantially straight, and has a lumen extending therethrough from the proximal end to the distal end. When the body is inserted into the nasal cavity, the distal end of the body extends above the nasal conchae, and the outlet port (i.e., at the distal end of the lumen) is positioned on the body such that the composition expelled from the outlet port is directed within the nasal cavity toward a selected surface of the nasal cavity, thus effecting directed intranasal administration of the composition. For example, the device can have one or more outlet ports that are positioned on the device such that when the device is inserted into the apex of the nasal cavity, a composition can be delivered through the lumen of the device dorsonasally, to a superior portion of the nasal epithelium, or both. The device can alternatively be used to direct administration of the composition to one or more other portions of the nasal cavity.

The shape of the intranasal delivery device may be envisioned as follows. It is preferably in the form of an elongate solid or hollow body, such as a tube, a flattened rod, or the like, that may be envisioned as lying on a plane surface. The body is bent or curved along the surface of the plane, either at one point, at several points along its length, or over its entire length, such that the longitudinal axis of the elongate body is angled at the distal end, with respect to the longitudinal axis at the proximal end, as described above. The body thereafter has a shape which conforms to the shape of a human nasal cavity. Optionally, the body may be further curved, again at one point, a plurality of points, or along its entire length, such that the distal end of the body is angled at an oblique angle with respect to the plane when the proximal end of the body is maintained in the plane.

One or more sections of the elongate body may be curved to facilitate insertion of the body past the nasal conchae, or to conform the shape of the body to the shape of the nasal cavity, in order that the body may rest more securely and comfortably in the nasal cavity after insertion.

With reference to FIGS. 4A-4K, the body 100, illustrated as the preferred elongate body, may have one or more lumens 101 extending from the proximal end thereof to one or more outlet ports 102 extending from the lumen to the exterior of the elongate body. The elongate body may have a substantially circular cross-section, an oval or flattened circular cross-section, a rounded rectangular cross section, a square cross-section, or substantially any other cross-sectional shape which is accommodated by the nostrils and nasal cavity of a human. The elongate body may have an indicium or indicia thereon or therein which indicate to the user the orientation of the distal end of the body with respect to the longitudinal axis of the body at the proximal end thereof. Alternatively, the proximal end of the body may have a curved portion having a fixed relationship with the distal end, whereby the orientation of the distal end of the body may be determined. Thus, a user can determine the orientation of the distal end 103 of the body 100 when it is emplaced within the nasal cavity of a patient by observing the position of the indicia 105 at the proximal end of the body. This may assist proper placement of the distal end of the applicator in the apex of the nasal cavity of the patient.

The outlet ports 102 may be located at the distal end 103 of the body 100 (i.e., as in FIGS. 4A and 4B), along the distal portion of the body (i.e., as in FIG. 4C), between the proximal and distal ends (i.e., as in FIG. 4D), or some combination thereof. Outlet ports may also be located substantially at one peripheral location relative to the elongate body (e.g., all on one side of a flattened elongate body), or they may be peripherally distributed around the perimeter of the body. The outlet ports may have any shape (e.g., round, square, a slit, etc.). One or more of the outlet ports may also be situated on the elongate body such that it will be occluded when the elongate body is placed within the nasal cavity of a patient. The body 100 may comprise a plurality of lumens 101, wherein certain outlet ports 102 communicate with one lumen, while others communicate with another lumen. Using such a device, a plurality of compositions may be administered to different sites within the nasal cavity. By way of example, the body may have a first lumen which communicates with a first set of outlet ports for dorsonasally administering a first composition to a patient and a second lumen which communicates with a second set of outlet ports for administering a second composition specifically to the nasal conchae or to a superior portion of the nasal epithelium. By administering the composition to one or more highly vascularized portions of the nasal epithelium or to a portion of the nasal epithelium overlying an InBV, the composition may be systemically administered to the patient.

The lumen(s) may be connected to a fluid-, gel-, or powder-containing reservoir, or a needle, probe, tube, or other elongate instrument 110 may be threaded through the lumen and, optionally, extended out of an outlet port 102. For example, the elongate instrument 110 can be maintained in a compressed state within the body 100 of the device during insertion of the device into a nostril, and can be expanded thereafter (e.g., upon engorgement with liquid agent provided, for example by way of the lumen 101, as illustrated in FIG. 4M). In various embodiments the elongate instrument may include a swab, rosette, balloon, etc. which is impregnated or coated with a pharmaceutically active composition and which is extended or inflated from the lumen through the outlet port following placement of the distal end of the elongate body in the apex of the nasal cavity (i.e., as in FIGS. 4F, 4G, and 4H). Such an extendable or inflatable elongate instrument 110 may optionally be retractable or deflatable. When the elongate instrument 110 is inflatable, it may be positioned on the device in such a way that it deflects a portion of the device upon inflation, as illustrated in FIG. 4G. An elongate instrument 110 can be tapered, as illustrated in FIG. 4N, to facilitate comfortable and minimally traumatic removal of the device from the subject's nostril. The elongate instrument may also be a solid or hollow needle which is coated with or which facilitates delivery of a pharmaceutically active composition (e.g., a local anesthetic) to a tissue located near the distal end of the elongate body (or near an outlet port 102) after placement of that distal end 103 in the apex of the nasal cavity. The hollow needle may be either sheathed or non-sheathed, and may, for example, either contain or communicate with a reservoir which contains a pharmaceutically active composition.

Figure 4J:
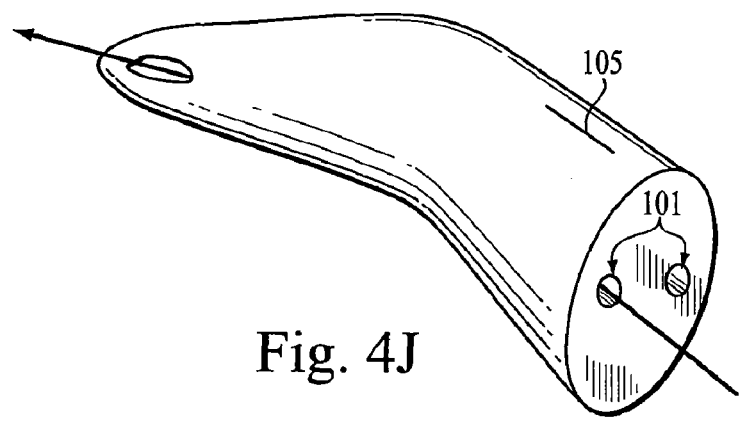
FIGS. 4J and 4K, respectively, are diagrams of left and right side views of a dual-lumen dorsonasal delivery device described herein.
Figure 4K:
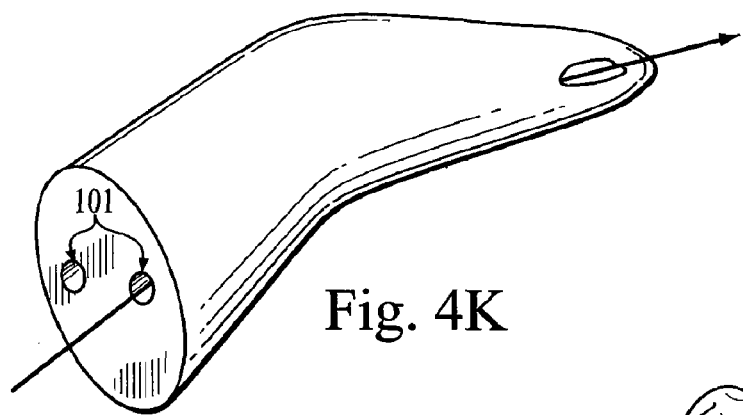
Figure 4L:
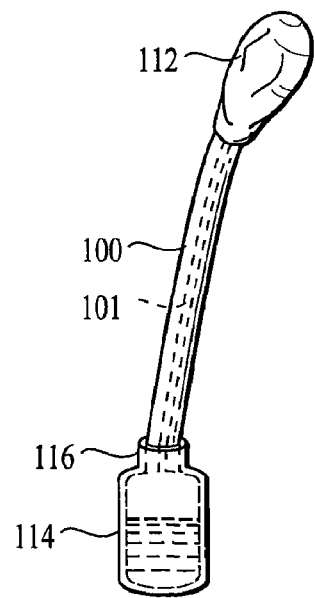

In one embodiment of the device/applicator, the elongate body has an angled shape, as illustrated in FIGS. 4J and 4K, an oval cross section, and two lumens 101 extending longitudinally therethrough from the proximal end to each of a pair of outlet ports located on the distal portion thereof. The two outlet ports are located on opposite faces of the distal portion of the body. The body has a shape which conforms to the shape of the nasal cavity on either side of the nasal septum. Therefore, this body may be inserted into either nostril of the patient in order to administer a composition dorsonasally to the patient. Furthermore, this embodiment of the applicator may further comprise a switching mechanism which permits the patient to select one of the two lumens for delivery of the composition, depending on the nostril into which the device is to be inserted. The switching mechanism may be associated with an excluder mechanism which blocks or inhibits insertion of the device into the non-selected nostril. Such an excluder mechanism may, for example, be an arm which is located beside the patient's nose on the side of the selected nostril when the device is inserted into the selected nostril, but which contacts the selected nostril in the event the patient attempts to insert the device into the non-selected nostril.

In another embodiment of this applicator, the body has one or more fibers embedded therein or passing through a lumen extending therethrough, whereby each fiber is fixed to the distal portion of the body and extends through the proximal end of the body. By pulling or twisting on a fiber, the pulling or twisting force may be imparted to the distal end of the body, thereby permitting the distal end to be "steered" to some degree by manipulation of the fiber(s).

A pharmaceutical composition may be delivered to a tissue (e.g., the SPG or a tissue overlying it) located near the distal end 103 of the body 100 after placement of that distal end in the apex of the nasal cavity either by providing the composition through a lumen 101 in the elongate body, as described above, or by applying the composition directly using the body. A pharmaceutical composition can also be delivered to tissues that are near an outlet port 102 when the device is emplaced in the nasal cavity (e.g., to the superior surface of the nasal cavity and to the upper face of the superior concha using the device shown in FIG. 4D). The applicator portion of the elongate body may be dipped in, constructed of, impregnated with, or coated with a composition comprising the pharmaceutical composition. Furthermore, the applicator portion may be in fluid communication (e.g., by way of a lumen 101 extending within the body 100) with a reservoir containing the pharmaceutical composition, whereby the composition may be provided from the reservoir to the applicator portion. For example, in the embodiment of the applicator depicted in FIG. 4L, a reservoir 114 is attached (or attachable, e.g., via a collar 116) to the body 100 such that a lumen 101 which extends through the body 100 places the contents of the reservoir 114 in fluid communication with an absorbent portion 112 associated with (e.g., attached to, initially compressed within, or both) the opposite end of the body 100. Thus, the contents of the reservoir 114 can be absorbed by the absorbent portion 112, for example upon inverting the device or upon squeezing the reservoir 114. Direct contact of the applicator portion of the elongate body and a portion of the nasal epithelium situated in the apex of the nasal cavity transfers the composition from the body to the epithelium. The body may also be constructed of, or have a portion comprising, an absorbent material 104. The distal end 103 of the body 100 is preferably smooth or rounded, and may optionally have a smooth or rounded member 106 attached thereto.

Alternatively, at least the distal end of the elongate body may have a layer of a pharmaceutical composition situated between the body and a retractable or degradable sheath which covers it. The sheath may, for example, be retracted by sliding the sheath proximally along the exterior of the elongate body, or by drawing the sheath into or through a lumen extending within the elongate body. Retraction or degradation of the sheath exposes the pharmaceutical composition, which may then be applied directly to a selected portion of the nasal epithelium, such as a portion overlying the SPG or a portion that includes or overlies one or more branches of the olfactory nerve or another InNS or an InBV. The degradable sheath may, for example, be made of a material which degrades shortly following contact with moisture. Thus, by inserting a body having an applicator portion covered with such a degradable sheath into the apex of the nasal cavity of a patient, degradation of the sheath is effected and causes the composition on the applicator portion to be exposed, whereupon it may be applied to a portion of the nasal epithelium.

The invention further includes a systemic drug delivery device which has the same construction as the intranasal delivery device of the invention, except that the device has an applicator portion, which may, for example, be a portion on which the drug is present, a portion to which the drug may be supplied, or a lumen through which the drug may be supplied. This applicator portion is preferably adapted for location in close anatomic proximity to a highly vascularized portion of the nasal epithelium when the distal portion of the body of the device is in the apex of the nasal cavity. Such a device may, for example, have an absorbent portion in which the drug is absorbed and which contacts one or more of the nasal conchae when the device is placed in the nasal cavity. Alternatively, the device may have a lumen which communicates with an outlet port which is situated on the device such that the port is opposite a desired anatomic site (e.g., a nasal concha or the nasal orifice of a sinus) when the device is placed in the nasal cavity.

Figure 5:
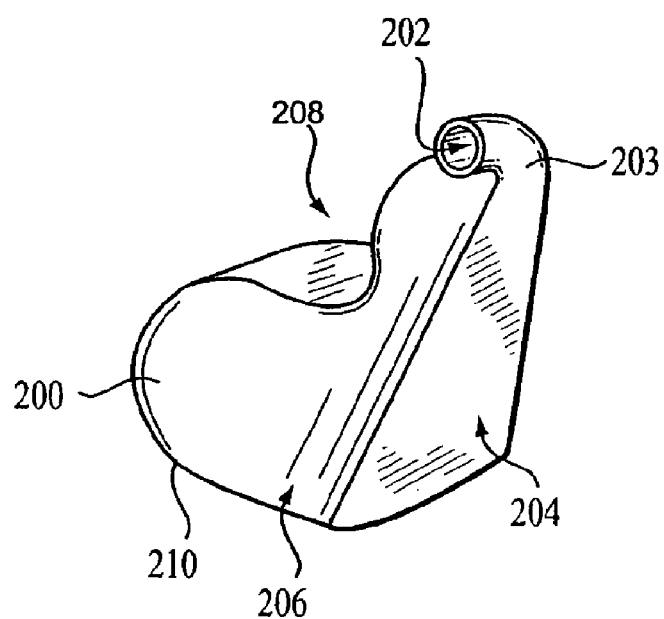
FIG. 5 is a diagram of an anatomically adapted dorsonasal delivery nozzle of the invention. The nozzle depicted in this Figure is adapted for the left nostril of a human patient.
Figure 6:
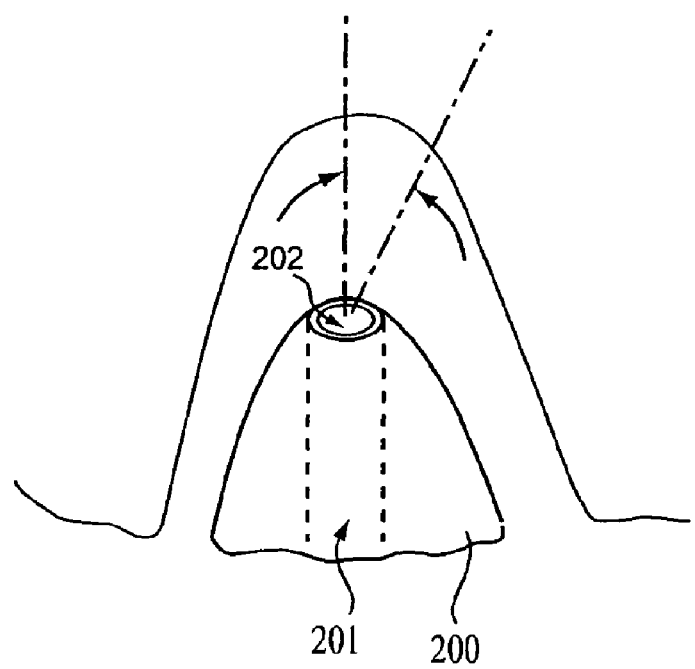
FIG. 6 is a diagram of the orientation between the outlet port of the anatomically adapted dorsonasal delivery nozzle of the invention as shown in FIG. 5 and the apex of the nasal cavity of a human. The angle phi is indicated.

The invention also includes an anatomically adapted intranasal delivery nozzle 200 which may be used as an applicator for providing a gel, foam, vaporized, aerosolized, or atomized liquid, or a dispersed powder or micropowder to or near the apex of the nasal cavity, while preferably minimizing delivery of the composition to other portions of the nasal cavity. One embodiment of such a nozzle is illustrated in FIGS. 5 and 6. The nozzle has a body having one or more delivery lumens 201, each of which extends through the nozzle from the proximal end 210 thereof to one or more outlet ports 202 located on the distal portion 203 thereof. The nozzle has an exterior portion which is shaped as follows. The exterior portion has a flattened portion 204 situated between the proximal end 210 and the distal portion 203 thereof for seating against the nasal septum. The exterior portion also has an anterior portion 206 situated between the proximal end 210 and the distal portion 203 thereof for seating against at least one portion of the nasal cartilage. The exterior portion also has a posterior portion having one or more indentations 208 situated between the proximal end 210 and the distal portion 203 thereof for seating against one or more of the nasal conchae. Each indention has a generally curved shape which conforms to the shape of the corresponding nasal concha. For example, the exterior portion may have a distal and a proximal indentation, the distal indentation being located nearer the distal end of the nozzle, wherein the distal indentation is adapted to the shape of the middle concha for seating the nozzle against the middle concha, and wherein the proximal indentation is adapted to the shape of the inferior concha for seating the nozzle against the inferior concha.

The delivery lumen 201 of the anatomically adapted intranasal delivery nozzle extends from the proximal end 210 of the nozzle to a discharge port 202 at the distal end 203 thereof. When the nozzle is seated in the nasal cavity of a human, the discharge port is situated such that the axis extending (generally perpendicularly) through the discharge port passes through the apex of the nasal cavity, or is offset from the apex of the nasal cavity by an angle, phi, as indicated in FIG. 6, such that phi is from 0 to about 30 degrees, and preferably such that phi is from 0 to about 15 degrees. The discharge port may be generally circular, or it may be shaped (e.g., oval, or circular having opposed raised portions on the circumference thereof) in order to more specifically direct the composition discharged therethrough at a selected portion of the nasal epithelium (e.g., a portion situated in the sphenoethmoidal recess). The proximal end of the anatomically adapted dorsonasal delivery nozzle may be connected with one or more reservoirs, generators, or other sources of the agent, or a combination of agents, to be delivered therethrough. A single source of agent may be directed through a plurality of delivery lumens which connect the source with one or a plurality of discharge ports. Alternatively, independent sources of different agents may be directed through a plurality of delivery lumens which connect the sources with one or a plurality of discharge ports.

The anatomically adapted intranasal delivery nozzle may be constructed of a rigid, flexible, deformable, or elastomeric material. In one embodiment, the nozzle is constructed of a material which is, either initially or under certain conditions (e.g., above a certain temperature), deformable. Such a material may, for example, be a wax or a plastic which becomes pliable when heated to a temperature above normal body temperature (i.e., >about 98° F.), but below a temperature which will cause injury to human nasal epithelium upon contact therewith for several minutes (i.e., <about 108° F.). Other exemplary materials are plastic composition which either remains plastic (e.g., a closed cell foam) or are which hardens with time (e.g., a polymerizing plastic). According to this latter embodiment, the nozzle is inserted into a nostril of the patient who will thereafter use the nozzle, in order to conform the nozzle to the interior geometry of that patient's nasal cavity. This procedure is preferably performed by a medical practitioner, or by a person having knowledge of the anatomy of the human nasal cavity, so that the nozzle is seated in the patient's nostril such that the discharge outlet is directed toward the apex of the patient's nasal cavity (i.e., the angle phi in FIG. 6 is from 0 to about 30 degrees). Alternatively, a deformable material may be inserted into a patient's nasal cavity in order to record the shape thereof, and this deformed material may subsequently be used to fashion a mold for duplicating that shape.

The anatomically adapted dorsonasal delivery nozzle may optionally further comprise one or more distal seating portion which, upon insertion of the nozzle into the nostril of the patient, contact the superior surface of the nasal cavity, thereby preventing over-insertion of the nozzle. The discharge port(s) may be inferiorly spaced with respect to the distal seating portion when it is seated within the nasal cavity of the patient, so that the path between the discharge port and the apex of the nasal cavity is not blocked by the conchae.

The anatomically adapted intranasal delivery nozzle is used to deliver a composition intranasal by seating the nozzle in a nostril of a patient, such that the flattened portion is seated against the nasal septum, the indentation, if any, is seated against a concha, and the anterior portion is seated against the nasal cartilage. Optionally, or in place of one of these other seatings, the distal seating portion is seated against the superior surface of the nasal cavity. When the nozzle is thus seated, a gel, foam, mousse, liquid, dispersed power, aerosol, etc. comprising the composition is provided to the delivery lumen, thence to the discharge port, and thence into the nasal cavity of the patient (e.g., to a dorsonasal or superior portion of the nasal epithelium). In the apex, the composition can contact a dorsonasally located portion of the nasal epithelium and thereby deliver the composition to that portion. It is noted that certain anatomically adapted intranasal delivery nozzles may be adapted for only one nostril of the patient; when this is so, a second nozzle adapted for the other nostril of the same patient should be provided. Alternatively, the outlet port of the nozzle may be changeable (i.e., rotatable or deflectable), such that the same adapter portion, with the outlet port facing in the opposite direction, may be used in the patient's other nostril.

The anatomically adapted delivery nozzle of the invention may be adapted, by placing the outlet port thereof at an alternative location on the body of the nozzle, to deliver a composition specifically to a different portion of the nasal cavity, such as to the nasal cavity orifice of one or more sinuses. The composition thus delivered may, for example, be a pharmaceutical composition comprising one or both of a steroid and a vasoconstrictor. By specifically delivering such a composition to the anatomical site at which it exerts its biological activity, the amount of drug which is administered may be minimized and side effects normally associated with administration of the composition (e.g., nasal epithelial hypertrophy associated with intranasal administration of vasoconstrictors) may be minimized.

Figure 7C:
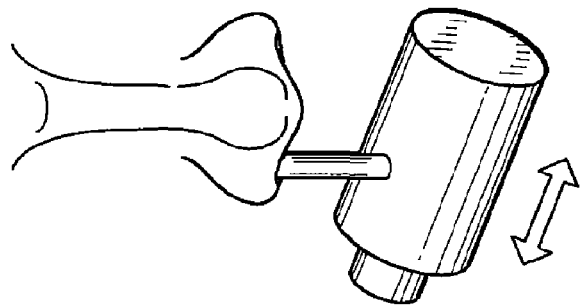
FIGS. 7A, 7B, and 7C, is a trio of diagrams depicting manually pressure-actuated drug delivery devices having intranostril applicators. A prior art device is depicted in FIG. 7A, in which actuating pressure is applied approximately coaxially with the nostril. In the devices of the invention, as depicted in FIGS. 7B and 7C, actuating pressure is not applied coaxially with the nostril.
Figure 7B:
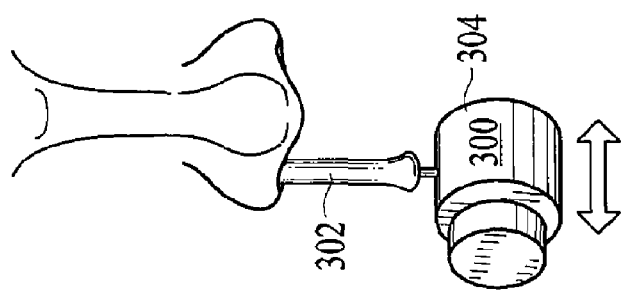
Figure 7A:
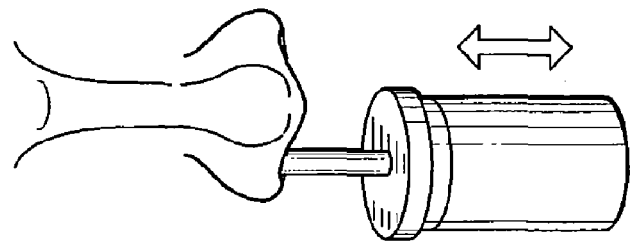

The invention also includes an intranasal drug delivery device or applicator which overcomes a particular shortcoming of prior art intranasal drug delivery devices. As illustrated in FIG. 7A, prior art intranasal drug delivery devices are actuated by applying pressure to all or a portion of the applicator in a direction that is substantially co-linear (i.e., not more than about 15 degrees offset from co-linear) from the axis of the nostril. Use of such devices carries the risk that the device may be unintentionally urged, along the axis of the nostril, with excessive force, leading to discomfort or injury of the patient.

The improved intranasal drug delivery device 300 of the invention overcomes this limitation by changing the direction in which pressure is applied to the device by the patient. As illustrated in FIGS. 7B and 7C, the improved intranasal delivery device comprises an intranostril applicator 302 having a lumen extending therethrough. The lumen of the intranostril applicator is in fluid communication with a discharge port on an end of the intranostril applicator, which is insertable within a nostril of a human patient. This lumen is also in actuatable fluid communication with a drug within a container 304. Fluid communication between the lumen and the interior of the container is actuated by application of force by the patient to an actuator interposed between the lumen and the interior of the container. When the patient applies force to the actuator, the drug is provided to the lumen of the intranostril applicator, thence through the discharge port and into the nasal cavity of the patient.

The intranostril applicator may be substantially any body which may be inserted fully or partially into the nostril of a human and which has a lumen extending therethrough. The drug container may be substantially any container which is pressure-activated, such as a pressurized drug container connected to the lumen of the intranostril applicator by a manual pressure-actuated valve, a pressure-activated pump, a syringe, a metered dose applicator, and the like. Preferably, the intranostril applicator and at least a portion of the drug container are of a unitary construction. Alternatively, the intranostril applicator and the drug container may be detachable, whereby the intranostril applicator may be inserted into a nostril of a patient prior to attaching the drug container thereto.

An important feature of the improved intranasal drug delivery device of the invention is that the pressure which is applied by the patient in order to actuate the same is applied at an angle offset from (i.e., at least about 15 degrees offset from, and preferably about 30, about 45, about 60, or about 90 degrees offset from) the axis of the nostril in which the intranostril applicator is placed. The discomfort and the risk of injury to the patient due to inappropriate drug source actuation pressure is thereby reduced significantly, and the device is also made easier to use. Any inappropriate pressure is likely to cause the intranostril applicator to twist within or become disengaged from the nostril, rather than cause the intranostril applicator to be driven along the axis of the nostril into a tissue, which would injure the patient.

The invention also includes a dorsonasally implanted electronic neural stimulator, such as a transepithelial neural stimulation (TENS) device. This device is implanted anatomically close to, preferably in contact with, a dorsonasal nerve structure such as the SPG. The device may, for example, be implanted on or in the dorsonasal epithelium, such as a portion of the nasal epithelium overlying a dorsonasal nerve structure. The device may be mono- or bi-polar. The device may have an internal power supply, or power may be supplied to the device using an external device (e.g., an inductively coupled power supply). Nerve block of a dorsonasal nerve structure may thus be effected by energizing the device, meaning that electrical potential is provided to the device, such as from an internal power supply, external power supply leads, or from an extra-corporeal inductively coupled power supply.

The Kit of the Invention

The invention additionally includes a kit comprising a long-acting local anesthetic pharmaceutical composition, as described herein, and an applicator, as also described herein, for intranasally, and preferably dorsonasally, administering the composition to a human patient to inhibit a CNvD. The kit is used by administering the composition to the patient at a time when the patient is experiencing a symptom of a CNvD episode or a prodromal symptom of a CNvD. The kit may further comprise a migraine therapeutic pharmaceutical agent, another pharmaceutically active agent, another local anesthetic, and the like. The kit may, and preferably does, further comprise instructional material which describes directed intranasal (e.g., dorsonasal) administration of the composition to a patient. The instructional material may, for example, comprise written instructions to intranasally or dorsonasally administer the composition included in the kit in accordance with this invention.

The kit described herein may also be used for inhibition of muscular headaches. The components of the kit for this purpose are substantially the same, with the exception that any instructional material should describe the usefulness of the compositions and methods of the invention for inhibiting a muscular headache, rather than, or in addition to, a CNvD. If the kit may also be used to inhibit a muscular headache, in which instance the local anesthetic pharmaceutical composition need not be long-acting and is administered to the patient during a muscular headache episode.

Co-Administration of a Local Anesthetic and Another Compound to Effect Systemic Delivery of the Compound The invention further relates to the discovery that non-intravenous administration of a composition comprising a local anesthetic and a pharmaceutically active agent to an animal such as a mammal, particularly a human, improves systemic uptake of the agent in the animal, relative to the uptake achieved by non-intravenous administration of the agent alone to the animal by the same route.

The present invention includes a method of systemic drug delivery, the method comprising non-intravenously administering to a human patient a composition comprising a local anesthetic and a pharmaceutically active agent, whereby systemic delivery of the agent is improved relative to systemic delivery of the agent when delivered by the same non-intravenous route in the absence of the local anesthetic. The pharmaceutically active agent may be any drug. It is contemplated that this method of effecting systemic delivery is particularly useful for delivery of any agent which is able to diffuse through vascular and other tissues to a greater degree in the presence of the local anesthetic than in the absence of the local anesthetic. Thus, the agent may be, for example, a hormone, a peptide, a liposome, or a polymeric molecule such as heparin.

Any pharmaceutically active agent which is desired to be delivered systemically may be co-administered non-intravenously in a composition comprising the agent and a local anesthetic. Where the local anesthetic is not being administered for the purpose of inhibiting a CNvD, delivery of a composition comprising a local anesthetic and the agent intended for systemic delivery need not be directed to the dorsonasal region of the nasal cavity. Because the nasal cavity is highly vascularized, delivery of the composition may be directed to substantially any portion of the nasal epithelium to achieve systemic delivery of the agent. Furthermore, the composition may be delivered to any vascularized tissue, such as to the surface of a mucosal epithelium or to a skin surface, for example, to achieve systemic delivery of the agent.

The local anesthetic may be any local anesthetic except cocaine, which is a vasoconstrictor. The local anesthetic compounds, formulations, dosages, and methods of administration which are useful for this method of the invention are substantially the same as those described herein with respect to inhibiting a neurovascular headache, a muscular headache, or a CNvD. Compounds, formulations, and dosages of the other pharmaceutically active agents described in this method are known in the art. Owing, in part, to the vasodilatory activity of local anesthetics, these compounds may be used according to this method at doses of about half their art-recognized doses to their full art-recognized doses.

Theory Proposed to Explain the Mechanism of Improved Systemic Delivery of a Pharmaceutically Active Agent by Co-Administration with a Local Anesthetic Without wishing to be bound by any particular theory, it is believed that administration of a local anesthetic to a vascularized tissue induces dilation of blood vessels within the tissue. Vasodilation results in recruitment of surface blood vessels and increases the ability of a compound present in the tissue to pass into the systemic circulation. Similarly, carrier preparations (e.g., DMSO, proteins, peptides, and/or charged compounds) can facilitate delivery of the composition to an InNS or InBV to effect systemic or CNS delivery of the composition. Therefore, co-administration to a tissue of a local anesthetic and a pharmaceutically active agent improves the ability of the agent to pass from the tissue to the bloodstream for systemic delivery.

Dosing Information Relevant to Systemic Drug Delivery

The local anesthetic doses and formulations which are useful for co-administration of the local anesthetic and another compound to effect systemic delivery of the compound are substantially the same as those described for the method of inhibiting a CNvD. In view of the present disclosure, it will be understood by the artisan of ordinary skill that the dose and formulation of the local anesthetic will depend upon, among other factors, the age, size, condition, and state of health of the animal, the anatomical location to which the composition will be delivered, the identity of the local anesthetic, and the identity of the compound to be co-administered. Substantially any amount of local anesthetic may be used. By way of example, compositions which comprise the compound to be co-administered and the local anesthetic at a concentration of about 0.01% to about 53% by weight, and preferably about 0.25% to about 10% by weight, more preferably about 0.5% to about 5% by weight, and most preferably about 2.5% by weight, may be used. The composition may be prepared as a liquid, a semi-solid, or a solid, as described herein. The composition may be formulated for intranasal, topical, subcutaneous, buccal, or substantially any other non-intravenous route of administration using methods and compositions well known in the art. The dose of the compound to be co-administered is dependent upon the identity of the compound, the purpose for which the compound is to be administered, and the size, age, condition, and state of health of the animal. Compounds, formulations, and dosages of pharmaceutically active agents described in this method are known in the art. Owing, in part, to the vasodilatory activity of local anesthetics, these compounds may be used according to this method at doses of about half their art-recognized doses to their full art-recognized doses.

While the invention has been described with reference to human anatomy, it is contemplated that the compositions and methods of the invention can be used analogously in any animal, particularly in any mammal, especially regarding co-administration of a local anesthetic and any pharmaceutically active agent to effect or enhance systemic delivery of the agent.

Directed Intranasal Administration of a Pharmaceutical Composition

Intranasal administration of a pharmaceutical composition directed to only a portion of the nasal epithelium of a patient can avoid drawbacks of previous non-directed intranasal delivery methods. For example, administration can be directed specifically to a portion of the nasal epithelium that overlies (or is in close proximity to) an InNS or an InBV. For compositions (e.g., local anesthetics and compounds co-administered with a local anesthetic) that are capable of diffusing through epithelial tissue, directing administration to a portion of the epithelium located in close anatomical proximity to the InNS or InBV can result in delivery of the composition to the selected InNS or InBV.

When delivery of a composition to the olfactory nerve (or thence to the olfactory bulb or the brain) is desired, the composition should be administered to the superior surface of the nasal cavity, where the branches of the olfactory nerve that penetrate the cribiform plate of the ethmoid bone and emerge at or near the surface of the nasal epithelium. At least some extensions of the olfactory nerve emerge from the ethmoid into the superior nasal concha and the upper portion of the nasal septum. The dorsonasal portion of the nasal epithelium can also include branches of the olfactory nerve, although innervation varies among individuals. Directed intranasal delivery of a composition to a nerve structure such as the olfactory nerve demonstrates that intranasal administration of a composition, if directed to an appropriate intranasal tissue or structure, can result in uptake of an active agent by a nerve structure that is separated from the nasal cavity by a bone (e.g., the olfactory nerve is separated from the nasal cavity by the cribiform plate of the ethmoid bone as well as the nasal epithelium).

Portions of at least the olfactory, nasal, ethmoidal, palatine, greater petrosal, and maxillary nerves are located in close anatomical proximity to portions of the nasal epithelium, and compositions having a sufficiently high ability to diffuse through nasal epithelium tissue can be delivered to these nerves by way of intranasal administration to the corresponding portion of the nasal epithelium.

The identity of the active agent in the composition administered to an InNS or an InBV is not critical, so long as the composition is administered to a portion of the nasal epithelium overlying or in sufficiently close proximity to the InNS or InBV and in a carrier or with a compound (e.g., a local anesthetic, lipid carrier, or other tissue-penetrance-modulating preparation) that facilitates diffusion or other transport of the agent to the InNS or InBV. Non-limiting examples of useful agents include natural or altered or carrier viruses, prions, other infectious or therapeutic cellular or subcellular agents or microorganisms, stem cells, or other cellular therapeutic agents, DNA, RNA, oligonucleotides, polypeptides, amino acids, fatty acids, lipids, carbohydrates, vitamins, supplements, minerals, nutrients, oxygenated substrates, microspheres, antibiotics, antiviral agents, antifungal agents, memory enhancing agents, neurotransmitters, antiepileptics, antiseizure agents, analgesics, ions including magnesium, anti-neuropathic pain agents, anti-central pain agents, antidepressant agents, cox inhibitors (including cox2 inhibitors), LOX inhibitors, membrane stabilizing agents, growth factors, hormones (e.g., anabolic and catabolic steroids), ATP, ADP, NAD(P), NAD(P)H, energy substrates, propylene glycol, carrier molecules, DMSO, cytokines, anti-cytokines, TNF, anti-inflammatory agents, melatonin, chemotherapy agents, and radiolabeled compounds.

In one embodiment, intranasal delivery of a composition containing an active agent is performed as described herein. The composition is administered to a portion of the nasal epithelium that overlies an InNS. The composition is administered in a sufficiently high amount that the agent is not only taken up by the InNS, but is also delivered to another nerve structure with which the InNS communicates. In one example, a composition is administered to a superior portion of the nasal cavity in order to effect delivery of an agent to the olfactory nerve. By way of the olfactory nerve, the agent travels (e.g., diffuses or is actively transported) to the olfactory bulb of the brain (i.e., with which the olfactory nerve connects) and thence to the brain. In another example, a composition comprising an agent is dorsonasally administered so that the agent is taken up by a DnNS (e.g., the SPG) and transported to another nerve structure with which the DnNS is connected (e.g., the SPG is connected to the trigeminal nerve and, by way thereof, to the brain). In this way, cephalic, spinal cord, or other neural delivery of the agent can be effected. Similar methods can be used to direct administration of the composition to other portions of the nasal cavity so as to effect delivery to selected InNSs, selected InBVs, and tissues in which the two are intimately related.

The dose of agent that should be used in the intranasal delivery methods described herein depends on the identity of the agent and the identity of the targeted tissue. When compositions are directed to a portion of the nasal cavity including or overlying an InNS in order to effect delivery of the composition (or a component of the composition) to the central nervous system (CNS), the dose of the agent in the composition can often be significantly lower than the dose that would be necessary to administer by an oral or intravenous route. When systemic delivery of an agent is desired, directed delivery of a composition comprising a high concentration of the agent can be used, so as to enhance the rate and amount of agent taken up into the bloodstream. Thus, agents delivered by directed intranasal administration can be administered in concentrations and amounts ranging from at least several times the amount administered orally or intravenously to amounts as small as 1% to 10% the amount administered orally or intravenously, depending on the agent. A skilled artisan is able to titrate amounts appropriately, for example administering a small amount at first and gradually increasing the dosage until a desired pharmacological effect is achieved.

The invention is now described with reference to the following Examples. These Examples are provided for the purpose of illustration only and the invention should in no way be construed as being limited to these Examples, but rather, should be construed to encompass any and all variations which become evident as a result of the teaching provided herein.

EXAMPLE 1

Dorsonasal Administration of Ropivacaine for Inhibition of Acute Migraine Episodes The purpose of the experiments described in this Example was to determine the efficacy of dorsonasal administration of ropivacaine for inhibition of acute migraine episodes. Ropivacaine was dorsonasally administered to individual patients experiencing head pain, other symptoms, or both, believed to be associated with an acute migraine episode. Patients assessed head pain prior to and after ropivacaine administration.

Dorsonasally administered ropivacaine rapidly inhibited of migraine in 92% of the ambulatory patients, as evidenced by an average 90% reduction in perceived pain within one hour, usually within 15 minutes or less. Symptoms of nausea and photophobia associated with acute migraine episodes in patients were similarly inhibited. Rebound of migraine occurred in only 5.4% of patients within twenty-four hours of treatment. These results demonstrate that dorsonasal administration of ropivacaine is an efficacious method of inhibiting an acute migraine episode.

The materials and methods used in the procedures performed in this Example are now described.
Ropivacaine Composition Ropivacaine-HCl (NAROPINT™, Astra USA, Westborough, Mass.) was used as the commercially-available 0.75% (w/v) solution, and was obtained in 30 milliliter, sterile injectable vials.
Methods of Ropivacaine Administration Three methods were used to achieve dorsonasal delivery of ropivacaine to individual patients. Ropivacaine was administered to a first group of patients by an intranasal drip method. Ropivacaine was administered to a second group using cotton swabs, the absorbent portions of which were saturated with the ropivacaine solution. Ropivacaine was administered to patients in a third group by spraying the ropivacaine solution into each nostril, using either a squeeze-type spray bottle or a metered-dose spray bottle.

The intranasal drip method used to administer ropivacaine to the first group of patients was a based on the method described by Barre (1982, Headache 22:69-73), except that the ropivacaine solution was used in place of the solution used by Bane. Approximately 0.75 milliliter to approximately 1.0 milliliter of the ropivacaine solution was administered by way of each of the nostrils of each patient.

The cotton swab method used to administer ropivacaine to the second group of patients comprised gently inserting cotton swabs, sequentially and bilaterally, into the nostrils of patients and urging the swabs dorsally until their absorbent portions contacted portions of nasal epithelium located dorsal to the middle conchae. Each swab was left in place for approximately one minute, and was then withdrawn. Approximately 0.5 milliliter of the ropivacaine solution was delivered to each nostril using this method.

Patients in a third group were administered ropivacaine by spraying less than about 0.5 milliliter of the ropivacaine solution into each of the patient's nostrils using either a sterile squeeze bottle or a sterile metered-dose spray bottle of known design. The design and operation of each of these spray bottles are well known in the art.

Prior to administration of ropivacaine, each patient was placed in a supine position with the patient's head hyperextended approximately 45 degrees and rotated approximately 30 degrees to the right side. In this position, an imaginary line extending from the region of the nasal epithelium overlying the SPG of the patient through the patient's left nostril was approximately vertical. Ropivacaine was then administered to the left nostril of the patient as described for each of the three groups of patients. Ropivacaine was administered to each patient's right nostril after rotating the patient's head approximately 30 degrees to the left. Ropivacaine was administered to both nostrils of each patient to prevent cases of unilateral migraine from developing into contralateral migraine.
Assessing Ropivacaine-Induced Pain Relief Prior to ropivacaine administration, each patient rated perceived headache pain according to a standard pain scale of the type used in the art. Patients were asked to rank the severity of pain which they were experiencing on a scale from 0 (no pain) to 10 (worst pain imaginable). This ten-point pain rating scale is analogous to, but has more gradations than, the four-point rating system used by the International Headache Society (IHS; Headache Classification Committee of the International Headache Society, 1988, Cephalalgia 8 (Suppl. 7):19-28). Ropivacaine was administered to one nostril of each patient, and then to the other. The time required to administer ropivacaine to both nostrils of each patient was approximately three minutes. Five minutes after the completion of administration of ropivacaine to the patient's first nostril, each patient again rated perceived headache pain. If no pain relief was evident, dosing was repeated, and the rating procedure was repeated. Pain ratings were obtained for each patient until peak effect appeared to be achieved, for up to ninety minutes, acutely. Follow-up of each patient's condition was attempted by direct contact or by telephone contact between six and eight hours post-treatment, between twenty-four and forty-eight hours post-treatment, and up to one week post-treatment.

The results obtained from the procedures performed in this Example are now described.

The population of patients treated in the procedures performed in this Example comprised forty-two adults, each of whom sought migraine relief. The results of treatment of each of these patients with either ropivacaine or (for three patients) lidocaine are presented in Table 1. The five patients who were either treated with lidocaine or did not clearly meet the IHS criteria for migraine were not included in the analysis presented herein of the efficacy of dorsonasal ropivacaine treatment of migraine. The demographic and pretreatment characteristics of the patients who met IHS migraine criteria and who were treated with ropivacaine are presented in Table 2.

TABLE 1

Summary of Patient Data.

| Patient Identifier | Medical History[1] | Headache History[2] | Associated Symptoms[3] | Treatment[4] | Results[5] |
|---|---|---|---|---|---|
| P#1 | | Posterior Migraine | Mild Nausea Photophobia | R 0.75% 2 Sprays | Initial pain: 8 Pain 10 min post-treatment: 0 No rebound up to 24 hours |
| P#2 | Head Trauma Resulting From Auto Accident | Constant Headache for circa 28 years | | R 0.75% 2 cc Drops | No Relief[6] |
| P#3 | Meningitis circa 26 years pre-treatment | Monthly Headaches of circa 3 day duration | | R 0.75% 2 cc Drops | Transient Improvement[6] |
| P#4 | Post Partum Headaches | Migraine | | R 0.75% 2 cc Drops | Initial pain: 9 Pain 3 min post-treatment: 0 No rebound up to 24 hours |
| P#5 | | Posterior and Lateral Migraine | Nausea Photophobia | R 0.75% 2 cc Drops | Initial pain: 9 Pain 15 min post-treatment: 0 No rebound up to 24 hours |
| P#6 | Post Partum Headache | Temporal and Frontal Headache | | R 0.75% Sat'd Cotton Swab | Initial pain: 8 Pain 5 min post-treatment: 0 No rebound up to 24 hours |
| P#7 | | Temporal and Frontal Headache of 2-3 Day Duration | Visual Changes | R 0.75% Sat'd Cotton Swab | Initial pain: 10 Pain 2 min post-treatment: 0 No rebound up to 24 hours or up to 48 hours |
| P#8 | | Patient's First Vascular Headache Episode (CT scan ruled out subarachnoid hemorrhage) | Loss of Vision Bed-ridden | R 0.75% Sat'd Cotton Swab | Initial pain: 10 Pain 10 min post-treatment: 0 Pain 24 hours post-treatment: 1 (this pain was relieved by administering a 325 milligram Tylenol ™ (McNeil-PPC, Inc., Fort Washington, PA) tablet) No rebound up to two weeks |
| P#9 | | Migraine | | R 0.75% Sat'd Cotton Swab | Initial pain: 8.5 Pain 5 min post-treatment: 1 No rebound up to 3 days |
| P#10 | | Migraine | Nausea Photophobia | R 0.75% Sat'd Cotton Swab | Initial pain: 9 Pain 3 min post-treatment: 0 No rebound up to one week |
| P#11 | | Occipital Headache few times per year | Must lie down | R 0.75% 2 cc Drops | Initial pain: 9 Pain 15 min post-treatment: 5 Pain 60 min post-treatment: 0 No rebound up to one week |
| P#12 | | Migraine | | L 2.0% 1 cc Drops | Initial pain: 7 Pain 5 min post-treatment: 2 Pain 45 min post-treatment: 6[B] |
| P#13 | Marfan's Syndrome | Migraine | Mild Nausea | R 0.75% 2 Sprays | Initial pain: 6 Pain 30 min post-treatment: 0[6] No rebound up to 24 hours |
| P#14 | | Migraine (Worst during menses) | Nausea Photophobia Visual changes | R 0.75% Sat'd Cotton Swab | Initial pain: 8 Pain 3 min post-treatment: 0 Pain 5 min post-treatment: 2 Pain 18 hrs post-treatment: 8 (After 18 hrs, treated w/spray) |
| | | | | Retreated with 2 Sprays | Pain following spray: 0[6] No rebound up to 48 hours |
| P#15 | Viral Gastro-intestinal Disturbance | Sinus Headache | Vertigo developed after sneeze | L 2.0% 1 cc Drops | Initial pain: 6 Pain 15 min post-treatment: 0 Pain 30 min post-treatment: 6 |
| P#16 | Post Partum Headache | Post Dural Puncture Headache | | L 2.0% 1 cc Drops | Initial pain: 8 Pain 15 min post-treatment: 4[6] |
| P#17 | | Migraine | Nausea Photophobia | R 0.75% 2 Sprays | Initial pain: 8 Pain 15 min post-treatment: 2 Pain 20 min post-treatment: 0[6] No rebound up to 48 hours |
| P#18 | | Migraine | Visual changes | R 0.75% Sat'd Cotton Swab | Initial pain: 9 Pain 3 min post-treatment: 0 |
| P#19 | Lumbar Disc Surgery | Migraine | | R 0.75% Sat'd Cotton Swab | Initial pain: 9 Pain 1 min post-treatment: 0 No rebound up to 48 hours |

TABLE 1-continued

Summary of Patient Data.

| Patient Identifier | Medical History[1] | Headache History[2] | Associated Symptoms[3] | Treatment[4] | Results[5] |
|---|---|---|---|---|---|
| P#20 | Congenital Megacolon | Migraine | Nausea Vomiting | R 0.75% Sat'd Cotton Swab | Initial pain: 8 Pain 3 min post-treatment: 0 No rebound up to one week |
| P#21 | | Migraine | Nausea | R 0.75% Sat'd Cotton Swab | Initial pain: 10 Pain 3 min post-treatment: 1 Pain 5 min post-treatment: 0 No rebound up to one week |
| P#22 | | Cervical and Occipital Headache | | R 0.75% Sat'd Cotton Swab | Initial pain: 8 Pain 10 min post-treatment: 0 No rebound up to 24 hours |
| P#23 | Cervical Spine Pain | Cervical and Occipital Headache | Nausea | R 0.75% Sat'd Cotton Swab | Initial pain: 9 Pain 5 min post-treatment: 1 No rebound up to 24 hours |
| P#24 | | Migraine | | R 0.75% Sat'd Cotton Swab | Initial pain: 9 Pain 3 min post-treatment: 0 |
| P#25 | | Recurrent Parietal and Occipital Headaches, Bilateral Temporal Headaches | Nausea Visual changes | R 0.75% Sat'd Cotton Swab | Initial pain: 10 Pain 3 min post-treatment: 0 No rebound up to one week |
| P#26 | | Migraine | Nausea Photophobia | R 0.75% Sat'd Cotton Swab | Initial pain: 10 Pain 5 min post-treatment: 0 No rebound up to 24 hours |
| P#27 | | Recurrent Frontal, Parietal, Temporal, and Occipital Headaches | Nausea Photophobia | R 0.75% Sat'd Cotton Swab | Initial pain: 10 Pain 8 min post-treatment: 0 No rebound up to 48 hours |
| P#28 | | Migraine | Nausea Visual changes | R 0.75% Sat'd Cotton Swab | Initial pain: 9 Pain 5 min post-treatment: 0 No rebound up to 48 hours |
| P#29 | | Migraine | Nausea Photophobia | R 0.75% Sat'd Cotton Swab | Initial pain: 10 Pain 5 min post-treatment: 0 No rebound up to 24 hours |
| P#30 | Temporal Arteritis, Steroid Use | Migraine | Nausea | R 0.75% Sat'd Cotton Swab | Initial pain: 9 Pain 10 min post-treatment: 1 No rebound up to 18 hours |
| P#31 | | Migraine | | R 0.75% Sat'd Cotton Swab | Initial pain: 9 Pain 2 min post-treatment: 1 No rebound up to 24 hours |
| P#32 | Chemotherapy | Migraine | Nausea | R 0.75% Sat'd Cotton Swab | Initial pain: 10 Pain 15 min post-treatment: 0 |
| P#33 | Hypertension, Controlled Diet | Migraine | Nausea, Photophobia, Visual changes | R 0.75% 2 Metered Sprays | Initial pain: 9 Pain 5 min post-treatment: 5 Pain 30 min post-treatment: 3 Pain 90 min post-treatment: 0 (Patient presented one week later) |
| | | Migraine | | 2 Metered Sprays | Initial pain: 10 Pain 15 min post-treatment: 5 Pain 30 min post-treatment: 4 Pain 90 min post-treatment: 0 No rebound up to one week |
| P#34 | Major Depression, Chronic Hepatitis C | Migraine | Nausea, Photophobia | R 0.75% 2 Metered Sprays | Initial pain: 7 Pain 20 min post-treatment: 3 (Then repeated treatment using two metered sprays) |
| | | | | 2 Metered Sprays | Pain 5 min post-treatment: 0 (Patient presented seven hours later) |
| | | | | 2 Metered Sprays | Initial pain: 2 Pain 10 min post-treatment: 0 No rebound up to 24 hours |
| P#35 | Head Trauma | Migraine | Nausea, Visual changes | R 0.75% 2 Metered Sprays | Initial pain: 8 Pain 30 min post-treatment: 6 Pain 60 min post-treatment: 2 |
| P#36 | Complaints of "Stuffy Nose" | Migraine | Nausea, Photophobia, Visual changes | R 0.75% 2 Metered Sprays | Initial pain: 9 Pain 5 min post-treatment: 7 Pain 30 min post-treatment: 5 |

TABLE 1-continued

Summary of Patient Data.

| Patient Identifier | Medical History[1] | Headache History[2] | Associated Symptoms[3] | Treatment[4] | Results[5] |
|---|---|---|---|---|---|
| P#37 | | Atypical Right Side Headache Behind Eye | Nausea, Photophobia, Intense Eye Pain & Pressure | R 0.75% 2 Metered Sprays | Initial pain: 7 Pain 30 min post-treatment: 3 Pain 45 min post-treatment: 0 (Patient presented three days later) |
| | | | | 2 Metered Sprays | Initial pain: 2 Pain 10 min post-treatment: 0 No rebound up to 48 hours |
| P#38 | Head Trauma | Migraine | | R 0.75% 2 Metered Sprays | Initial pain: 3 Pain 30 min post-treatment: 0 |
| P#39 | | Migraine | Nausea | R 0.75% 2 Sprays | Initial pain: 9 Pain 2 min post-treatment: 0 No rebound up to 48 hours |
| P#40 | | Migraine | Mild Nausea | R 0.75% Sat'd Cotton Swab | Initial pain: 10 Patient exhibited apparent allergic reaction between 5 and 15 minutes post-treatment Pain 20 min post-treatment: 3 Pain 30 min post-treatment: 5 Level 5 pain endured 8 hours |
| P#41 | Head Trauma | Recurrent Headaches | Nausea, Photophobia, Perceived 'Whistling Sounds' | R 0.75% Sat'd Cotton Swab | Initial pain: 8 Pain 20 min post-treatment: 0 No rebound up to 48 hours |
| P#42 | | Migraine | Perceived 'Flashing Lights' | R 0.75% Sat'd Cotton Swab | Initial pain: 9 Pain 2 min post-treatment: 0 No rebound up to one week |

Notes:
[1] "Medical History" refers to events in the patient's medical history deemed potentially related to the patient's headache symptoms.
[2] "Headache History" describes the headache for which treatment was sought by the patient.
[3] "Associated Symptoms" describes symptoms described by the patient as accompanying the headache for which treatment was sought, past recurrent headache episodes, or both.
[4] "Treatment" indicates the compound which was administered to the patient: "R" refers to ropivacaine; "L" refers to lidocaine; # % refers to the concentration of the solution comprising the compound (expressed as % w/v); "2 Sprays" refers to delivery of less than about 0.5 milliliter of the indicated solution delivered by two sprays into each nostril of the patient using a sterile squeeze bottle containing the solution; "# cc Drops" refers to delivery of # milliliters of the indicated solution via the modified nasal drip method described herein; "Sat'd Cotton Swab" refers to delivery of the indicated solution using a standard cotton swab saturated with the indicated solution as described herein; "2 Metered Sprays" refers to delivery of less than about 0.5 milliliter of the indicated solution delivered by a combination of two sprays into each nostril of the patient using a sterile metered-dose spray bottle containing the solution.
[5] "Results" refers to pain relief experienced by each patient, using the pain rating method of the International Headache Society (i.e., 10 = worst pain imaginable; 0 = no pain). The term "min" means minutes.
[6] This patient experienced oropharyngeal numbness.

TABLE 2

Demographic and Pretreatment Characteristics of Patients.

| Characteristic | Value |
|---|---|
| Mean Age (Standard Error; Range) | 45.1 years (±2.1 years; 22-67) |
| Gender Male | 17 (45.9%) |
| Female | 20 (54.1%) |
| Duration of Current Headache, hours (Standard Error) | 23.2 (±4.1) |
| Mean Pain Level on 10-Point Scale (Standard Error; 95% conf. interval) | 8.64 (±0.223; 8.18-9.09) |
| Patients Experiencing Nausea | 23 (62.1%) |
| Patients Experiencing Photophobia | 14 (37.8%) |

Thirty-four of the thirty-seven (92%) migraine patients treated with ropivacaine experienced significant (i.e., certainly greater than 50%) reduction of migraine severity. Complete relief followed ropivacaine administration in 72% of the patients. Photophobia, nausea, and pain were simultaneously eliminated in migraine patients who experienced each of these symptoms. Rebound was evident in only two of the responding patients, meaning that the rebound rate was only 5.4%. Adverse effects of ropivacaine administration were minimal: one patient experienced an allergic response to ropivacaine administration, which response consisted of short-lived tachycardia, dizziness, and wheezing, all of which endured for about twenty minutes before subsiding. Even this patient who experienced an allergic response experienced a measurable reduction of migraine pain within twenty-five minutes post-treatment.

Pain Relief Effected by Cotton-Swab-Application of Ropivacaine

Among the twenty-four patients to whom ropivacaine was dorsonasally administered using a cotton swab, the mean pain severity rating prior to administration of ropivacaine was 9.06±0.16 points out of a possible 10 points (mean±standard error). The mean post-administration pain severity rating at the time of peak effect was 0.33±0.14 points out of a possible 10 points. Thus, dorsonasal administration of ropivacaine using a cotton swab resulted in a mean peak headache severity rating reduction of 8.73±0.249 points. The mean time that elapsed between the time of treatment and the perception by the patient of the peak effect was 7.41±1.47 minutes. Every patient in this group responded to treatment, 95% of the patients achieving a pain severity rating of zero or one, and 72% of patients achieving a pain severity rating of zero. One patient in this group experienced rebound of headache pain eighteen hours post-treatment. Thus, dorsonasal administration of ropivacaine using a cotton swab causes significant pain reduction in 100% of migraine patients, with rebound occurring in only 4% of patients.

Pain Relief Effected by Nasal-Drip-Application of Ropivacaine

Dorsonasal administration of ropivacaine effected by delivery of nasal drops resulted in a mean peak headache severity rating reduction of 9.00 points out of a possible 10 points in the three patients so treated. The mean time that elapsed between the time of treatment and the perception by the patient of the peak effect was 26.00±17.37 minutes. None of the three patients experienced migraine rebound.

Pain Relief Effected by Nasal-Spray-Application of Ropivacaine

Dorsonasal administration of ropivacaine effected by delivery using the nasal spray method resulted in a mean peak headache severity rating reduction of 6.22±0.66 points out of a possible 10 points in the ten patients so treated. The mean time that elapsed between the time of treatment and the perception by the patient of the peak effect was 33.9±8.48 minutes. Of the ten migraine patients treated by intranasal spray, all experienced significant reduction in headache pain severity. The majority of these patients experienced complete headache pain relief and did not experience rebound. The remainder experienced a mean headache pain severity rating reduction of 87.5±6.49%. One of the ten patients to whom ropivacaine was administered using a spray bottle experienced a separate episode of migraine one week later.

Comparison of Administration of Ropivacaine by Cotton Swab, by Nasal Drops, and by Nasal Spray The results obtained in patients who were administered ropivacaine by the three methods described herein are summarized in Tables 3 and 4.

TABLE 3

Effect of the Route of Ropivacaine Administration on Severity of Migraine Pain. Pain Ratings and Pain Relief are measured using a 10-point pain scale, as described herein.

| Method of Delivery | Pain Rating Prior to Administration | Pain Rating After Administration | Pain Relief |
|---|---|---|---|
| Cotton Swab | 9.06 | 0.33 | 8.73 |
| Nasal Drops | 9.00 | 0.00 | 9.00 |
| Nasal Spray | 7.22 | 1.00 | 6.22 |

TABLE 4

Effect of the Route of Ropivacaine Administration on Severity of Migraine Pain.

| Method of Delivery | Number of Patients | Mean Reduction in Pain Rating (IHS points) | Mean Time Until Maximal Effect | Rate of Pain Relief (IHS points per minute) |
|---|---|---|---|---|
| Cotton Swab | 24 | 8.64 | 7.41 | 2.32 |
| (Standard Error) | | (±0.25) | (±1.46) | |
| 95% confid. interval | | 8.12-9.16 | 4.37-10.4 | |
| Nasal Drops | 3 | 9.00 | 26.00 | 1.25 |
| (Standard Error) | | (0) | (±12.3) | |
| 95% confid. interval | | 5.89-10.6 | 0-100 | |
| Nasal Spray | 10 | 6.22 | 33.9 | 0.287 |
| (Standard Error) | | (±0.66) | (±8.48) | |
| 95% confid. interval | | 4.69-7.75 | 14.31-53.46 | |

Comparison of the Therapeutic Effect of Dorsonasally-Administered Ropivacaine and the Therapeutic Effect of Intranasally-Administered Lidocaine The anesthetic effect of 0.75% (w/v) ropivacaine-HCl is approximately equivalent to that of 3% (w/v) lidocaine. Intranasal spray administration of 1-2 milliliters of a 4% (w/v) lidocaine solution was 55% effective to reduce pain associated with migraine (Maizels et al., 1996, J. Amer. Med. Assoc. 276:319-321). By comparison, as described herein, dorsonasal spray administration of a 0.75% (w/v) ropivacaine solution was 100% effective to reduce pain associated with migraine. Furthermore, when dorsonasal administration of the ropivacaine solution was effected by topical application using a cotton swab saturated with the solution, reduction of migraine pain was achieved in 100% of patients. Preliminary data indicate that bupivacaine exhibits efficacy similar to that of ropivacaine for the relief of headache pain associated with migraine.

A comparison of ropivacaine and lidocaine on the basis of migraine pain relief per unit weight is provided in Table 5. This comparison indicates that dorsonasally spray-administered ropivacaine is 2.4 times as potent as intranasally spray-administered lidocaine, and that dorsonasally swab-administered ropivacaine is more than 15 times as potent as intranasally spray-administered lidocaine. Furthermore, as indicated in Table 5, the rate of migraine rebound is much lower following dorsonasal administration of ropivacaine, whether administered by nasal spray or by cotton swab, than it is following intranasal administration of lidocaine. Thus, the data presented herein indicate that ropivacaine is a much more efficacious agent for migraine pain relief than is lidocaine and that treatment of migraine by dorsonasal ropivacaine administration has a significantly lower rebound rate than treatment by intranasal administration of lidocaine.

TABLE 5

Comparison of the efficacy of migraine treatment by dorsonasal ropivacaine administration and the efficacy by intranasal lidocaine administration. "Rate" indicates the rate of migraine pain reduction per minute per gram of drug administered to the patient. Pain was rated using a 10-point pain scale, as described herein.

| Drug | Route of Administration | Rate of Pain Relief | Relative Efficacy[1] | Rebound Rate |
|---|---|---|---|---|
| Lidocaine | Intranasal Spray | 10.0 | 1.00 | 42% |
| Ropivacaine | Dorsonasal Spray | 24.5 | 2.45 | 10% |
| Ropivacaine | Dorsonasal Swab | 155 | 15.5 | 4% |

[1]Relative Efficacy means the Rate of Pain Relief for the indicated drug administered by the indicate route divided by the Rate of Pain Relief for intranasally spray-administered lidocaine.

Figure 3:
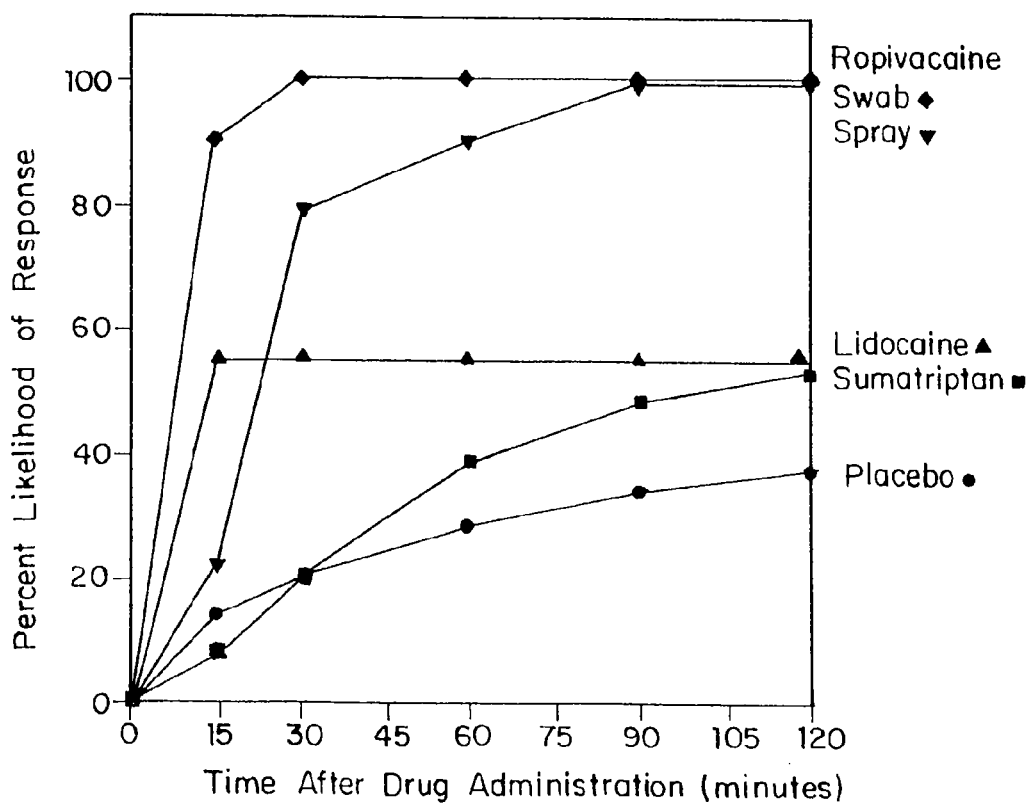
FIG. 3 is a graph which depicts the percentage of patients who exhibited at least 50% reduction in pain intensity following administration of various pharmaceutically active agents. The response of patients to whom a placebo was a placebo is indicated by filled circles (●; data from Maizels et al., 1996, J. Amer. Med. Assoc. 276:319-321 and The Subcutaneous Sumatriptan International Study Group, 1991, New Eng. J. Med. 325:316-321); the response of patients to whom sumatriptan was administered (as described in The Subcutaneous Sumatriptan International Study Group, 1991, New Eng. J. Med. 325:316-321) is indicated by filled squares; the response of patients to whom lidocaine was administered (as described in Maizels et al., 1996, J. Amer. Med. Assoc. 276: 319-321) is indicated by filled triangles; the response of patients to whom ropivacaine was administered by nasal spray as described herein in Example 1 is indicated by filled inverted triangles; the response of patients to whom ropivacaine was administered by cotton swab as described herein in Example 1 is indicated by filled diamonds.

Comparison of the Therapeutic Effect of Ropivacaine and the Therapeutic Effects of Other Anti-Migraine Pharmaceutically Active Agents In FIG. 3, the data obtained from the procedures performed in this Example are presented and compared with recently reported data obtained for administration of lidocaine to migraine patients (Maizels et al., 1996, J. Amer. Med. Assoc. 276:319-321) or administration of sumatriptan to migraine patients (The Subcutaneous Sumatriptan International Study Group, 1991, New Eng. J. Med. 325:316-321). Administration of ropivacaine resulted in an earlier onset of relief and a higher response rate than did administration of sumatriptan. Although the time of onset of relief using ropivacaine was roughly equal to the time of onset of relief using lidocaine, administration of ropivacaine treatment resulted in a nearly two-fold greater response rate than did administration of lidocaine. The response rate obtained by administration of ropivacaine to migraine patients was greater than the response rate obtained by administration of rizatriptan to such patients. In addition, the rebound rate following ropivacaine administration was lower than the rebound rate following rizatriptan administration (Kramer et al., 1997, Headache 36:268-269). The rapid and non-relapsing effects attributable to dorsonasal administration of ropivacaine are not observed following administration of lidocaine or a serotonin receptor agonist administered by the same route (Mills et al., 1997, Ann. Pharmacother. 31:914-915; Moore et al., 1997, Cephalalgia 17:541-550; Kramer et al., 1997, Headache 36:268-269).

While not wishing to be bound by any particular theory of operation, it is believed that dorsonasally administered ropivacaine inhibited migraine by anesthetizing a DnNS such as the SPG. Ropivacaine is ideally suited for anesthesia of a DnNS in general, and for migraine relief in particular. Ropivacaine exhibits intermediate lipid solubility and an intermediate half life in vivo, properties that limit possible toxicity. Direct application of ropivacaine to the region of the nasal epithelium overlying the SPG reduces the likelihood of systemic distribution of the compound, thereby limiting the likelihood of numerous side effects. Furthermore, direct application of ropivacaine to the region of the nasal epithelium overlying the SPG reduces the amount of ropivacaine which must be administered in order to provide an effective concentration at the SPG for relief of an acute migraine episode. Ropivacaine and other local anesthetics related to aminoacyl local anesthetics are known to selectively affect sensory neurons, relative to motor neurons, representing another advantage of using ropivacaine in the method of the invention. It is believed that direct administration of ropivacaine to the region of the nasal epithelium overlying the SPG, or to the region of the nasal epithelium near that region, arrests the cascade of neurotransmitter and neuropeptide release and stimulation that lead to neurogenic inflammation observed in the course of an acute migraine episode.

The ropivacaine molecule has the following structure (V), wherein the carbon atom indicated by the asterisk is a chiral center:

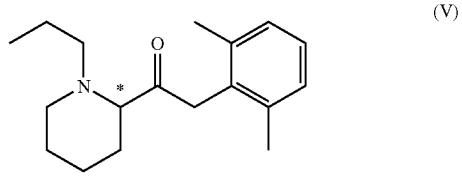

(V)

Cardiotoxicity is a side effect of administration of the R(dextro) enantiomer of ropivacaine, but this side effect is not exhibited by the S(levo) enantiomer (deJong, 1995, Reg. Anesth. 20:474-481). For this reason, ropivacaine is prepared as a sterile solution containing only the S(levo) enantiomer. The bupivacaine molecule also comprises a chiral center, but currently commercially available bupivacaine preparations include both the S and the R enantiomers.

Many of the patients described in this Example were observed for up to seven days, and 95% of those patients experienced no rebound during this period. This result contrasts with the results obtained following intranasal lidocaine administration. Of the 55% of patients who exhibited relief following intranasal lidocaine administration, at least 42% experienced rebound, usually within one hour post-treatment (Maizels et al., 1996, J. Amer. Med. Assoc. 276:319-321). Similarly, administration of either sumatriptan or rizatriptan resulted in inhibition of pain in 40-50% of patients within two hours post treatment, and patients who were administered either of these compounds frequently experienced rebound (The Subcutaneous Sumatriptan International Study Group, 1991, New Eng. J. Med. 325:316-321; Kramer et al., 1997, Headache 36:268-269).

EXAMPLE 2

Dorsonasal Administration of Bupivacaine for Inhibition of Acute Migraine Episodes The purpose of the experiments described in this Example was to determine the efficacy of dorsonasal administration of bupivacaine for inhibition of acute migraine episodes. Bupivacaine was dorsonasally administered to individual patients experiencing head pain, other symptoms, or both, believed to be associated with an acute migraine episode. Patients assessed head pain prior to and after bupivacaine administration.

Dorsonasally administered bupivacaine provided rapid arrest of migraine in all seven patients to whom it was administered within 10 minutes or less. Symptoms such as nausea, visual changes, and photophobia associated with acute migraine episodes in the patients were similarly reduced. Six of the seven patients treated using bupivacaine experienced no rebound of their migraine within twenty-four hours of treatment. The other patient experienced a recurrence of head pain four hours following a first administration of bupivacaine and another episode of head pain eight hours following a second administration of bupivacaine. These results demonstrate that dorsonasal administration of bupivacaine is an efficacious method of inhibiting an acute migraine episode.

The materials and methods used in the procedures performed in this Example were substantially the same as the materials and methods described in Example 1, with the exception that the composition which was administered to the patients described in this example comprised a 0.75% (w/v) solution of bupivacaine.

The results of treatment of each of the seven patients described in this Example with bupivacaine are presented in Table 6. The organization of and the abbreviations used in Table 6 are analogous to those used in Table 1, with the exception that "B" in the treatment column refers to bupivacaine. These results indicate that dorsonasal administration of bupivacaine is effective to inhibit acute migraine episodes.

TABLE 6

Summary of Patient Data.

| Patient Identifier | Medical History | Headache History | Associated Symptoms | Treatment | Results |
|---|---|---|---|---|---|
| P2#1 | | Migraine | Nausea | B 0.75% 2 Sprays | Initial pain: 5 Pain 10 min post-treatment: 0 No rebound up to 24 hours |
| P2#2 | | Migraine | Nausea Photophobia | B 0.75% Sat'd Cotton Swab | Initial pain: 7 Pain 5 min post-treatment: 0 No rebound up to 24 hours |

TABLE 6-continued

Summary of Patient Data.

| Patient Identifier | Medical History | Headache History | Associated Symptoms | Treatment | Results |
|---|---|---|---|---|---|
| P2#3 | | Migraine | Visual Changes and nausea as aura. Followed by head pressure and severe head pain at right occipital to front areas | B 0.75% 2 cc Drops | Initial pain: 10 Pain 5 min post-treatment: 1-2 Head pressure persisted No rebound up to 24 hours |
| P2#4 | Sinus Surgery | Migraine Triggered by Chocolate Ingestion | | B 0.75% 2 Sprays | Initial pain: 8 Pain 5 min post-treatment: 0 Recurrence 4 hours post-treatmt. Pain 5 min post-2nd-treatment: 0 Recurrence 8 hours post-treatmt. |
| P2#5 | | Mixed Headache | Nausea Photophobia | B 0.75% 2 Sprays | Initial pain: 8 Pain 10 min post-treatment: 0 No rebound up to 24 hours |
| P2#6 | | Migraine | | B 0.75% 2 Sprays | Initial pain: 8 Pain 3 min post-treatment: 0 No rebound up to 24 hours |
| P2#7 | | Migraine | Visual Changes | B 0.75% 2 cc Drops | Initial pain: 10 Pain 10 min post-treatment: 0 No rebound up to 24 hours |

EXAMPLE 3

Inhibiting a Recurring Cerebral Neurovascular Disorder by Dorsonasally Administering a Long-Acting Local Anesthetic Decreases the Frequency and Severity of Subsequent Episodes The following studies relate to the methods of decreasing the frequency and severity of CNvD episodes described herein, and involved three patients.

A 25-year-old female patient, herein designated "patient 3-1" was afflicted with recurring severe migraine, wherein acute migraine episodes were associated with nausea and visual changes. Patient 3-1 generally rated the severity of head pain associated with acute migraine episodes in the range from five to eight using the pain scale described herein. Patient 3-1 experienced, on average, about one acute migraine episode per week prior to beginning dorsonasal ropivacaine therapy. In addition, patient 3-1 also usually experienced about one severe acute migraine episode per month, associated with menses, wherein the severity of head pain was from eight to ten using the pain scale described herein. Patient 3-1 did not respond satisfactorily to administration of beta blockers and sumatriptan.

Ropivacaine was dorsonasally administered to patient 3-1 using the cotton swab technique described herein. The patient has consistently experienced relief from all of the symptoms of her CNvD episodes within 3 to 5 minutes following administration of ropivacaine, regardless of whether the episodes are associated with menses.

Patient 3-1 has continued treatment according to this method for about six months. After beginning the ropivacaine treatment, the patient discontinued use of sumatriptan and propanolol. Discontinuing these medications did not result in a loss of efficacy attributable to ropivacaine administration. Starting about three or four months following initiation of ropivacaine administration, the patient noticed a decrease in the initial severity of acute migraine episodes not associated with menses. At about the same time, the patient further noticed a decrease in the frequency with which acute migraine episodes not associated with menses occurred. No decrease in either the initial severity or the frequency of acute migraine episodes associated with menses has been reported by the patient. Patient 3-1 continues to experience relief from the head pain and other symptoms of acute migraine episodes, including those associated with menses, upon administration of ropivacaine.

A 45-year-old male, herein designated, "patient 3-2," was afflicted with recurring migraines. The acute migraine episodes began when he was a teenager, and have significantly worsened over the past 15 years. Head pain associated with the patient's acute migraine episodes is typically preceded by visual changes which he describes as a curtain-like wave of scotomata moving from left to right until he is unable to see. The patient then becomes disoriented with respect to time and place and must sit or lay down. Following these prodromal symptoms, a severe headache, rated 10 on the pain scale described herein, begins and typically endures for 45 to 60 minutes. The patient remains completely debilitated for the duration of the headache, unable to move about or walk. As the headache subsides, the patient's vision returns, and the patient is left feeling exhausted, as if he had not slept the night before.

Following dorsonasal administration of ropivacaine, delivered by the nasal spray method described herein, patient 3-2 noticed an abrupt halt to the progression of visual changes and steady resolution of his visual deficit. The headache rapidly decreased in intensity, decreasing from a pain intensity of 10, using the pain scale described herein, to an intensity of 2-3 within one to two minutes. The headache was completely resolved by fifteen minutes following ropivacaine administration. This patient also noted that he did not feel exhausted following the treated acute migraine episode. After four to six months of dorsonasal ropivacaine therapy, the patient noted that his headaches occurred less frequently, at a rate of approximately one headache every two months or longer. Furthermore, the severity of the headaches that patient 3-2 experienced was significantly reduced following this course of therapy. Prior to the course of dorsonasal ropivacaine therapy, the patient's headaches ordinarily had a pain intensity of about 10; after four to six months of this therapy, the initial headache pain (i.e., even prior to ropivacaine administration) was not greater than about 2. The patient reports significant lifestyle improvement, and is not aware of any other changes, for example changes in diet, sleep, exercise, environment, or medication, that could account for this improvement.

A 40-year-old female, herein designated, "patient 3-3," experienced about 3 to 5 recurring migraine episodes per week prior to beginning dorsonasal ropivacaine therapy. The initial severity of these headaches was reported to be 10, using the pain scale described herein. When ropivacaine was administered, using the saturated swab method described herein, to patient 3-3 during a headache episode, the patient reported a decrease in head pain from a rating of 10 to a rating of 0 or 1 within 10 minutes following ropivacaine administration. Furthermore, after three months of dorsonasal ropivacaine treatment, patient 3-3 reported that the frequency of her headache episodes had decreased to about 1 to 2 times weekly and that the initial severity of her headaches was in the range from about 7 to about 8, rather than 10.

The data described in this Example indicate that dorsonasal administration of ropivacaine to a patient afflicted with a recurring CNvD both inhibits a single episode of the CNvD and decreases the frequency and initial severity of the episodes associated with the recurring CNvD. Thus, the compositions, kits, and methods of the invention are useful for decreasing the frequency with which a patient afflicted with a recurring CNvD experiences a CNvD episode and for otherwise inhibiting the CNvD.

EXAMPLE 4

Inhibition of Tinnitus by Dorsonasal Administration of Ropivacaine

The data presented in this example demonstrate that symptoms of tinnitus may be inhibited by dorsonasal administration of a local anesthetic. Ropivacaine was dorsonasally administered to each of three patients using the nasal spray method or the nasal drops method described herein. All three patients experienced inhibition of tinnitus.

The first patient, herein designated, "patient 4-1," was a healthy male patient in his thirties who was afflicted with occasional migraines complicated by bilateral tinnitus about once every two to three months. Dorsonasal spray administration of ropivacaine to patient 4-1 relieved the head pain and tinnitus symptoms experienced by this patient within about five minutes following administration.

The second patient, herein designated, "patient 4-2," was a male in his forties who was afflicted with chronic head, neck, back, and shoulder pain resulting from trauma sustained during multiple motor vehicle accidents. Patient 4-2 was afflicted with constant head pain for which he used large quantities of intranasally-administered butorphanol. It was believed that the patient's headaches did not have a neurovascular etiology. Patient 4-2 is also afflicted with continuous bilateral tinnitus. Following dorsonasal spray administration of ropivacaine to patient 4-2, the patient reported a decrease in head pain of about 2 points, using the pain scale described herein, and furthermore experienced complete relief from symptoms of tinnitus for a period of 30 to 45 minutes. Interestingly, this patient noted a faster onset and a far more powerful effect on his chronic non-headache pain of intranasally administered butorphanol following intranasal administration of ropivacaine.

The third patient, herein designated, "patient 4-3," was a healthy male in his sixties who was afflicted with bilateral tinnitus for over 30 years. Following dorsonasal administration of 1 milliliter of 0.75% (w/v) ropivacaine into each nostril by the nasal drop method described herein, patient 4-3 experienced complete relief from tinnitus symptoms in his left ear and a 50-75% reduction in tinnitus symptoms in his right ear. This patient's relief from and reduction of symptoms persisted for about 30 to 45 minutes, after which period the tinnitus symptoms returned.

The results of the experiments described in this Example indicate that dorsonasal administration of a local anesthetic inhibits tinnitus. Even though the relief of tinnitus in these three patients was relatively short-lived (relative to migraine relief, as described herein), it must be borne in mind that no effective treatment exists for tinnitus. Thus, the treatment method described herein for tinnitus can be used to provide at least temporary relief to patients who have no effective long-term treatment options. Furthermore, the results presented in this Example suggest that a sustained release preparation of a local anesthetic or a local anesthetic causing a longer duration of anesthesia than ropivacaine may provide a longer period of inhibition of tinnitus than the ropivacaine preparation used in this method.

EXAMPLE 5

Dorsonasal Administration of Bupivacaine for Treatment of Muscular Headache Episodes The purpose of the experiments described in this Example was to determine the efficacy of dorsonasal administration of bupivacaine for inhibition of muscular headaches. Bupivacaine was dorsonasally administered to four individual patients experiencing head pain and other symptoms associated with a severe muscular headache episode. All of the patients had areas of sustained craniocervical muscle contraction and tenderness which was absent in all patients following headache resolution. Patients assessed head pain prior to and after bupivacaine administration. The four patients and their responses were as follows.

Patient 1

This patient was a 68-year-old female who experienced classic tension headache symptoms under stress. The patient normally experienced relief of tension headache symptoms following administration of ibuprofen. The patient was administered 0.75% bupivacaine during a tension headache episode, and thereafter experienced relief of her headache symptoms. The patient's pain intensity, as assessed using the pain scale described herein, decreased from about 8 to 0 within about 15 minutes after bupivacaine administration.

Patient 2

This patient was a 38-year-old male who experienced typical muscle contraction headache symptoms. The patient normally experienced relief of headache symptoms following administration of acetaminophen. The patient was administered 0.75% bupivacaine during a muscle contraction headache episode, and thereafter experienced relief of his headache symptoms within seven minutes following bupivacaine administration. The patient's pain intensity, as assessed using the pain scale described herein, decreased from about 7 to 0 within about 7 minutes after bupivacaine administration.

Patient 3

This patient was a 25-year-old male who experienced cervical neck pain symptoms associated with tension headache. The patient experienced moderate relief of headache symptoms following administration of non-steroidal anti-inflammatory drugs, including ibuprofen. The patient was administered 0.75% bupivacaine during a tension headache episode, and thereafter experienced relief of his headache symptoms. The patient's pain intensity, as assessed using the pain scale described herein, decreased from about 5 to about 1 within about 5 minutes after bupivacaine administration.

Patient 4

This patient was a 44-year-old female who experienced tension headaches. The patient was administered 0.75% bupivacaine during a tension headache episode, and thereafter experienced relief of neck pain and bi-temporal tension headache pain symptoms. The patient's pain intensity, as assessed using the pain scale described herein, decreased from about 7 to about 1 within about 5 minutes after bupivacaine administration. Prior to bupivacaine administration, the patient experienced mild residual pain in response to deep palpation of affected neck and temple muscles. This pain was perceived to be markedly decreased following treatment, and muscle knots were no longer perceived 5 minutes after treatment.

It is recognized that the muscular headache inhibition described in this Example may have been secondary to neurovascular effects of a dorsonasally administered local anesthetic or to effects on one or both of intracranial or extracranial neural or vascular structures, as described herein.

EXAMPLE 6

Dorsonasal Administration of a Eutectic Mixture of Local Anesthetics

An amount (0.5-1.0 milliliters) of a commercially available eutectic mixture of local anesthetics (prilocalne/lidocaine, 2.5% (w/v) each; EMLA™, Astra USA, Westborough, Mass.) was dorsonasally administered to each of six healthy adults using a syringe having a flexible applicator attached thereto. None of the six adults noted oropharyngeal numbness, unpleasant taste, or any other side effect normally associated with administration of a local anesthetic following intranasal administration.

The same amount of the mixture was dorsonasally administered to five patients afflicted with headaches. Each of these five patients experienced complete or nearly complete inhibition of head pain and other symptoms of their headaches within ten minutes following administration.

EXAMPLE 7

Dorsonasal Headache Treatment Using Lidocaine

Three headache patients were treated by delivering about 20-50 milligrams of a 10% (w/v) lidocaine solution to each nostril of the patients. The solution was administered by spraying it through a plastic cannula which had been bent to conform its shape such that the outlet of the cannula was located dorsonasally. The cannula was inserted into each nostril, and the solution was sprayed through the cannula, exiting therefrom through the outlet. All three patients experienced rapid relief from their headache symptoms; however, headache symptoms rebounded in two of the patients in less than one hour.

EXAMPLE 8

Dorsonasal Headache Treatment Using Bupivacaine

Two different headache patients were treated by delivering about 0.25-0.75 milliliters of a 0.75% (w/v) bupivacaine solution to each nostril of the patients. The solution was administered by passing the solution along a plastic cannula having an absorbent portion affixed at the distal (i.e., outlet) portion thereof. This cannula had also been bent to conform its shape such that the outlet of the cannula and the affixed absorbent portion were located dorsonasally. The solution was passed along the cannula, and the cannula was left in place for several minutes. Both of these patients experienced rapid relief from their headache symptoms, and neither patient experienced rebound of headache symptoms within about one day, the end of the follow-up period for these patients.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting a cerebral neurovascular disorder associated with pain in a human patient, the method comprising implanting an electronic neural stimulator in patient tissue adjacent a dorsonasal nerve structure and energizing the implanted electronic neural stimulator, so as to inhibit pain.

2. The method of claim 1 wherein the dorsonasal nerve structure is an SPG or branch thereof.

3. The method of claim 1 further comprising providing power to the implanted electronic neural stimulator using an external power supply.

4. The method of claim 3 wherein the step of providing power comprises inductively coupling the external power supply to the electronic neural stimulator.

5. The method of claim 1 further comprising effecting nerve block of the dorsonasal nerve structure.

6. A method of inhibiting migraine or headache in a human patient, the method comprising implanting an electronic neural stimulator in patient tissue adjacent a dorsonasal nerve structure and energizing the implanted electronic neural stimulator to effect nerve block of the dorsonasal nerve structure, so as to inhibit the migraine or the headache.

7. The method of claim 6 wherein the dorsonasal nerve structure is an SPG or branch thereof.

8. The method of claim 6 further comprising providing power to the implanted electronic neural stimulator using an external power supply.

9. The method of claim 8 wherein the step of providing power comprises inductively coupling the external power supply to the electronic neural stimulator.

* * * * *